US009250169B2

(12) United States Patent
Ju et al.

(10) Patent No.: US 9,250,169 B2
(45) Date of Patent: Feb. 2, 2016

(54) SELECTIVE CAPTURE AND RELEASE OF ANALYTES

(71) Applicant: THE TRUSTEES OF COLUMBIA UNIVERSITY IN THE CITY OF NEW YORK, New York, NY (US)

(72) Inventors: Jingyue Ju, Englewood Cliffs, NJ (US); Donald W. Landry, New York, NY (US); Qiao Lin, New York, NY (US); ThaiHuu Nguyen, Richmond, VA (US); Renjun Pei, Jiangsu (CN); Chunmei Oiu, New York, NY (US); Milan N. Stojanovic, Fort Lee, NJ (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 13/652,214

(22) Filed: Oct. 15, 2012

(65) Prior Publication Data

US 2014/0038301 A1    Feb. 6, 2014

Related U.S. Application Data

(60) Division of application No. 12/568,651, filed on Sep. 28, 2009, now abandoned, which is a continuation-in-part of application No. PCT/US2008/058433, filed on Mar. 27, 2008.

(Continued)

(51) Int. Cl.
*C12Q 1/68* (2006.01)
*G01N 1/40* (2006.01)
*G01N 21/64* (2006.01)

(52) U.S. Cl.
CPC ............ *G01N 1/4055* (2013.01); *C12Q 1/6816* (2013.01); *G01N 21/6408* (2013.01); *Y10T 436/143333* (2015.01); *Y10T 436/24* (2015.01); *Y10T 436/25375* (2015.01)

(58) Field of Classification Search
CPC . G01N 1/4055; G01N 21/6408; C12Q 1/6816
USPC .......................................... 435/6.1; 436/177
See application file for complete search history.

(56) References Cited

U.S. PATENT DOCUMENTS

| 5,508,164 A | 4/1996 | Kausch et al. |
| 5,968,820 A | 10/1999 | Zborowski et al. |

(Continued)

FOREIGN PATENT DOCUMENTS

| EP | 1 903 338 | 3/2008 |
| KR | 1020090032457 | 5/2009 |

(Continued)

OTHER PUBLICATIONS

U.S. Appl. No. 12/568,651, Dec. 31, 2012 Notice of Abandonment.

(Continued)

*Primary Examiner* — Betty Forman
(74) *Attorney, Agent, or Firm* — Baker Botts L.L.P.

(57) ABSTRACT

The described subject matter includes techniques and components for minimally invasive, selective capture and release of analytes. An aptamer is selected for its binding affinity with a particular analyte(s). The aptamer is functionalized on a solid phase, for example, microbeads, polymer monolith, microfabricated solid phase, etc. The analyte is allowed to bind to the aptamer, for example, in a microchamber. Once the analyte has been bound, a temperature control sets the temperature to an appropriate temperature at which the captured analyte is released.

21 Claims, 51 Drawing Sheets

Related U.S. Application Data

(60) Provisional application No. 61/165,690, filed on Apr. 1, 2009, provisional application No. 61/171,333, filed on Apr. 21, 2009, provisional application No. 60/989,182, filed on Nov. 20, 2007, provisional application No. 60/987,474, filed on Nov. 13, 2007, provisional application No. 60/972,061, filed on Sep. 13, 2007, provisional application No. 60/968,803, filed on Aug. 29, 2007, provisional application No. 60/908,304, filed on Mar. 27, 2007, provisional application No. 60/908,298, filed on Mar. 27, 2007.

(56) References Cited

U.S. PATENT DOCUMENTS

| | | |
|---|---|---|
| 5,998,588 A | 12/1999 | Hoffman et al. |
| 6,344,326 B1 | 2/2002 | Nelson et al. |
| 6,479,242 B1 | 11/2002 | Gou et al. |
| 6,641,783 B1 | 11/2003 | Pidgeon et al. |
| 7,029,852 B2 | 4/2006 | Leibholz et al. |
| 7,141,375 B2 | 11/2006 | Pietras et al. |
| 7,151,167 B2 | 12/2006 | Gjerde et al. |
| 7,217,542 B2 | 5/2007 | Tyvoll et al. |
| 7,285,412 B2 | 10/2007 | Casagrande et al. |
| 7,338,762 B2 | 3/2008 | Gorenstein et al. |
| 7,413,712 B2 | 8/2008 | Liu et al. |
| 7,887,753 B2 | 2/2011 | Quake et al. |
| 7,932,034 B2 | 4/2011 | Esfandyarpour et al. |
| 7,964,356 B2 | 6/2011 | Zichi et al. |
| 8,124,015 B2 | 2/2012 | Diercks et al. |
| 2002/0039783 A1 | 4/2002 | McMillan et al. |
| 2004/0005582 A1 | 1/2004 | Shipwash |
| 2004/0043509 A1 | 3/2004 | Stahler et al. |
| 2004/0126890 A1 | 7/2004 | Gjerde et al. |
| 2004/0241718 A1 | 12/2004 | McGown |
| 2005/0069910 A1* | 3/2005 | Turner et al. ............... 435/6 |
| 2005/0142582 A1* | 6/2005 | Doyle et al. ............... 435/6 |
| 2005/0208487 A1* | 9/2005 | Burmeister et al. ......... 435/6 |
| 2005/0250117 A1 | 11/2005 | Su et al. |
| 2006/0172429 A1 | 8/2006 | Nilsson et al. |
| 2006/0205061 A1 | 9/2006 | Roukes et al. |
| 2007/0122811 A1 | 5/2007 | Buzby |
| 2007/0184456 A1 | 8/2007 | Chee et al. |
| 2007/0292397 A1 | 12/2007 | McNulty et al. |
| 2008/0014576 A1 | 1/2008 | Jovanovich et al. |
| 2008/0056946 A1 | 3/2008 | Ahmad |
| 2008/0132188 A1 | 6/2008 | Nivio et al. |
| 2008/0245971 A1 | 10/2008 | Wimberger-Friedl et al. |
| 2008/0264842 A1 | 10/2008 | Hukari et al. |
| 2009/0011451 A1 | 1/2009 | Rodriguez et al. |
| 2009/0048124 A1 | 2/2009 | Leamon et al. |
| 2009/0166196 A1 | 7/2009 | Kayyem |
| 2009/0227044 A1 | 9/2009 | Dosey et al. |
| 2010/0151465 A1 | 6/2010 | Ju et al. |
| 2010/0279283 A1 | 11/2010 | Raghunath et al. |
| 2010/0297733 A1 | 11/2010 | Lin et al. |
| 2011/0143949 A1 | 6/2011 | Heid et al. |
| 2012/0028811 A1 | 2/2012 | Craighead et al. |
| 2014/0248621 A1 | 9/2014 | Collins |

FOREIGN PATENT DOCUMENTS

| | | |
|---|---|---|
| WO | WO 2005/021725 | 3/2005 |
| WO | WO 2007/092713 | 8/2007 |
| WO | WO 2008/042481 | 4/2008 |
| WO | WO 2009/140326 | 11/2009 |
| WO | WO 2010/123521 | 10/2010 |
| WO | WO 2013/044240 | 3/2013 |

OTHER PUBLICATIONS

U.S. Appl. No. 12/568,651, Apr. 13, 2012 Final Office Action.
U.S. Appl. No. 12/568,651, Mar. 12, 2012 Response to Non-Final Office Action.
U.S. Appl. No. 12/568,651, Sep. 12, 2011 Non-Final Office Action.
U.S. Appl. No. 12/764,898, Apr. 29, 2013 Amendment and Request for Continued Examination (RCE).
U.S. Appl. No. 12/764,898, Nov. 28, 2012 Final Office Action.
U.S. Appl. No. 12/764,898, Sep. 5, 2012 Response to Non-Final Office Action.
U.S. Appl. No. 12/764,898, Jun. 5, 2012 Non-Final Office Action.
AAAT Bioquest, "Classic reactive flourescent labeling dyes & their applications", *AAT Bioquest, Inc. Product Technical Information Sheet*, 2010 [online]. Retrieved on Jan. 29, 2013 at http://www.biomol.de.details/AB/Classic_Reactive_Flourescent_Labeling_Dyes.pdf>.
Adams, et al., "Multitarget Magnetic Activated Cell Sorter", *Proceedings of the National Academy of Sciences of the United States of America*, 105:18165-18170 (2008).
Berger, et al., "Design of a Microfabricated Magnetic Cell Separator," *Electrophoresis*, 22:3883-3892 (2001).
Blazej, et al., "Microfabricated bioprocessor for integrated nanoliter-scale Sanger DNA sequencing", *PNAS*, 103(19):7240-7245 (2006).
Bock, et al., "Selection of single-stranded-DNA molecules that bind and inhibit human thrombin", *Nature*, 355:564-566 (1992).
Brody, et al,, "The use if aptamers in large arrays for molecular diagnostics", *Molecular Diagnosis*, 4(4):381-388 (1999).
Broyles, et al., "Sample filtration, concentration, and separation integrated on microfluidic devices", *Anal. Chemistry*, 75:2761-2767 (2003).
Burgstaller, et al., "Aptamers as tools for target prioritization and lead identification", *Drug Discovery Today*, 7(24):1221-1228 (2002).
Chang, et al., "Electrokinetic Mixing in Microfluidic Systems", *Microfluidics and Nanofluidics*, 3:501-525 (2007).
Chen, et al., "Total nucleic acid analysis integrated on microfluidic devices", *Lab on a Chip*, 7(11):1413-1423 (2007).
Cho, et al., "PDMS-glass serpentine microchannel chip for time domain PCR with bubble suppression in sample injection", *Journal of Micromechanics and Microengineering*, 17(9):1810-1817 (2007).
Chou, et al., "A microfabricated device for sizing and sorting DNA molecules", *PNAS*, 96(1):11-13 (1999).
Collett, et al., "Functional RNA microarrays for high-throughput screening of antiprotein aptamers", *Analytical Biochemistry*, 338(1):113-123 (2005).
Cox, et al., "Automated selection of anti-protein aptamers", *Bioorganic & Medicinal Chemistry*, 9(10):2525-2531 (2001).
Dahlin, et al., "Poly(dimethylsiloxane)-based microchip for two-dimensional solid-phase extraction-capillary electrophoresis with an integrated electrospray emitter tip", *Analytical Chemistry*, 77(16):5356-5363 (2005).
Darby, R., *Chemical Engineering Fluid Mechanics*, 2nd Edition, Revised and Expanded, (Marcel Dekker, New York, 2001) (Table of Contents).
Deng, et al., "Aptamer affinity chromatography for rapid assay of adenosine in microdialysis samples collected in vivo", *Journal of Chromatography A*, 1005(1-2):123-130 (2003).
Diehl, et al., "BEAMing: single-molecule PCR on microparticles in water-in-oil emulsions", *Nature Methods*, 3(7):551-559 (2006).
Dittmer, et al., "A DNA-based machine that can cyclically bind and release thrombin", *Angewandte Chemie—International Edition*, 43(27):3550-3553 (2004).
Doherty, et al., "Sparsely cross-linked "nanogel" matrixes as fluid, mechanically stabilized polymer networks for high-throughput microchannel DNA sequencing", *Anal. Chem.*, 76:5249-5256 (2004).
D'Orazio, et al., "Biosensors in clinical chemistry", *Clinica Chimica Acta*, 334:41-69 (2003).
Drabovich, et al., "Selection of smart aptamers by equilibrium capillary electrophoresis of equilibrium mixtures (ECEEM)", *Journal of the American Chemical Society*, 127(32):11224-11225 (2005).
Drabovich, et al., "Selection of smart aptamers by methods of kinetic capillary electrophoresis", *Anal. Chem.*, 78(9):3171-3178 (2006).
Earhart, et al., "Microfabricated magnetic sifter for high-throughput and high-gradient magnetic separation", *Journal of Magnetism and Magnetic Materials*, 321:1436-1439 (2009).

(56) References Cited

OTHER PUBLICATIONS

El-Ali, et al., "Cell stimulus and lysis in a microfluidic device with segmented gas-liquid flow", *Analytical Chemistry*, 77(11):3629-3636 (2005).
Espy, et al., "An Instrument for Sorting of Magnetic Microparticles in a Magnetic Field Gradient", *Cytometry Part A*, 69A:1132-1142 (2006).
Estes, et al., "On Chip Cell Separator Using Magnetic Bead-Based Enrichment and Depletion of Various Surface Markers", *Biomedical Microdevices*, 11:509-515 (2009).
Farokhzad, et al., "Targeted nanoparticle-aptamer bioconjugates for cancer chemotherapy in vivo", *PNAS*, 103(16):6315-6320 (2006).
Fivash, et al., "BIAcore for macromolecular interaction", *Current Opinion on Biotechnology*, 9(1):97-101 (1998).
Furdui, et al., "Immunomagnetic T cell capture from blood for per analysis using microfluidic systems", *Lab on a Chip*, 4:614-618 (2004).
Geiger, et al., "RNA aptamers that bind L-arginine with sub-micromolar dissociation constants and high enantioselectivity", *Nucleic Acids Research*, 24(6):1029-1036 (1996).
Giordano, et al., "Towards dynamic coating of glass microchip chambers for amplifying DNA via the polymerase chain reaction", *Electrophoresis*, 22(2):334-340 (2001).
Gopinath, S.C.B., "Methods developed for SELEX", *Analytical and Bioanalytical Chemistry*, 387(1):171-182 (2007).
Green, et al,, "Aptamers as reagents for high-throughput screening", *BioTechniques*, 30(5):1094-1110 (2001).
Hamula, et al., "Selection and analytical applications of aptamers", *Trends Anal. Chem.*, 25(7):681-691 (2006).
*Handbook of Affinity Chromatography*, 2 Edition. Edited by David S. Hage, Taylor and Francis, (Table of Contents) (2006).
Herr, et al., "Aptamer-conjugated nanoparticles for selective collection and detection of cancer cells", *Analytical Chemistry* 78(9):2918-2924 (2006).
Hessel, et al., "Micromixers—a Review on Passive and Active Mixing Principles", *Chemical Engineering Science*, 60:2479-2501 (2005).
Hoffman, et al., "Immobilized DNA aptamers used as potent attractors for porcine endothelial precursor cells", *Journal of Biomedical Materials Research Part A*, 84A(3):614-621 (2008).
Hsing, et al., "Mirco- and nano-magnetic particles for applications in biosensing", *Electroanalysis*, 10(7-8):755-768 (2007).
Huang, et al., Integrated microfluidic system for rapid screening of CRP aptamers utilizing systematic evolution of ligands by exponential enrichment (SELEX), *Biosensors and Bioelectronics*, 25(17): 1761-1766 (2010).
Hybarger, et al., "A microfluic SELEX prototype", *Analytical and Bioanalytical Chemistry*, 384(1):191-198 (2006).
Inglis, et al., "Continuous Microfluidic Immunomagnetic Cell Separation," *Applied Physics Letters*, 85(21):5093-5095 (2004).
James, W., "Aptamers in the virologists' toolkit", *Journal of General Virology*, 88(8):351-364 (2007).
Jellinek, et al., "Potent 2'-amino-2'-deoxypyrimidine RNA inhibitors of basic fibroblast growth-factor", *Biochemistry*, 34(36):11363-11372 (1995).
Jenison, et al., "High-resolution molecular discrimination by RNA", *Science*, 263(5152):1425-1429 (1994).
Jensen, et al., "Kinetics for hybridization of peptide nucleic acids (PNA) with DNA and RNA studied with the BIAcore technique", *Biochemistry*, 36(16):5072-5077 (1997).
Kanter, et al., "Cell-free production of SCFV fusion proteins: an efficient approach for personalized lymphoma vaccines", *Blood*, 109(8):3393-3399 (2007).
Kim, et al., "Solid phase capturable dideoxynucleotides for multiplex genotyping using mass spectrometry", *Nucleic Acids Research*, 30(16):e85 (2002).
Kopp, et al., "Chemical amplification: Continuous-flow PCR on a chip", *Science*, 280(5366):1046-1048 (1998).

Lai, et al., "Aptamer-based electrochemical detection of picomolar platelet-derived growth factor directly in blood serum", *Analytical Chemistry*, 79(1):229-233 (2007).
Lee, et al., "A therapeutic aptamer inhibits angiogenesis by specifically targeting the heparin binding domain of VEGF $_{165}$", *PNAS*, 102(52):18902-18907 (2005).
Lermo, et al., "In-situ DNA amplification with magnetic primers for the electrochemical detection of food pathogens", *Biosensors and Bioelectronics*, 22(9-10):2010-2017 (2007).
Lien, et al., "Purification and enrichment of virus samples utilizing magnetic beads on a microfluidic system", *Lab on a Chip*, 7:868-875 (2007).
Lin, et al., "Aptamer-Based Microfluidic Biosensors", *9th IEEE Conference on Nanotechnology*, pp. 812-814 (2009).
Liu, et al., "Micro air bubble formation and its control during polymerase chain reaction (PCR) in polydimethylsiloxane (PDMS) microreactos", *Journal of Micromechanics and Microengineering*, 17:2055-2064 (2007).
Liu, et al., "Passive Mixing in a Three-Dimensional Serpentine Microchannel", *Journal of Microelectromechanical Systems*, 9:190-197 (2000).
Lowe, et al., "Multiplex single nucleotide polymorphism genotyping utilizing ligase detection reaction coupled surface enhanced raman spectroscopy", *Analytical Chemistry*, 82(13):5810-5814 (2010).
Lund-Olesen, et al., "Capture of DNA in Microfluidic Channel Using Magnetic Beads: Increasing Capture Efficiency with Integrated Microfluidic Mixer", *Journal of Magnetism and Magnetic Materials*, 311:396-400 (2007).
Lupold, et al., "Identification and characterization of nuclease-stabilized RNA molecules that bind human prostate cancer cells via the prostate-specific membrane antigen", *Cancer Research*, 62(14):4029-4033 (2002).
Mannironi, et al,, "In vitro selection of dopamine RNA ligands", *Biochemistry*, 36(32):9726-9734 (1997).
Mendonsa, et al., "In-vitro evolution of functional DNA using capillary electrophoresis", *Journal of the American Chemical Society*, 126(1):20-21 (2004).
Miltenyi, et al., "High gradient magnetic cell separation with MACS", *Cytometry Part A.*, 11(2):231-238 (1990).
Misra, et al., "Microbead device for isolating biotinylated oligonucleotides for use in mass spectrometric analysis", *Analytical Biochemistry*, 384(1):96-100 (2009).
Mosing, et al., "Capillary electrophoresis-SELEX selection of aptamers with affinity for HIV-1 reverse transcriptase", *Anal. Chem.*, 77(19):6107-6112 (2005).
Murphy, et al., "An improved method for the in vitro evolution of aptamers and applications in protein detection and purification", *Nucleic Acids Research*, 31(18):e110 (2003).
Nieuwlandt, et al., "In-vitro selection of RNA ligands to substance-P", *Biochemistry*, 34(16):5651-5659 (1995).
Nimjee, et al., "The potential of aptamers as anticoagulants", *Trends Cardiovascular Medicine*, 15(1):41-45 (2005).
Nguyen, et al., "Micromixers—a Review", *Journal of Micromechanics and Microengineering*, 15:R1-R16 (2005).
Nguyen, et al., "An aptamer-based microfluidic device for thermally controlled affinity extraction", *Microfluid Nanofluid*, 6(4):479-487 (2009).
Oh, et al., "Screening of Molecular Libraries Using the Continuous-Flow, Micro-Magnetic Cell Sorter", *10th International Conference on Miniaturized Systems for Chemistry and Life Sciences*, Nov. 5-9, 2006, Tokyo, Japan, pp. 975-977.
O'Sullivan, et al., "Aptasensors—the future of biosensing", *Analytical and Bioanalytical Chemistry*, 372:44-48 (2002).
Pamme, et al., "Continuous sorting of magnetic cells via on-chip free-low magnetophoresis", *Lab on a Chip*, 6(8):974-980 (2006).
Prosek, et al., "Aptamers-basic research, drug development, and clinical applications", *Appl. Microbiol. Biotechnol.* 69:367-374 (2005).
Ramsey, et al., "Integrated microfluidic device for solid-phase extraction coupled to micellar electrokinetic chromatography separation", *Anal. Chem.*, 77:6664-6670 (2005).

(56) References Cited

OTHER PUBLICATIONS

Ravelet, et al,, "Liquid chromatography, electrochromatography, and capillary electrophoresis applications of DNA and RNA aptamers", *Journal of Chromatogrraphy A*, 1117:1-10 (2006).

Reigstad, et al., "Platelet-derived growth factor (PDGF)-C, a PDGF family member with a vascular endothelial growth factor-like structure", *The Journal of Biological Chemistry*, 278(19):17114-17120 (2003).

Reuter, et al., "Kinetics of protein-release by an aptamer-based DNA nanodevice", *European Physical Journal E.*, 22(1):33-40 (2007).

Romig, et al., "Aptamer affinity chromatography: combinatorial chemistry applied to protein purification", *Journal of Chromatography B-Analytical Technologies in the Biomedical and Life Sciences*, 731(2):275-284 (1999).

Shamah, et al., "Complex target SELEX", *Accounts of Chemical Research*, 41(1):130-138 (2008).

Shangguan, et al., "Cell-specific aptamer probes for membrane protein elucidation in cancer cells", *Journal of Proteome Research*, 7(5):2133-2139 (2008).

Shao, et al., "Emulsion PCR: A high efficient way of PCR amplification of random DNA libraries in aptamer selection", *PlosOne*, 6(9):E24910 (2011).

Sikavitsas, et al., "Transport and kinetic processes underlying biomolecular interactions in the BIACORE optical biosensor", *Biotechnology Progress*, 18(4):885-897 (2002).

So, et al., "Detection and titer estimation of *Escherichia coli* using aptamer-functionalized single-walled carbon-nanotube field-effect transistors", *Small*, 4(2):197-201 (2008).

Stroock, et al., "Controlling flows in microchannels with patterned surface charge and topography", *Accounts of Chemical Research*, 36(8):597-604 (2003).

Stroock, et al., "Chaotic Mixer for Microchannels", *Science*, 295:647-651 (2002).

Tang, et al., Chip-based genotyping by mass spectrometry, *PNAS*, 96(18):10016-10020 (1999).

Taylor, et al., "Dynamics of an anti-VEGF DNA aptamer: A single-molecule study", *Biochemical and Biophysical Research Communications*, 373(2):213-218 (2008).

Temples, et al., "On-line coupling of size exclusion chromatography and capillary electrophoresis via solid-phase extraction and a Tee-split interface", *Journal of Chromatography B*, 839:30-35 (2006).

Thorsen, et al., "Microfluidic large-scale integration", *Science*, 298 (5593):580-584 (2002).

Tombelli, et al., "Analytical applications of aptamers", *Biosensors and Bioelectronics*, 20:2424-2434 (2005).

Toriello, et al., "Integrated affinity capture, purification, and capillary electrophoresis microdevice for quantitative double-stranded DNA analysis", *Anal. Chem.*, 79(22):8549-8556 (2007).

Tuerk, et al., "Systematic evolution of ligands by exponential enrichment: RNA ligands to bacteriophage T4 DNA polymerase", *Science*, 249:505-510 (1990).

Unger, et al., "Monolithic microfabricated valves and pumps by multilayered soft lithography", *Science*, 288:113-116 (2000).

Verpoorte, "Beads and Chips: New Recipes for Analysis", *Lab on a Chip*, 3:60N-68N (2003).

Viskari, et al., "Unconventional detection methods for microfluidic devices", *Electrophoresis*, 27(9):1797-1810 (2006).

Wallis, et al., "Vasopressin is a physiological substrate for the insulin-regulated aminopeptidase IRAP", *Am. J. Physiol. Endocrinol. Metab.*, 293(4):E1092-E1102 (2007).

Wang, et al., "Demonstration of MEMS-based differential scanning calorimetry for determining thermodynamic properties of biomolecules", *Sensors and Actuators B: Chemical*, 134:953-958 (2008).

Wang, et al., "Pre-binding dynamic range and sensitivity enhancement for immuno-sensor using nanofluidic preconcentrator", *Lab on a Chip*, 8:392-394 (2007).

Williams, et al., "Bioactive and nuclease-resistant $_L$-DNA ligand of vasopressin", *PNAS*, 94(21):11285-11290 (1997).

Wu, et al., "MEMS flow sensors for nano-fluidic applications", *Sensors and Actuators A.*, 89(1-2):152-158 (2001).

Xia, et al., "Chaotic micromixers using two-layer crossing channels to exhibit fast mixing at low Reynolds numbers", *Lab on a Chip*, 5(7):748-755 (2005).

Xiaoyu, et al., "Polydimethylsiloxane (PDMS)-based spiral channel PCR chip", *Electronics Letters*, 46(16):890-891 (2005).

Xu, et al., "Aptamer-Based Microfluidic Device for Enrichment, Sorting, and Detection of Multiple Cancer Cells", *Anal. Chem.*, 81:7436-7442 (2009).

Yang, et al., "Advances in SELEX and application of aptamers in the central nervous system", *Biomolecular Engineering*, 24(6):583-592 (2007).

Yang, et al., "DNA ligands that bind tightly and selectively to cellobiose", *PNAS*, 95(10):5462-5467 (1998).

Yeung, et al., "A DNA biochip for on-the-spot multiplexed pathogen identification", *Nucleic Acids Res.*, 34(18):e118 (2006).

Yu, et al., "Preparation of monolithic polymers with controlled porous properties for microfluidic chip applications using photoinitiated free-radical polymerization", *Journal of Polymer Science Part A—Polymer Chemistry*, 40(6):755-169 (2002).

Zhang, et al., "In-vitro selection of bacteriophage ø 29 prohead RNA aptamers for prohead binding", *The Journal of Biological Chemistry,*, 273(5):2947-2953 (1998).

Zhang, et al., "Differentiation and detection of PDGF isomers and their receptors by tunable aptamer capillary electrophoresis", *Analytical Chemistry*, 81(18):7795-7800 (2009).

International Search Report for PCT/US2008/058433, dated Jun. 30, 2008.

International Search Report and Written Opinion for PCT/US2012/056888, dated Feb. 25, 2013.

International Search Report and Written Opinion for PCT/US2012/056926, dated Dec. 3, 2012.

U.S. Appl. No. 12/764,898, Jul. 21, 2014 Non-Final Office Action.

Suzuki et al., "Chaotic mixing of magnetic beads in microcell separator", Proc. 3rd Int. Symp. Turbulence and Shear Flow Phenomena, Jun. 24-27, 2003, pp. 817-822.

Inokuchi et al., "Development of micro immuno-magnetic cell sorting system with lamination mixer and magnetic separator" Proc. 25th Sensor Symp., 2008, pp. 1-2.

U.S. Appl. No. 14/223,767, filed Mar. 24, 2014.

U.S. Appl. No. 14/221,596, filed Mar. 21, 2014.

Jayasena, "Aptamers: An emerging class of molecules that rival antibodies in diagnostics", *Clinical Chemistry*, 45(9):1628-1650 (1999).

International Search Report and Written Opinion for PCT/US2013/070075, dated Feb. 21, 2014.

Xu et al., "Review: Aptamers in microfluidic chips", *Analytica Chimica Acta*, 683(1):12-20 (2010).

Chen et al., "An automatic microfluidic system that continuously performs the systematic evolution of ligands by exponential enrichment", *Microfluidics and Nanofluidics*, 13(6):929-939 (2012).

Kim et al., "A microchip for nucleic acid isolation and enrichment", *2012 IEEE 25th International Conference on Micro Electro Mechanical Systems*, pp. 765-768 (2012).

Ahn et al., "A sol-gel-based microfluidics system enhances the efficiency of RNA aptamer selection", *Oligonucleotides*, 21(2):93-100 (2011).

Sanchez-Freire et al., "Microfluidic single-cell real-time PCR for comparative analysis of gene expression patterns", Nature Protocols, 7:829-838 (Apr. 2012).

White et al., "High-throughput microfluidic single-cell RT-qPCR", PNAS, 108(34):13999-14004 (Aug. 2011).

Stahlberg et al., "Single-cell gene-expression profiling and its potential diagnostic applications", Exp. Rev. of Mol. Diagnostics, 11(7):735-740 (Sep. 2011).

\* cited by examiner

| Test Series Fluorescence | A | B | C |
|---|---|---|---|
| Baseline (a.u.) | 0.542 | 0.412 | 0.462 |
| 1st Extraction (a.u.) | 219 | 215 | 209 |
| Regeneration (a.u.) | 0.853 | 0.713 | 0.977 |
| 2nd Extraction (a.u.) | 210 | 38.5 | 11.1 |

FIG. 6

```
                              U   U
                          U       C
                       C              G
                    A        UGGCAC   G
                 A           ||||||   
              A              ACCGUG   
           G                         G
        A                           G
       A
       A
       G
        G
5' GGGUUG
   ||||||
3' CCCAAC
```

FIG. 7A

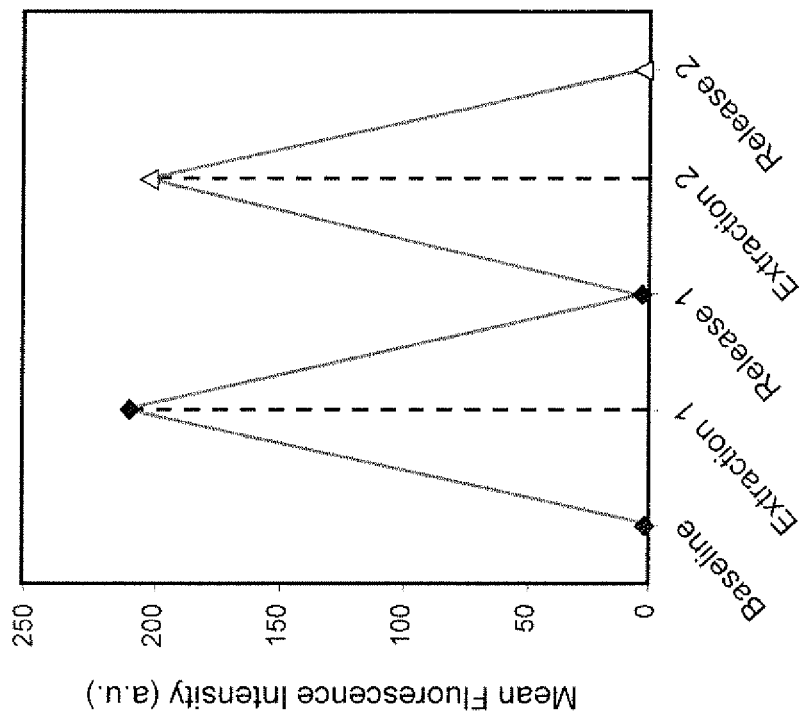
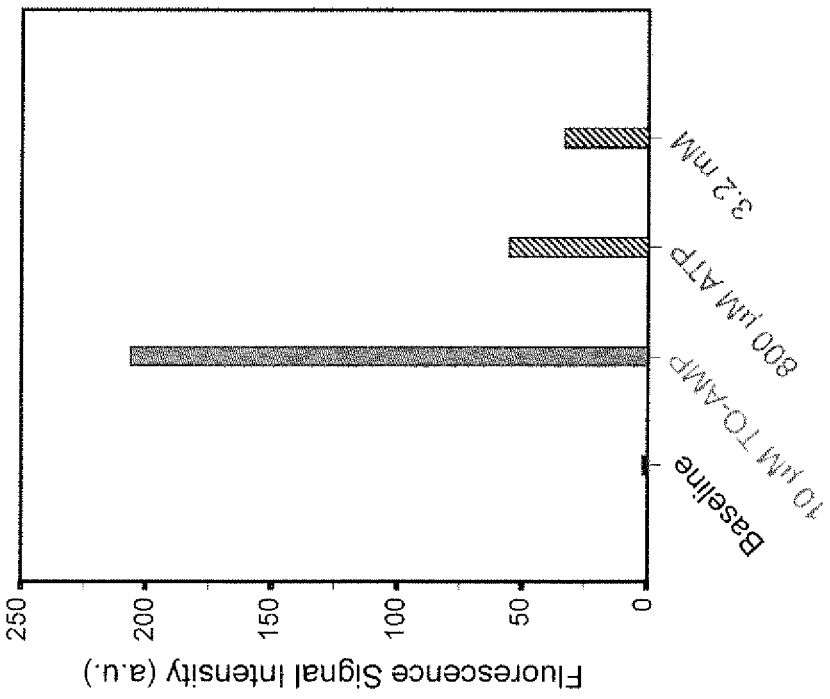
FIG. 13A
FIG. 13B

FIG. 15A
FIG. 15B
FIG. 15C
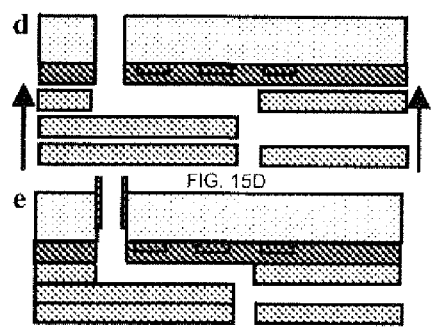
FIG. 15D
FIG. 15E

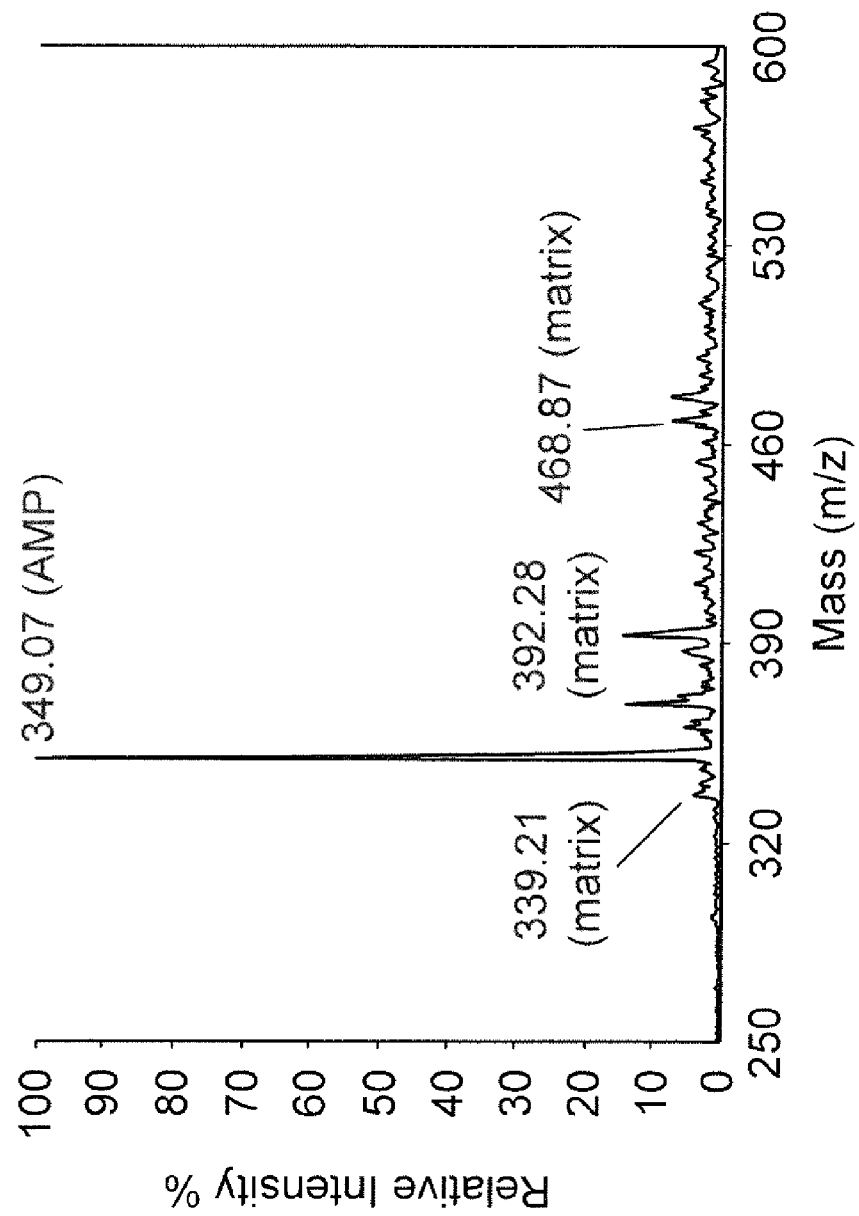

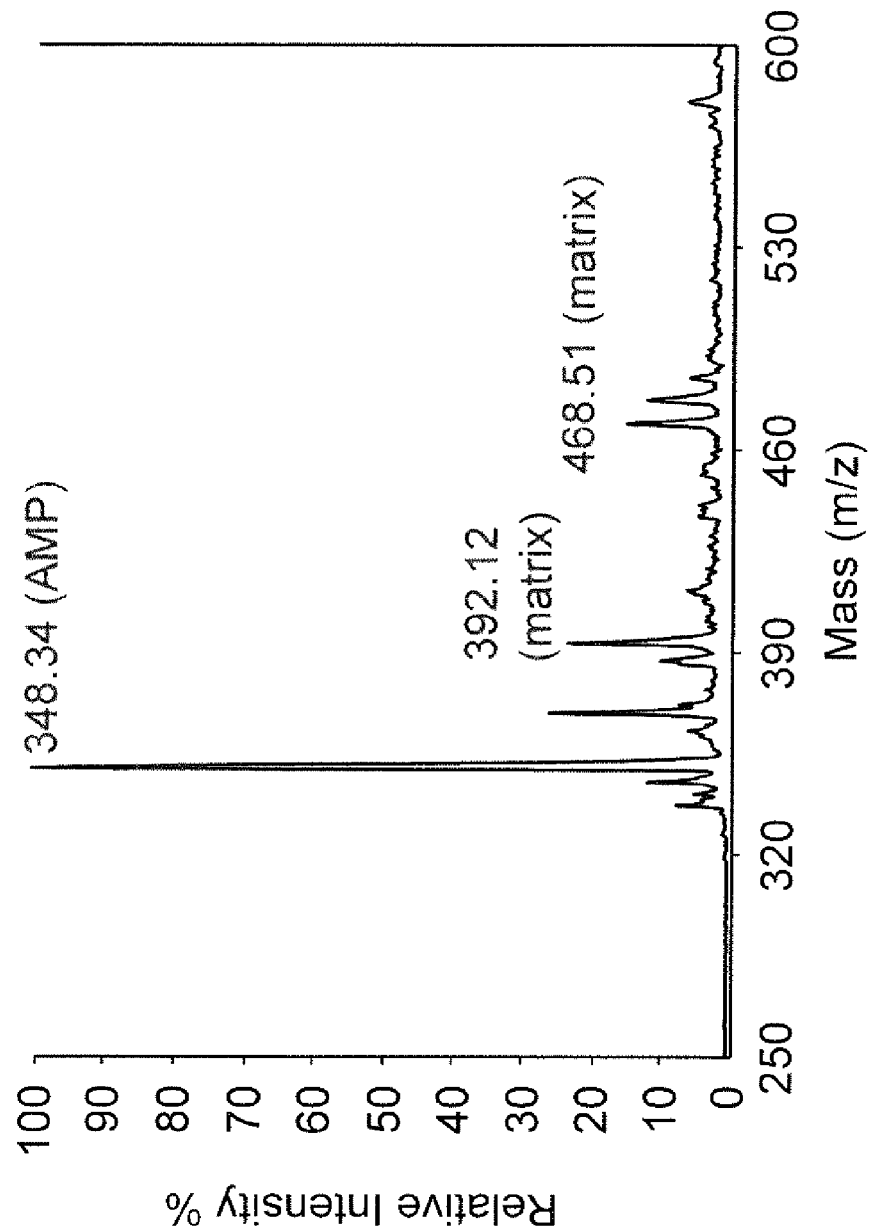

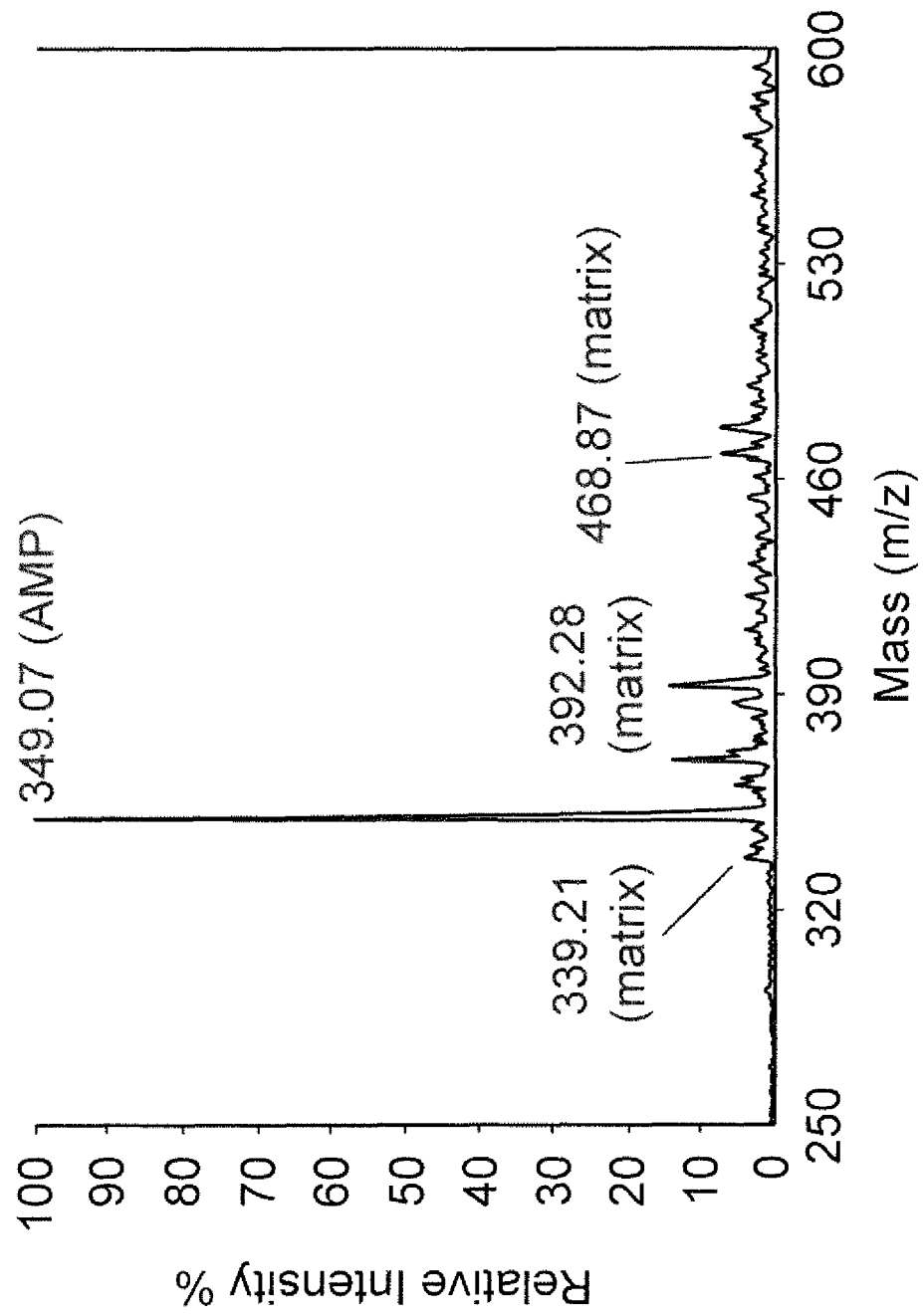

FIG. 22A
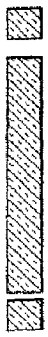
FIG. 22D
FIG. 22B
FIG. 22E
FIG. 22C
FIG. 22F

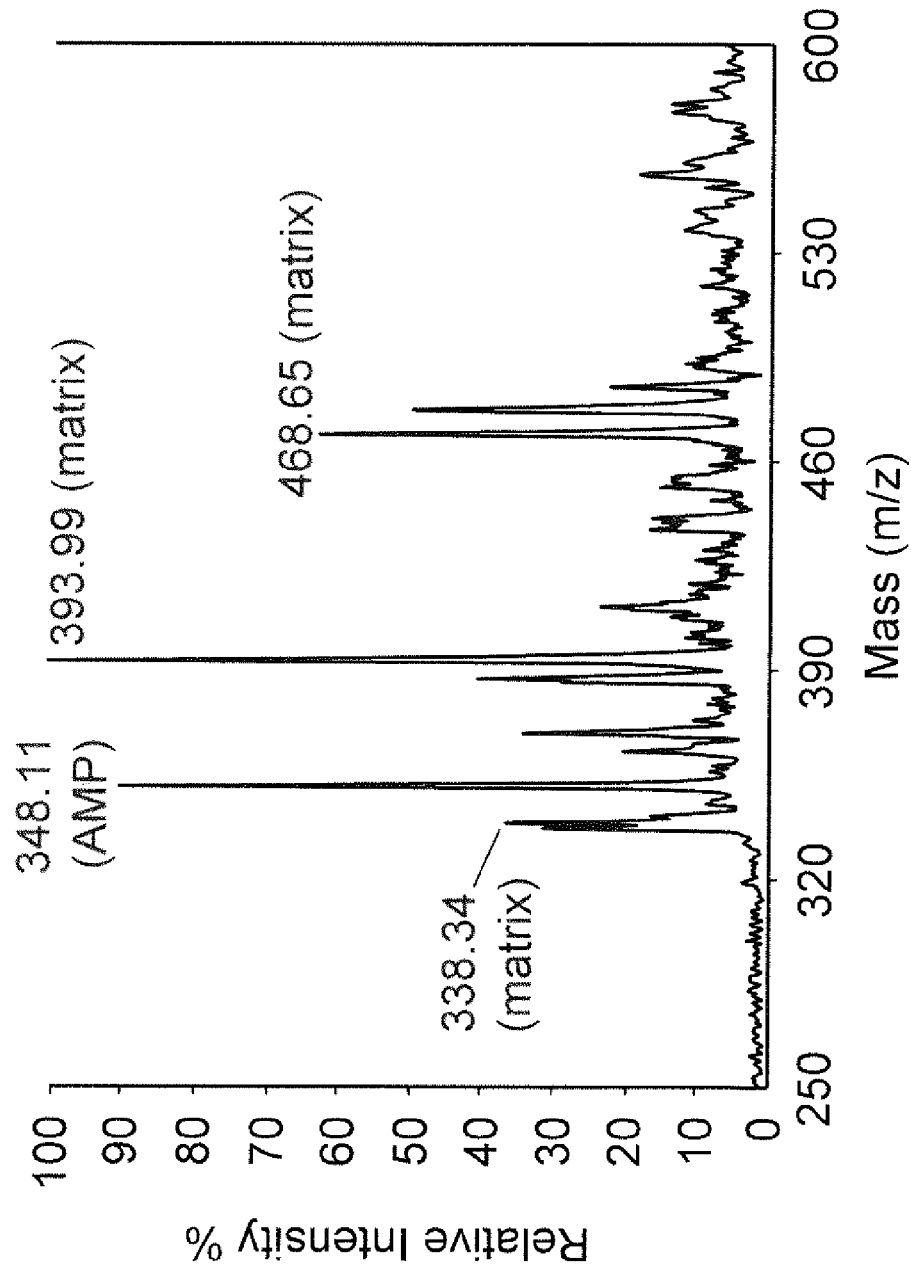

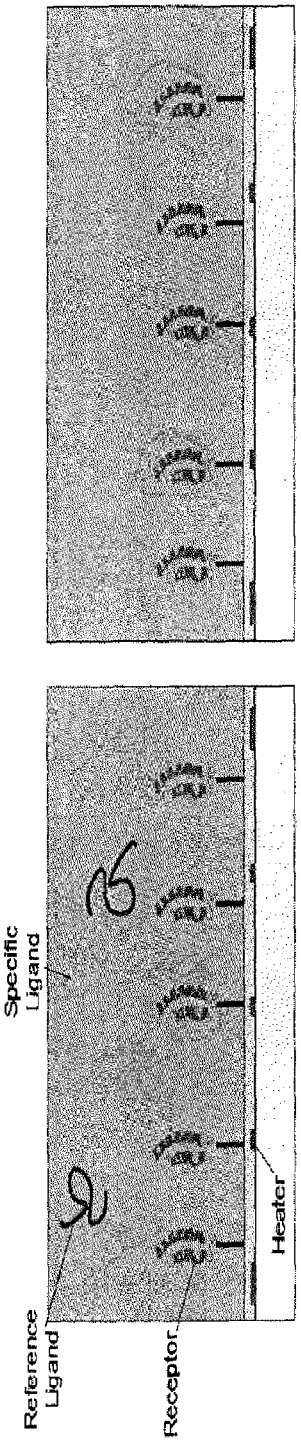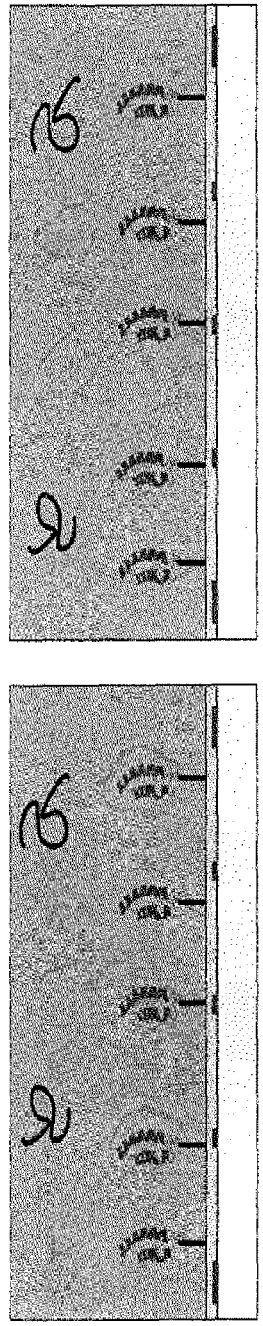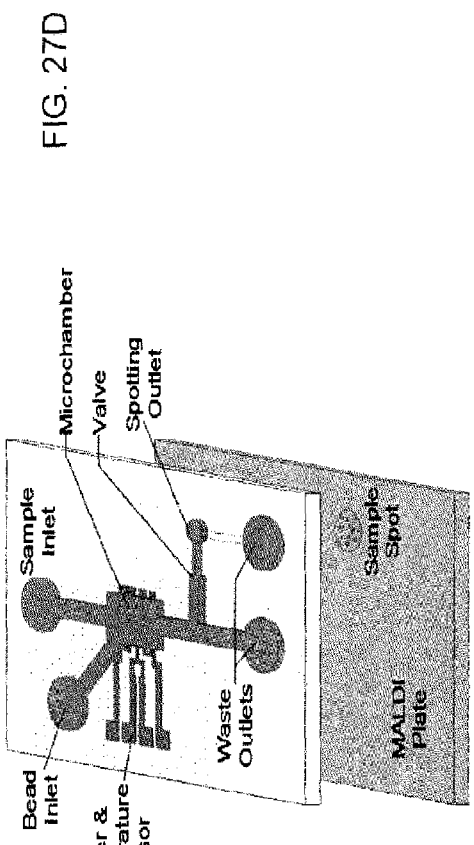
FIG. 27A
FIG. 27B
FIG. 27C
FIG. 27D
FIG. 27E

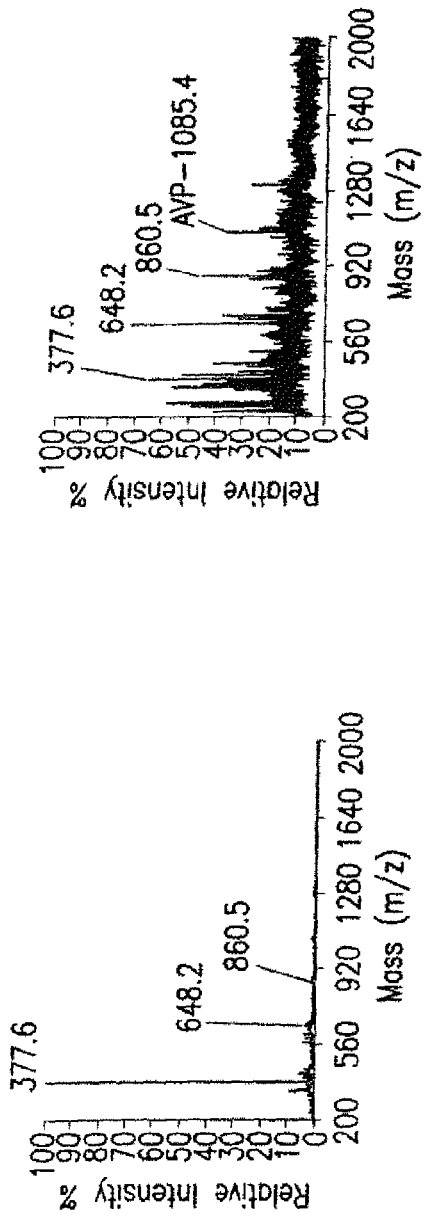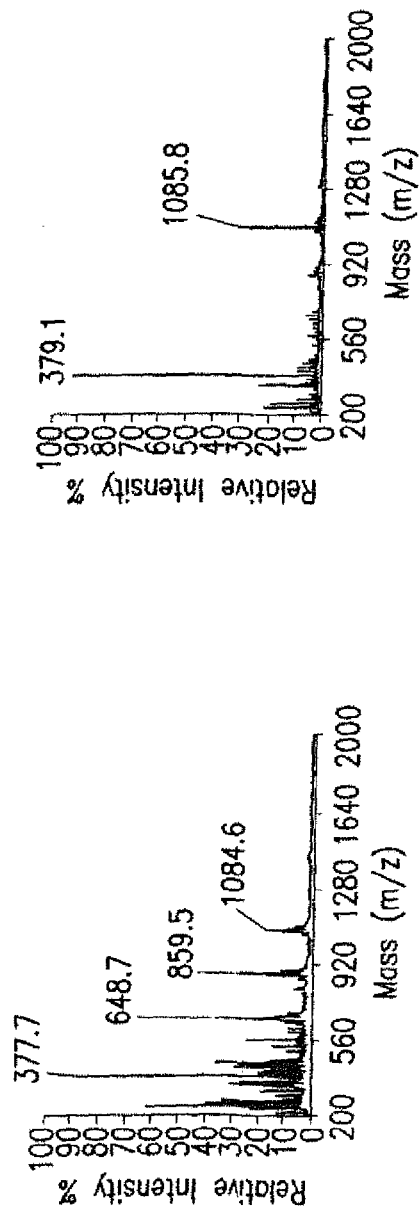
FIG. 38A
FIG. 38B
FIG. 38C
FIG. 38D

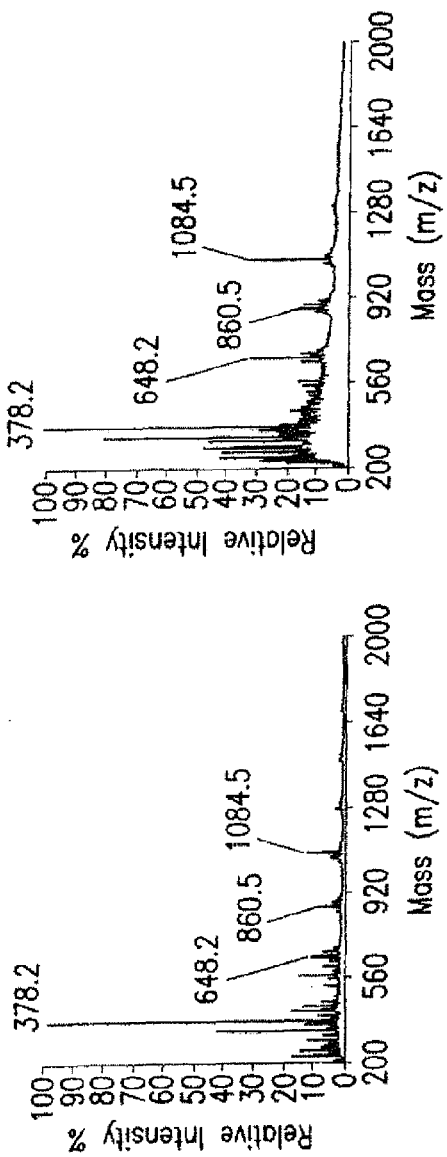
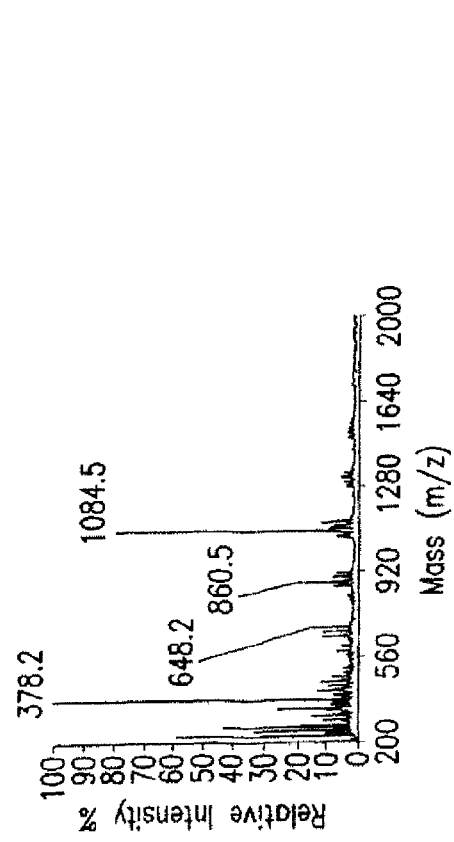
FIG. 39A
FIG. 39B
FIG. 39C

SEQUENCE LISTING

<160> NUMBER OF SEQ ID NOS: 2

<210> SEQ ID NO 1
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gggguagggc uuggaugggu aguacacgug ugcguggu                              38

<210> SEQ ID NO 2
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2 gggguugggaa gaaacugugg cacuucggug ccagcaaccc                           40

SELECTIVE CAPTURE AND RELEASE OF ANALYTES

CROSS-REFERENCES TO RELATED APPLICATIONS

This application is a divisional application of U.S. application Ser. No. 12/568,651, filed Sep. 28, 2009, which is a continuation-in-part of International Application Serial No. PCT/US08/058,433 filed on Mar. 27, 2008, which claims priority to U.S. Provisional Application Nos. 60/908,298, filed Mar. 27, 2007; 60/908,304, filed Mar. 27, 2007; 60/968,803, filed Aug. 29, 2007; 60/972,061, filed Sep. 13, 2007; 60/987,474, filed Nov. 13, 2007; 60/989,182, filed Nov. 20, 2007, and also claims priority to U.S. Provisional Application Ser. Nos. 61/165,690, filed Apr. 1, 2009, and 61/171,333, filed Apr. 21, 2009, the disclosures of all of which are incorporated by reference in their entireties.

STATEMENT REGARDING FEDERALLY SPONSORED RESEARCH

This invention was made with government support under Grant Nos. CBET-0693274 and EIA-324845 awarded by The National Science Foundation. The government has certain rights in the invention.

SEQUENCE LISTING

The specification further incorporates by reference the Sequence Listing submitted herewith via EFS on Oct. 8, 2013. Pursuant to 37 C.F.R. §1.52(e)(5), the Sequence Listing text file, identified as 070050_4716_SL.txt, is 1,214 bytes and was created on Aug. 22, 2013. The Sequence Listing, electronically filed herewith, does not extend beyond the scope of the specification and thus does not contain new matter.

BACKGROUND

The present application relates to, but is not limited to, selective capture and release of analytes. For example, the present application relates to minimally invasive extraction, purification and concentration (PC) of analytes.

A need exists for techniques to selectively capture and release analytes with minimal harm to the analytes. For example, such techniques are applicable to extraction of analytes for biochemical analysis. Other applications include detection of harmful components in pharmaceuticals or food, extraction of harmful environmental agents, selective release of drugs at a target location in the body, and the like.

As an example, there is a desire to develop highly integrated biological analysis devices that can be used to perform general biochemical analysis. One component in these devices is sample preparation, which involves extraction and PC of applicable analytes.

Some techniques have employed solid-phase (SP) gels for retention of target molecules. A common shortcoming of SP devices is that their capture mechanisms are often indiscriminate with respect to the target analyte. For example, hydrophobic and ion-exchange SP device are limited because they extract impure compounds with similar physical or chemical properties as the target. With applications in drug delivery or chemical assays, where specific molecules need to be released, introducing impurities can be problematic. In addition, elution of molecules using harsh pH or solvent gradients is common in SP devices. For certain biomedical applications, these elution schemes can present potential health hazards. Furthermore, it is desirable to selectively release the captured molecules for applications in which their use is location-specific.

Biotechnology research, such as proteomics and genomics, utilizes biological mass spectrometry, which is label-free and offers increased resolution detection. In particular, matrix assisted laser desorption/ionization mass spectrometry (MALDI-MS) is useful because it permits relatively simple data interpretation, good detection limits and parallel processing. MALDI-MS is based on a soft ionization technique in which analytes are cocrystallized with an energy-absorbing matrix material on the surface of a substrate (called a MALDI analysis plate). Notwithstanding its broad utility, the overall quality and efficacy of quantifiable MALDI-MS generally depends on the purity of the introduced sample. Techniques involving sample preparation, such as analyte extraction, have increasingly been employed to condition biological samples prior to MALDI-MS analysis. This can entail the separation, purification and concentration of analytes preceding quantitative analysis. For example, analyte extraction can be used to retrieve and isolate a rare analyte from a complex mixture of undesirable constituents such as salts, particulates, solvents or physiological tissue so as to enrich and enhance the analyte's MALDI-MS detection.

Solid-phase extraction (SPE) as a sample preparation procedure prior to MALDI-MS that can be used to provide pure and concentrated samples to enable increased sensitivity analysis. During SPE, an analyte of interest within a fluid phase is exposed to a solid phase (e.g., microbeads coated with a thin layer of a functional material). The analyte interacts through surface chemistry with the coating and therefore is retained by the solid phase. This allows impurities and non-target compounds remaining in the liquid phase to be removed by rinsing. Next, a reagent (such as an organic solvent) is generally used to disrupt the interaction between the solid phase and the analyte, thereby eluting the analyte for further analysis. Other sample preparation techniques include electrokinetic sample stacking, liquid-liquid extraction, and dialysis. The off-line nature of MALDI-MS makes it suitable for coupling to off-line SPE approaches, which facilitate high-throughput processing designs with small dead volumes.

In some SPE protocols, one challenge is to effectively concentrate and purify minute quantities of analytes, while minimizing absorptive losses and maximizing recovery in as compact an elution volume as possible. Microfluidic technology has been utilized to attempt to overcome this obstacle. Miniaturization helps facilitate the handling of limited sample quantities, the reduction of dead volumes, an increase the effective surface-to-volume ratio to promote efficient chemical reactions, and integration. Also, microfabrication allows for massive parallelization of sample processing, while being amenable to MALDI-MS which can lower analysis costs. Existing microfluidic SPE devices utilize physisorption capture of the target analyte by gels or membranes. For example, some techniques use a commercial reversed-phase gel (Poros) on some microfabricated silicon chips for sample enrichment of alcohol dehydrogenase. The proteins are eluted by addition of a polar solvent (e.g., acetonitrile), which changes the surface polarity of the support to release the bound analyte. Ion-exchange supports, such as some methacrylate based gels, depend on adjustment of charged molecules on the retention media to interact with analytes. Strong pH reagents can be introduced to subsequently release the molecules of interest. Alternatively, other techniques use a packed 2.5 mm column of C18 microbeads for the reversephased preconcentration of ephedrine on a poly (vinylpyrrolidone) chip which is then eluted using an acetonitrile-borate buffer solution.

Existing microfluidic SPE devices, however, remain inadequate to address the current demands in MALDI-MS analysis, which increasingly requires processing of complex biological or chemical samples, such as blood, serum, or tissue mass. A given analyte should be detectable amongst cellular debris, non-specific molecules, and salts within such samples. Standard functional chemistries for solid-phase purification often lack selectivity to target analytes since impurities usually exhibit similar physical properties (e.g., hydrophobicity or ionic charge) which allow their simultaneous retention. For unambiguous, sensitive detection of biomolecules by MALDI-MS, it is useful that the analyte extraction be specific, e.g., the analyte and no impurities are retained by the solid phase. Moreover, recovery of biomolecules using traditional techniques generally requires an adjustment in pH or application of a solvent gradient. This can compromise the integrity of sensitive compounds (which can already be in rare supply) and can further complicate the protocol by requiring the handling of potentially harsh reagents.

Biosensors are used for the detection and analysis of biomolecules that are disease relevant biomarkers such as genes, proteins, and peptides. They can include of a molecular recognition component and a transducer converting the binding event into a measurable physical signal. An important class of biosensors includes affinity biosensors, which rely on highly selective affinity receptors recognizing target biomolecules. Traditionally used affinity receptors include antibodies and enzymes, which are known to have limitations such as instability, poor regeneration, and physiologically-dependent production. These limitations can be addressed by biosensors that employ alternative, synthetically generated affinity receptors, in particular aptamers.

Aptamers include oligonucleotides that recognize target molecules specifically by highly selective affinity interaction; they are isolated through a synthetic procedure called systematic evolution of ligands by exponential enrichment (SELEX), whereby very large populations of random sequence oligomers (DNA or RNA libraries) are screened against the target molecule in an iterative procedure. Aptamers have been developed to target a variety of biomolecules (e.g., small molecules, peptides, and proteins) in diverse applications, such as target validation, drug discovery, and in particular, diagnostics and therapy. The intense attention received by aptamers can be attributed not only to their high specificity, but also to characteristics that are lacking in more established affinity receptors such as enzymes, lectins, and antibodies. These include enhanced stability at room temperature, and more easily modified terminal ends, as compared to their conventional affinity receptor counterparts (e.g., antibodies and enzymes), so as to facilitate attachment to stationary surfaces. Moreover, aptamer-target binding is generally reversible under changes in environmental parameters such as pH and temperature. Thus, aptasensors can be regenerated via such experimental stimuli, which can also be exploited to allow controlled release and recovery of target biomolecules.

Microelectromechanical systems (MEMS) have been applied to biosensing, leading to minimized sample consumption, improved robustness and reliability, reduced costs, and the possibility of parallelized, high-throughput operation. In particular, microfluidic devices have been used for affinity biosensing, such as microcantilever immunosensors for myoglobin and nanoparticle-antibody conjugated array sensors for detecting food-born *Escherichia coli*. Microcantiliever aptasensors have been used for specific detection of *Thermus aquaticus* DNA polymerase. Biomolecules are detected after binding by monitoring surface stress induced deflection of the cantilever by an interrogating light source. Alternatively, love-wave microfluidic aptasensors have been used to detect multifunctional serine protease thrombin and Rev peptide, fabricated from polymethylmethacrylate on top of a quartz substrate. Nanostructures such as single-walled carbon nanotubes have been functionalized with aptamers to detect thrombin. The selectivity of the thrombin aptamer has been tested against elastase to which the conductance of the SWNT-FET showed no change.

Aptasensing of arginine vasopressin (AVP) for the diagnosis and therapy of septic shock (induced by severe infection) and congestive heart failure, conditions that restrict the cardiovascular system's ability to provide adequate perfusion in order to maintain organ functionality is a clinical application of aptasensors. Both disorders are indicated by elevated levels of AVP, a cyclic polypeptide neurohormone that is synthesized in the hypothalamus and promotes vasoconstriction. Specifically, physiological concentrations of AVP in plasma markedly increases up to tenfold that of average levels (5-10 pM) in order to maintain arterial pressure and hence, blood perfusion. As shock progresses however, the initial abundance of AVP in plasma decreases. Thus, the ability to monitor and control AVP over time can reveal the homeostatic status of the patient, and could potentially provide therapeutic solutions for septic shock and congestive heart failure. Platforms for vasopressin include immunoradiometric assays (IRA) and enzyme-linked immunosorbent assays (ELISA). The use of these assays is often hindered by several limitations: time-consuming and complicated radio and fluorescent labeling protocols; excessive use of sample and auxiliary reagents; and limited long-term stability and shelf-life. Moreover, prolonged incubation times can result in slow diagnostic turnaround (3-11 days), which renders these techniques rather ineffective for therapeutic management of AVP.

SUMMARY

Systems and methods for selective capture and release of analytes are disclosed herein.

Some embodiments include components for capture and selective release of an analyte. In an exemplary apparatus, a system includes a solid phase, an aptamer functionalized on the solid phase for binding the analyte, and a temperature regulator for setting a temperature to a set point, such that the analyte is released from the aptamer at the set point. The analyte can initially exist in an impure form and the impurities can be removed with a washing solution after the analyte is bound to the aptamer. The analyte can include a peptide, protein, small molecule or live cell. The solid phase can include a microbead. The analyte can be in an aqueous solution.

The system can further include a collector for collecting the released analyte; and a detector for measuring the amount of analyte released. The collector can include a spotting well. The detector can be a mass spectrometer. The components can further include a microchannel for receiving the released analyte and directing the released analyte through a hydrophobic valve. These components can be incorporated on a microfluidic chip platform.

Techniques for capturing and selectively releasing an analyte are also provided. In some embodiments, the techniques include binding the analyte to an aptamer, the aptamer functionalized on a solid phase, and setting the temperature of the aptamer such that the analyte is released from the aptamer. The procedure can further include introducing the analyte to the aptamer in an impure form and washing the bound aptamer analyte complex to remove impurities. The procedural elements can be repeated so that the amount of bound analyte is increased. The procedure can further include collecting and detecting the analyte. The detecting can include performing mass spectrometry on the released analyte or detecting fluorescence intensity.

Techniques for selectively increasing the concentration of an analyte are also provided. In some embodiments, the techniques include functionalizing a solid phase with an aptamer, introducing the analyte to the aptamer in an impure form, binding the analyte to the aptamer, and washing the bound aptamer analyte complex to remove impurities. The procedural elements can be repeated so until a desired analyte concentration is reached, and the temperature of the aptamer can be set such that the analyte is released from the aptamer.

BRIEF DESCRIPTION OF THE DRAWINGS

The accompanying drawings, which are incorporated into and constitute part of this disclosure, illustrate preferred embodiments of the described subject matter and serve to explain the principles of the described subject matter.

FIG. 4(a) shows concentration of an analyte using consecutive injections of a 200 nM dilute solution, while FIG. 4(b) shows concentration of an analyte using consecutive injections of a 500 nM injections.

FIG. 6 depicts extraction of AMP after release at (a) 75° C., (b) 85° C., and (c) 95° C. according to exemplary embodiments of the described subject matter.

FIGS. 7(a)-(b) depict (a) chemical structure of bio-ATP-40-1 aptamer (SEQ ID NO: 2) and (b) molecular structure of TO-AMP according to exemplary embodiments of the described subject matter.

FIGS. 13(a)-(b) depict controlled release of TO-ATP and regeneration of an exemplary SPE device of the described subject matter (baseline colinear w/horizontal axis). FIG. 13(a) shows competitive displacement with ATP (800 µM & 3.2 mM). FIG. 13(b) presents thermally induced release and regeneration. Single-valued points are obtained similarly to time-resolved data.

FIG. 14(a) is an isometric view. FIG. 14(b) is an A-A' cross-sectional view. The chip dimensions are 3.5×2.5×0.5 cm (l×w×h).

FIGS. 15(a)-(e) depict a simplified device fabrication flow example according to an embodiment of the described subject matter. FIGS. 15(a-c) depict a microchannel and integrated heater and temperature sensor elements realized with standard soft lithography and MEMS fabrication techniques; FIGS. 15 (d & e) depict device packaging according to exemplary embodiments of the described subject matter.

FIGS. 18(a)-(c) depict MS from (b) a 0.1 µM injected sample and (c) a 1.0 µM injected sample according to exemplary embodiments of the described subject matter.

FIGS. 20(a)-(d) depict MS from a sample spot obtained from (b) 25 injections; (c) 250 injections of 10 nM AMP solution according to exemplary embodiments of the described subject matter.

FIGS. 22(a)-(h) depict an exemplary device fabrication flow according to an embodiment of the described subject matter as seen from cross-section A-A in FIG. 21a: (a-c) depicts SU-8 patterning followed by subsequent PDMS prepolymer casting to form microfluidic layers; (d) depicts glass substrate drilled for fluidic interconnects; (e) depicts thermal evaporation and lift-off patterning of Cr/Au bi-layer; (1) depicts PECVD deposition of $SiO_2$ passivation layer; (g)

depicts microfluidic structural layers aligned and permanently bonded to the glass substrate; (h) depicts packaged chip with tubing.

Figure 23A:
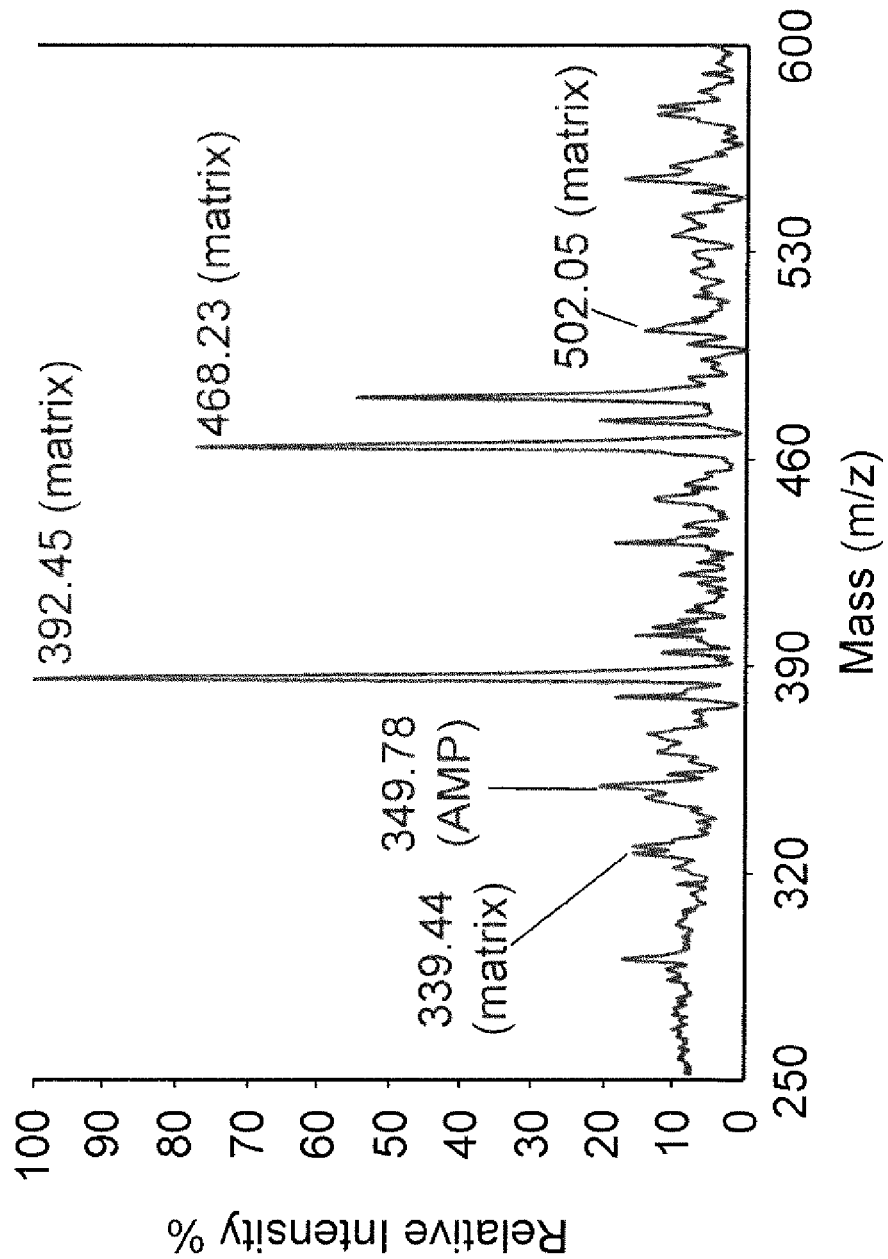
Figure 23C:
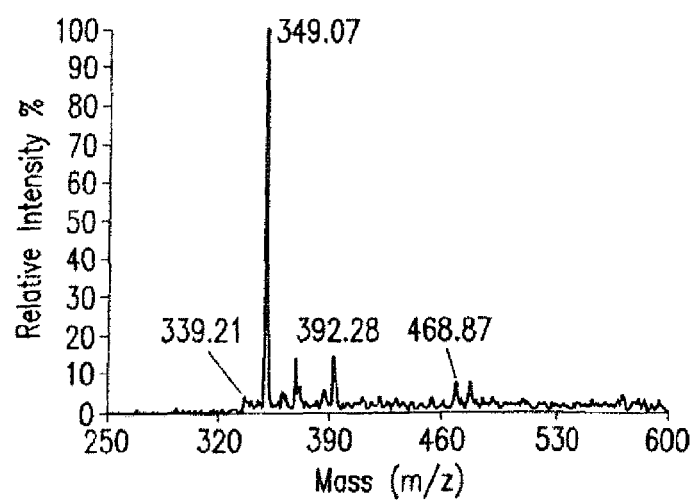

FIGS. 23(a)-(c) depict MALDI-MS detection of varying concentrations of AMP in a pure water solution using an ATP-aptamer functionalized microchip coupled to a MALDI analysis plate according to an embodiment of the described subject matter. (a) depicts demonstrations using 10 nM, (b) 100 nM and (c) 1 µM.

Figure 24A:
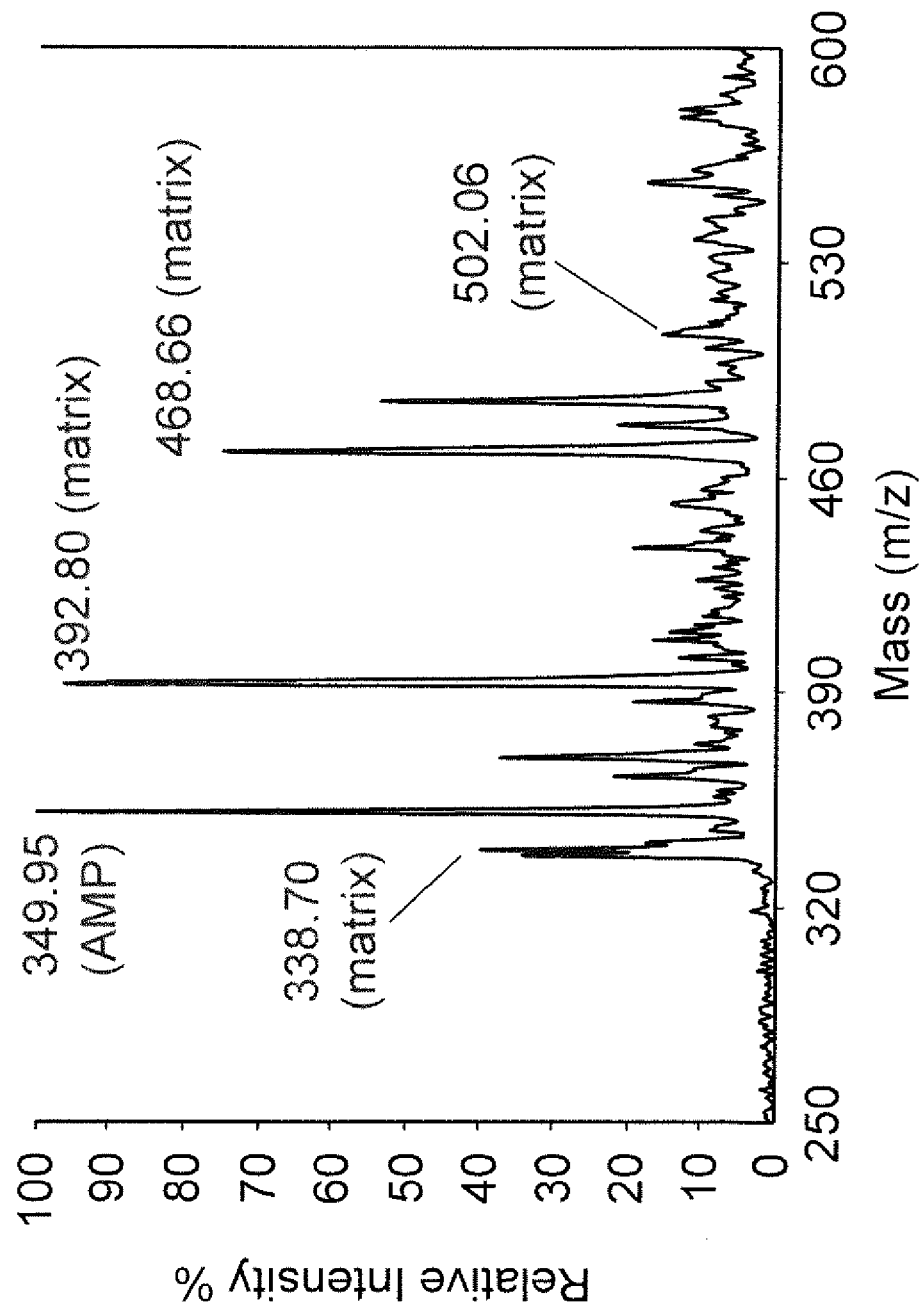
Figure 24B:
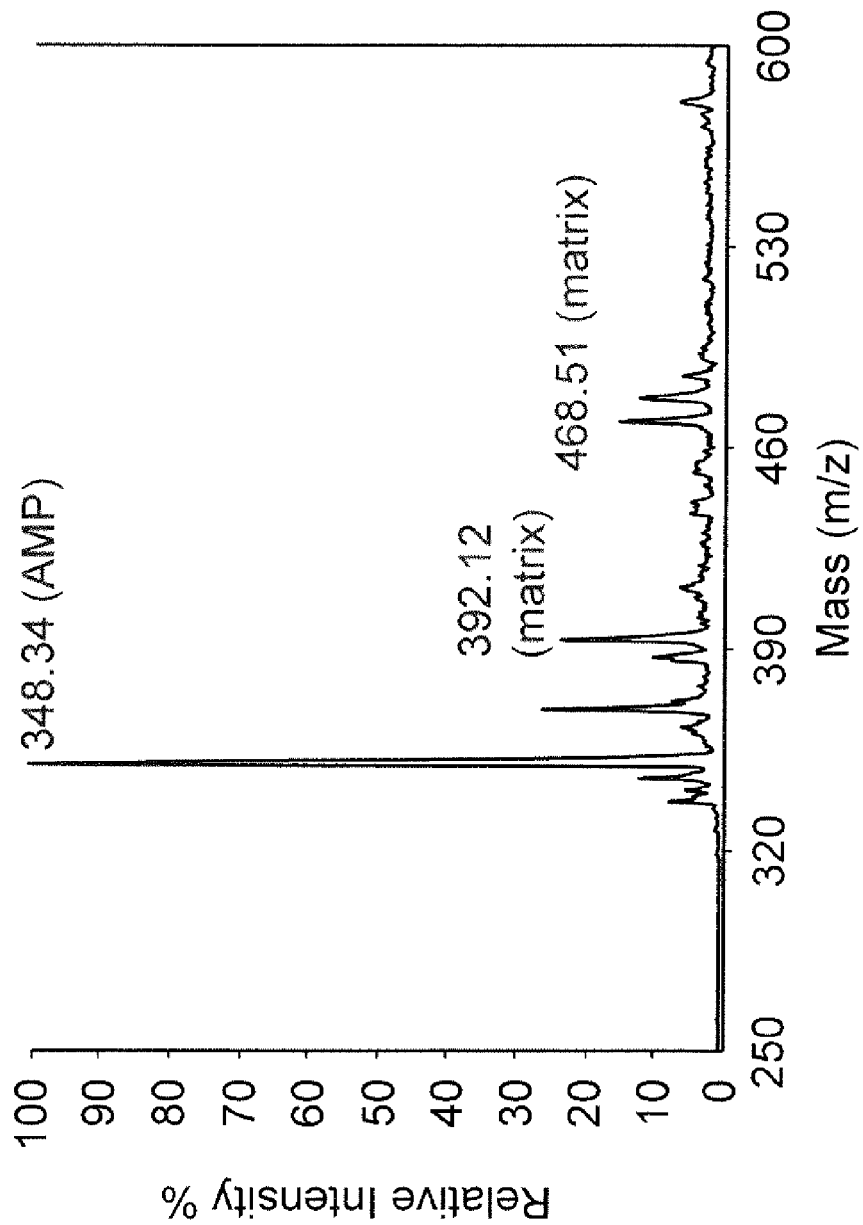

FIGS. 24(a)-(b) depict Discrete concentration after 25 (a) and 250 (b) infusions of a 10 nM AMP sample revealing detection enhancement by aptamer-based enrichment according to an embodiment of the described subject matter.

Figure 25A:
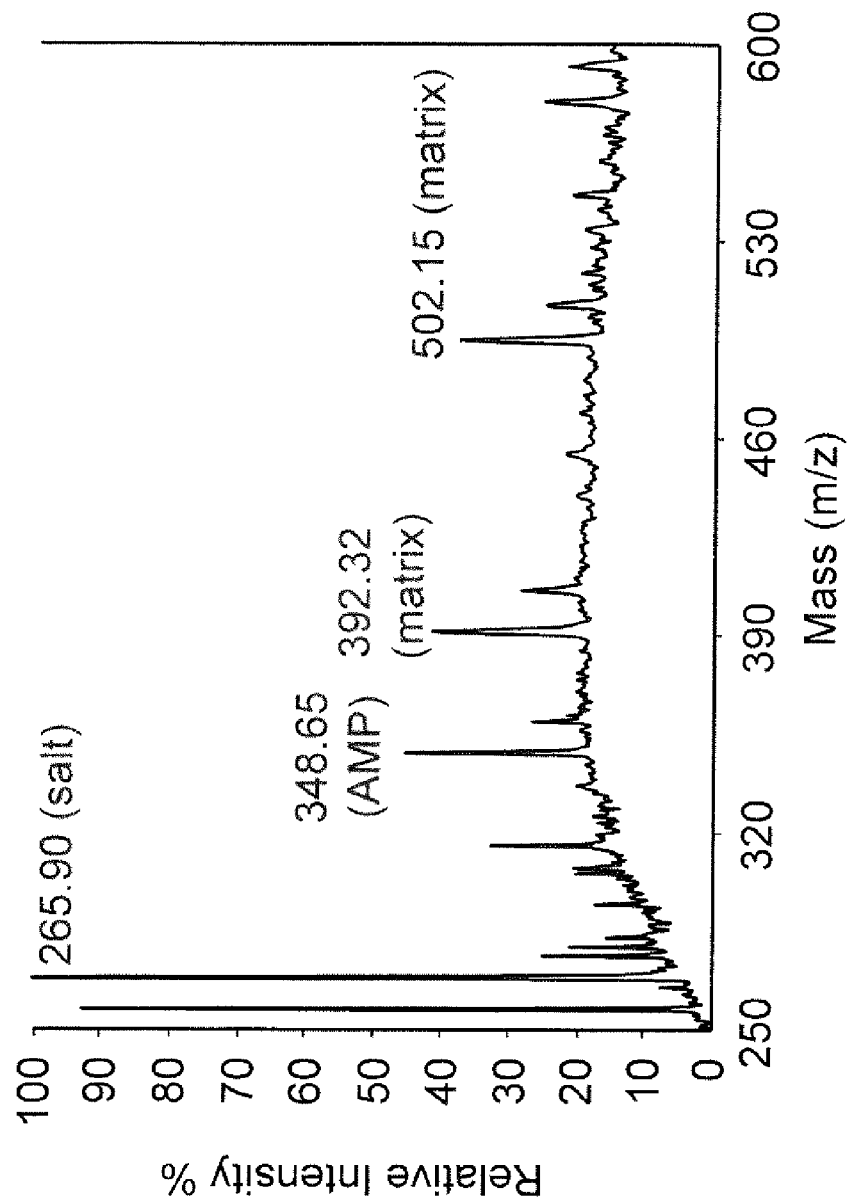
Figure 25B:
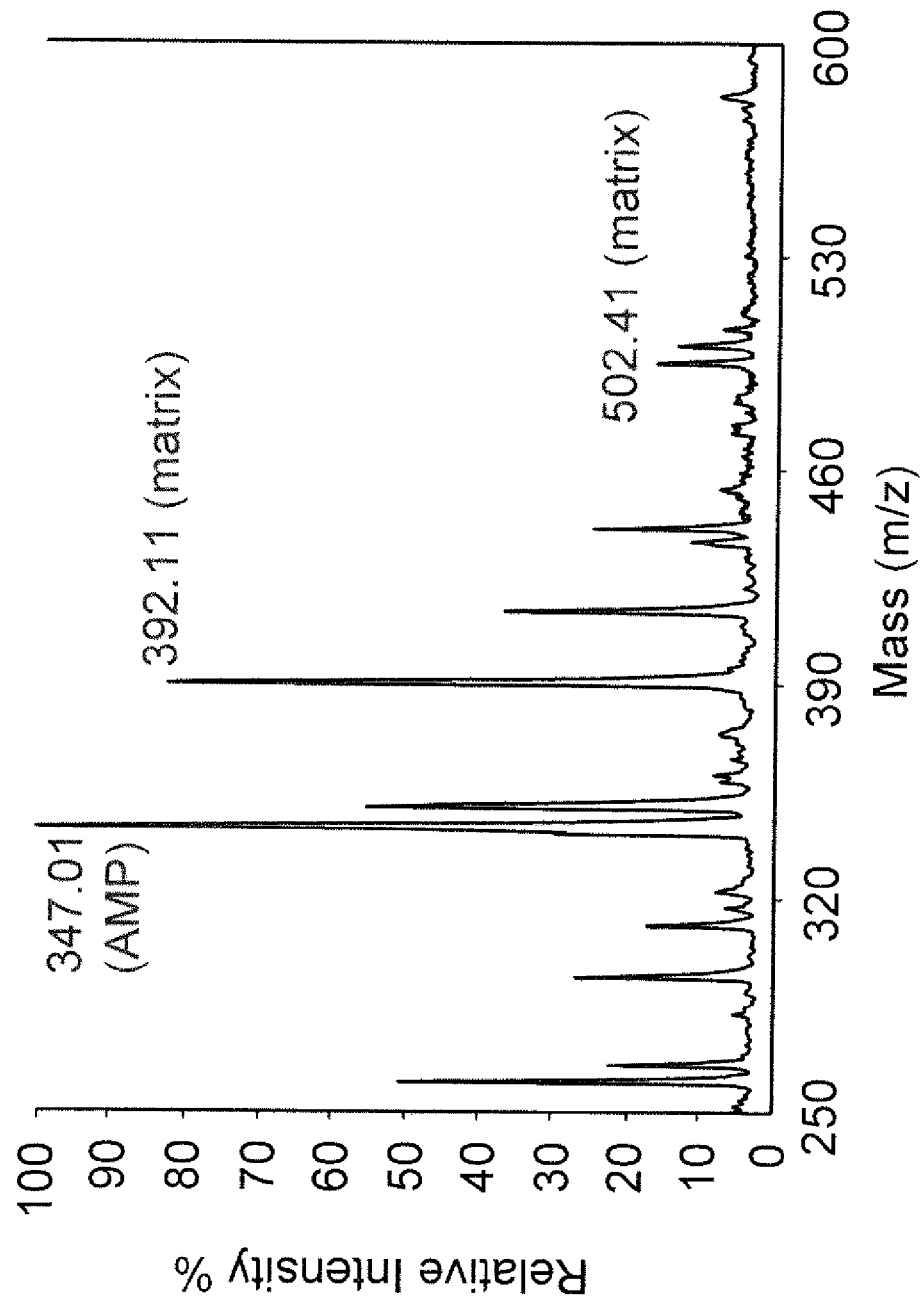

FIGS. 25(a)-(b) depict demonstration of the sample cleanup of a model analyte apparatus before MALDI-MS detection according to an embodiment of the described subject matter (a) MALDI spectrum of AMP (100 nM) in the presence of model impurity analytes (CTP, UTP, and GTP, all 1.0 µM) and (b) MALDI spectrum of AMP in the presence of model impurities after cleanup using the aptamer-functionalized microchip device.

Figure 26A:
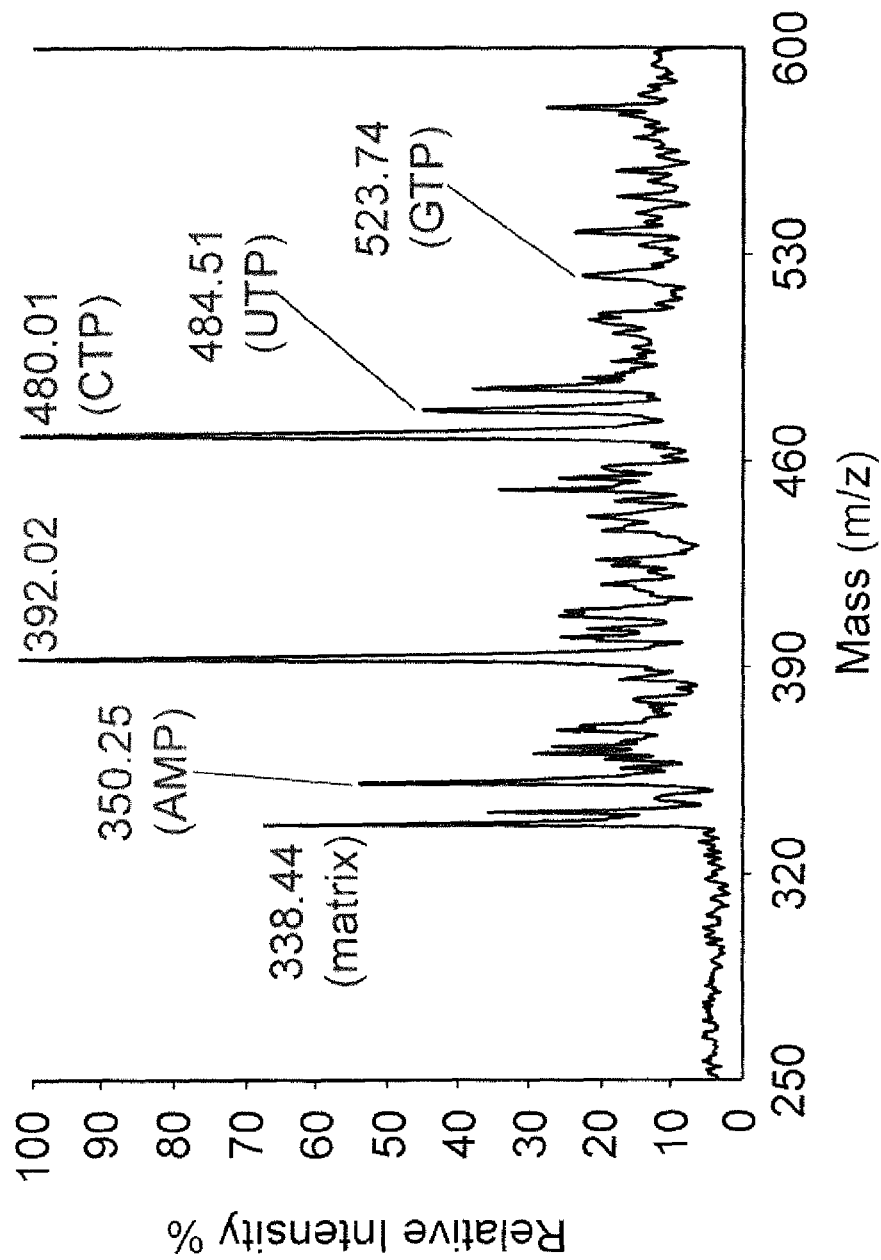
Figure 26B:
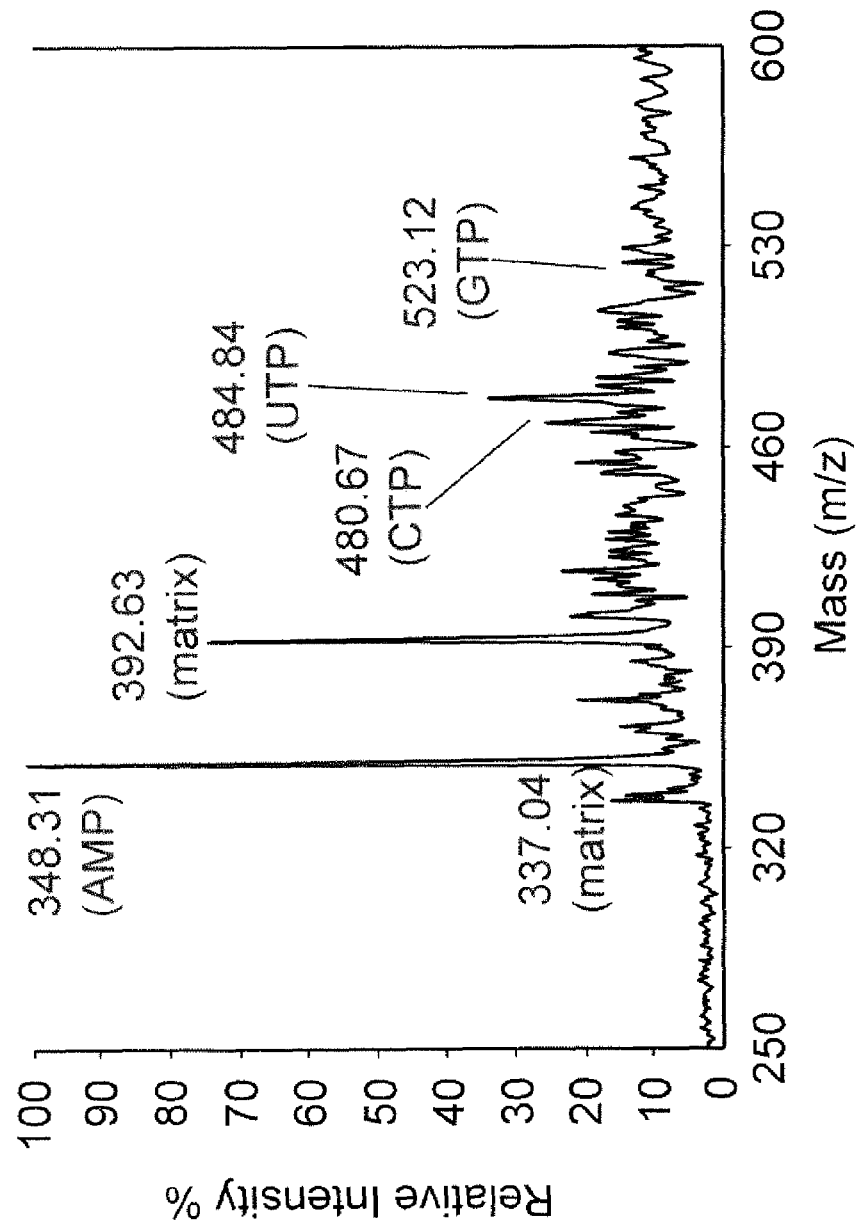

FIGS. 26(a)-(b) depict purifying AMP (100 nM) from a salt-contaminated buffer solution for enhanced MALDI-MS detection according to an embodiment of the described subject matter. (a) depicts a spectrum of sample prior to purification using the microchip. (b) depicts a spectrum obtained after sample purification using an aptamer-functionalized microchip.

FIGS. 27(a)-(e) illustrate examples incorporating the principle of microfluidic characterization of temperature dependent biomolecular binding: (a) A sample of specific and nonspecific reference ligands are introduced to a receptor functionalized solid surface. (b) After incubation at a selected temperature (controlled by integrated heaters on the surface), a certain amount of specific ligands bind to the receptor leaving unbound ligands and the reference ligands in solution. (c) Similarly, a sample of specific ligands previously bound to the receptor surface can be released (d) following modification of the surface temperature above or below a binding temperature. (e) The sample is transferred from the surfaces to the MALDI plate, via an integrated microdevice, for MS analysis.

Figure 28:
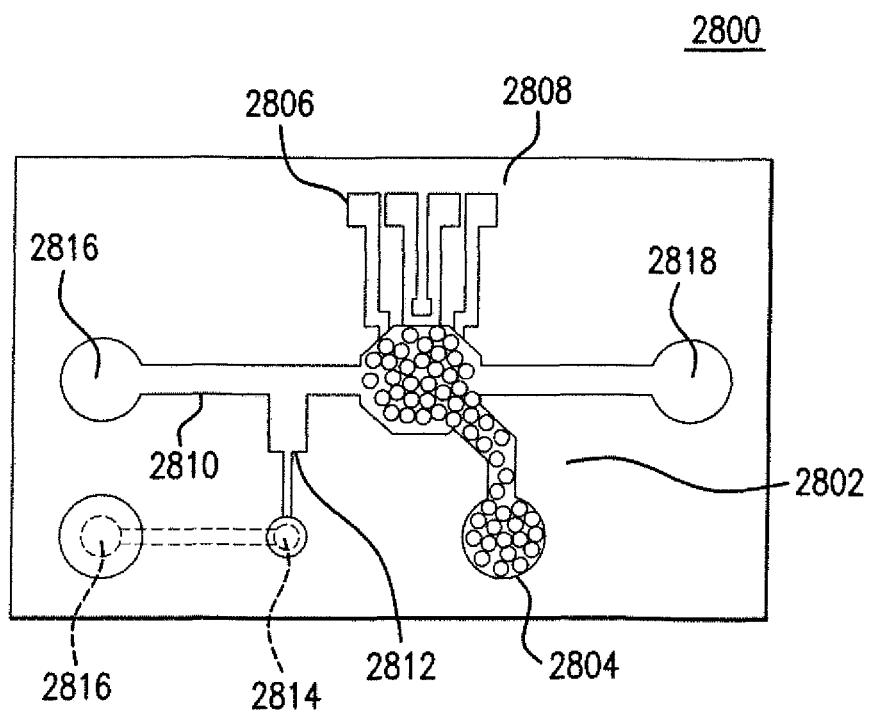

FIG. 28 depicts a schematic of the microfluidic device of an example embodiment used for MALDI-MS based characterization of temperature dependent aptamer-protein binding.

Figure 29:
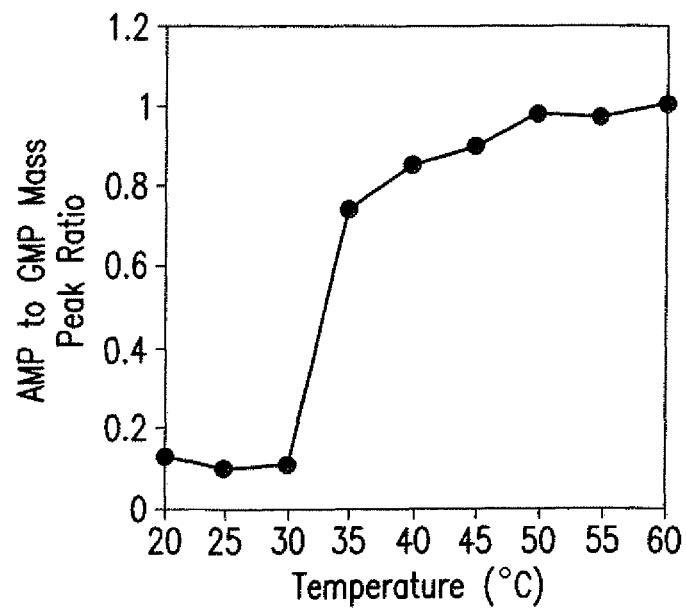

FIG. 29 depicts temperature dependent binding of AMP to anti-AMP aptamer according to an embodiment of the described subject matter. GMP standard is of equal concentration to AMP for each sample.

Figure 30:
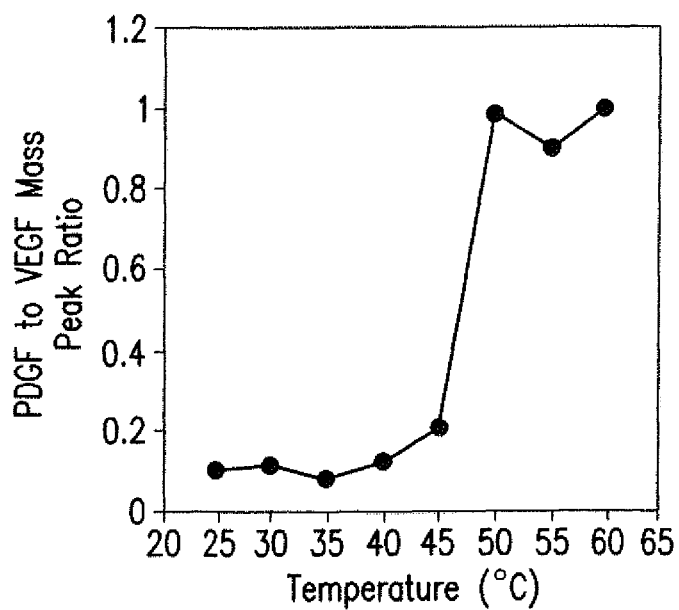

FIG. 30 depicts temperature dependent binding of PDGF to anti-PDGF aptamer obtained similarly to the protocol used for the AMP device according to an embodiment of the described subject matter. VEGF utilized as a standard.

Figure 31:
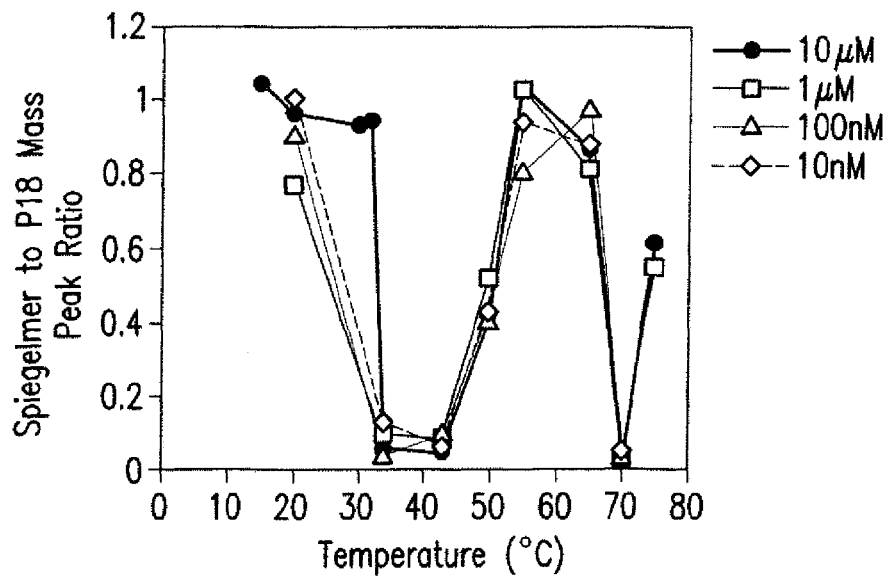

FIG. 31 depicts temperature dependent binding of spiegelmer-vasopressin according to an embodiment of the described subject matter. P18 standard is of equal concentration to the spiegelmer for each sample.

Figure 32A:
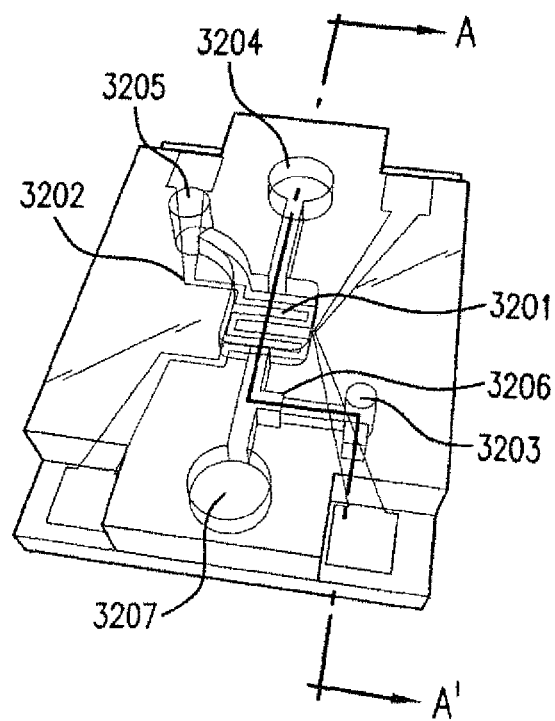
Figure 32B:
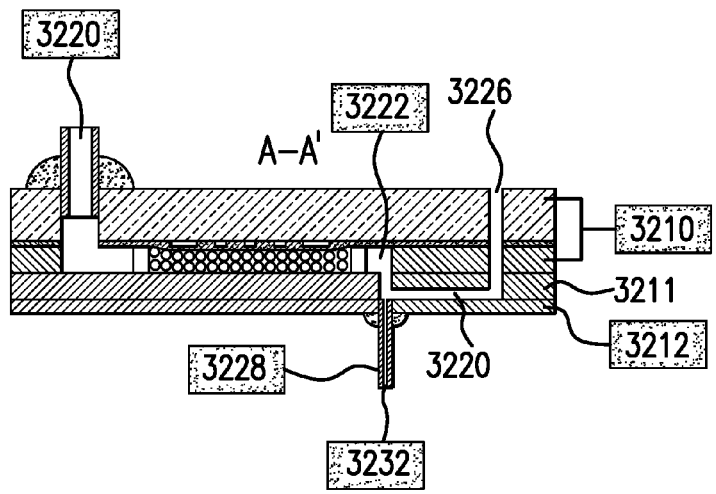
Figure 32C:
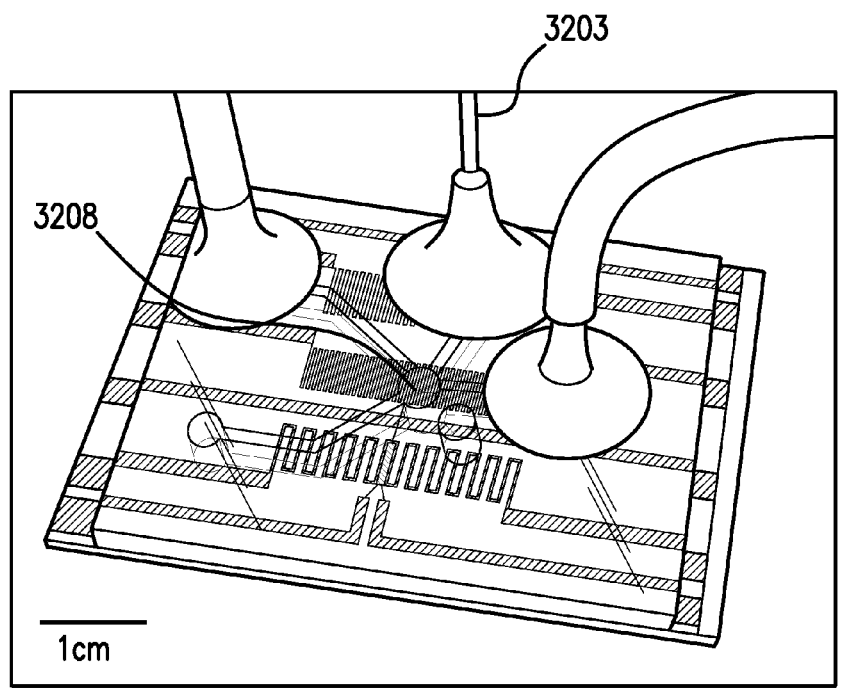

FIGS. 32(a)-(c) depict (a) a schematic of the microfluidic aptasensor of an embodiment of the described subject matter; (b) a cross-sectional view along line A A' from (a) illustrating the device's layered structure; (c) A photograph of a packaged device of an embodiment of the described subject matter.

Figure 33:
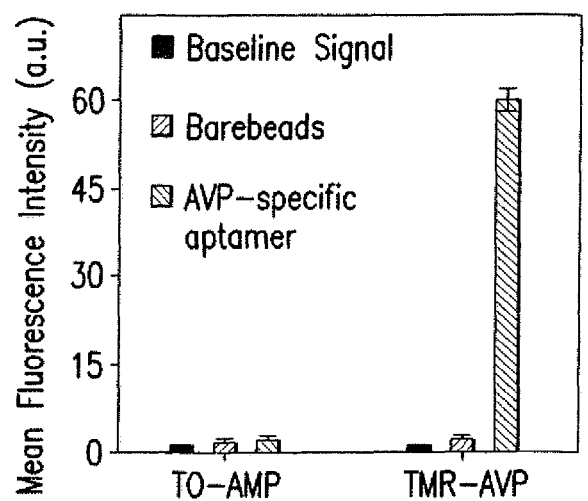

FIG. 33 depicts example demonstrations for illustrating the described subject matter; 1 µM sample of TMR-AVP and TO-AMP are introduced into the aptasensor microchamber containing bare beads and then subsequently AVP-specific aptamer.

Figure 34:
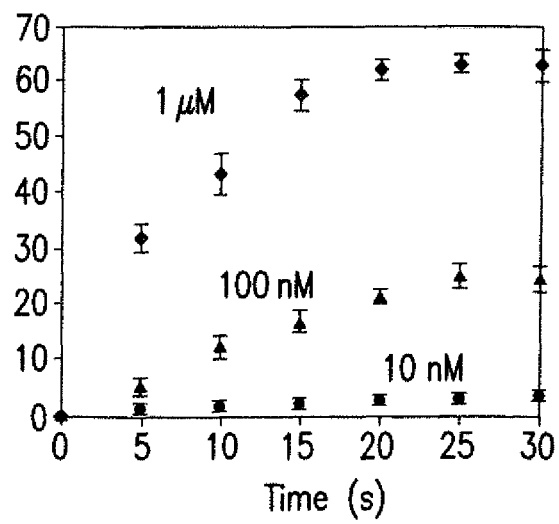

FIG. 34 depicts time resolved fluorescence measurements for the binding of TMR-AVP to the aptamer for an embodiment of the described subject matter.

Figure 35:
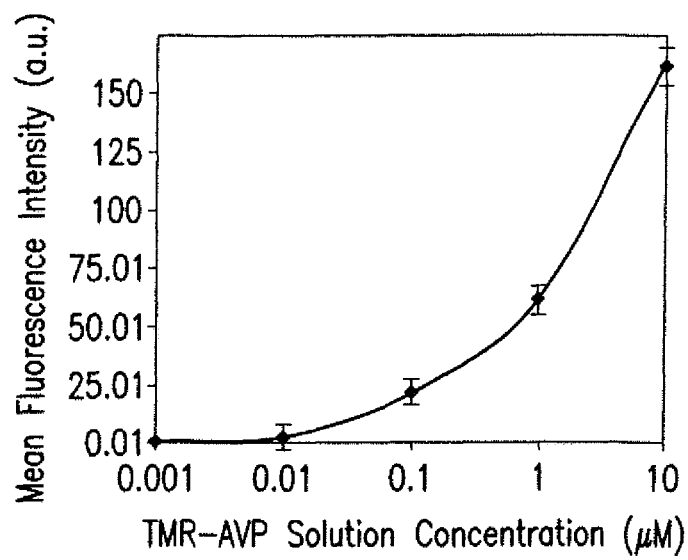

FIG. 35 depicts concentration dependent fluorescence response of TMR-AVP at varying concentrations. A sample was injected into and incubated in the extraction chamber. At this point, TMR emission is measured from the objective lens and recorded. A dose dependent relationship is observed.

Figure 36:
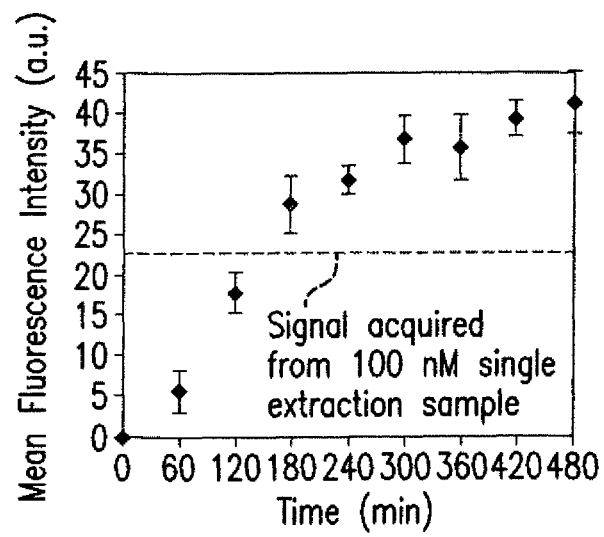

FIG. 36 depicts enrichment by continuous infusion of a dilute sample (100 pM) of TMR-AVP according to an embodiment of the described subject matter. The red dashed line indicates the relative fluorescence of a 100 nM sample. This demonstration highlights the capability of enrichment prior to detection for enhanced signal acquisition.

Figure 37:
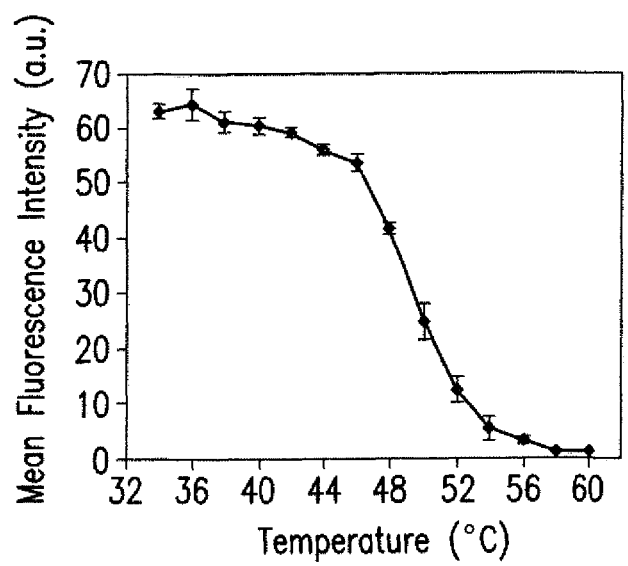

FIG. 37 depicts thermally activated release of captured TMR-AVP according to an embodiment of the described subject matter. An initial 1 µM sample of TMR AVP is captured from solution at ~35° C. Subsequently, the temperature is raised incrementally while introducing pure AVP-buffer. The initiation of a sharp decrease in signal at ~46° C. can be observed, continuing to vanish as the temperature increases, demonstrating release of the TMR-AVP from the aptamer.

FIGS. 38(a)-(d) illustrate detection of unlabeled AVP using an aptasensor of an embodiment of the described subject matter. A sample of AVP is introduced into the aptasensor for capture inside the microchamber, followed by thermally induced isocratic elution into a pure matrix plug that is subsequently spotted onto the MALDI plate. Mass spectra of: (a) 1 pM AVP; (b) 10 pM; (c) 100 pM; and 1 nM (d) are depicted.

FIGS. 39(a)-(c) depict enrichment of dilute AVP samples by continuous infusion of prior to MALDI-MS detection: (a) 1; (b) 10; and 100 pM (c). The ability to increase the relative signal intensity of the molecular ion peak for AVP for ultralow concentration samples demonstrates the utility of a microfluidic enrichment process of an embodiment of the described subject matter.

The presently described subject matter will now be described in detail with reference to the Figures in connection with the illustrative embodiments.

DETAILED DESCRIPTION

The described subject matter includes techniques and components for minimally invasive, selective capture and release of analytes. An aptamer is selected for its binding affinity with a particular analyte(s). The aptamer is functionalized on a solid phase, for example, microbeads, polymer monolith, microfabricated supports, etc. The analyte is allowed to bind to the aptamer, for example, in a microchamber. Once the analyte has been bound, a temperature control sets the temperature to an appropriate temperature at which the captured analyte is released.

Affinity binding includes the reaction between a ligand and a specific receptor, such as an antigen and antibody or enzyme and substrate. The strong specificity stems from the ligand and receptor being ideally suited to one another both electrostatically and spatially. Additionally, ligand and receptor binding can be reversed by such stimuli as heat and ionic strength. While antibody/lectin devices are one affinity pair, high-affinity aptamers (e.g., an oligonucleotide that binds specifically to an analyte via affinity interaction) derived from nucleic acid are drawing increased attention because they can be synthesized selectively towards any target molecule. They offer long-term stability, relatively straightforward synthesis, and the capability of modifiable end-chains to facilitate labeling or immobilization. Also, aptamers can reversibly bind to their targets within an aqueous environment, eliminating exposure of sensitive devices to harsh reagents.

In some embodiments, the analyte can exist in an impure form, i.e., mixed with one or more impurities. The techniques of the described subject matter can be used to increase the PC of the analyte. Once the analyte is allowed to bind to the aptamers functionalized on the solid phases, the components are washed to remove any excess impurities. Analytes from another impure complex are allowed to bind to the aptamers, and another washing takes place. This procedure is repeated until the desired concentration is reached. The temperature is then set such that the concentrated analyte is released.

In some embodiments, the described subject matter includes collection and detection components, for example, a surface tension-based microvalve for releasing the analyte onto a detection surface and a mass spectrometer used to measure the analyte. Other detection techniques include detectors for measuring the amount of fluorescence given off by a sample of an analyte coupled with fluorescing materials, electrospray ionization mass spectroscopy, nuclear magnetic resonance, electrochemical techniques, impedance techniques, and the like.

Furthermore, the use of selective release of the analyte from the aptamers in a minimally invasive manner allows the aptamers to be reused. Minimally invasive release also causes less harm to the analyte.

In some embodiments, the particular aptamer/analyte binding can cause an otherwise actively interactive analyte to be temporarily inactivated. The analyte can be delivered to a target location where its interactivity is desired. Selective release can then release the analyte, which can regain the analyte's original interactivity. For example, certain drugs are inactivated through aptamer binding and can be targeted to specific body locations for the drug to take effect.

Analytes include any appropriate biochemical component, biomolecule, pharmaceutical, protein, nucleotide sequence, cell, virus, compound, or the like. For example, analytes include toxic molecules, compounds, or bacteria, viruses, or the like, which can appear in pharmaceuticals, food, or the like. Principles of the described subject matter can be used to selectively capture these toxins and release the toxins in a safe environment. In other embodiments, aptamers can bind to peptides, proteins, small molecules, other inorganic and organic molecules, cells, viruses, micro organisms, and the like. It should be noted that analytes can be used beyond components merely for analytical purposes. Any suitable component which is selectively captured and released by an aptamer is encompassed within the described subject matter. For example, selective capture and targeted release of analytes can be used for drug delivery. Also, captured analytes can be permanently bound to an aptamer, such as in a technique for removing biochemical hazards from the environment. Furthermore, analytes can be inactivated when attached to an aptamer, such as in techniques for reducing the effect of harmful chemicals. Still further, analytes can have their properties changed as a result of being bound to an aptamer, thereby producing a secondary effect of the analyte as desired.

In one embodiment, the described subject matter includes a microfluidic device that accomplishes integrated, all-aqueous realization of specific extraction, concentration, and coupling to mass spectrometric detection of biomolecular analytes. The device uses an aptamer functionalized on microbeads to achieve highly selective analyte capture and concentration. By on-chip temperature control, the device makes novel use of thermally induced, reversible breakage of the analyte-aptamer complex at low temperature (38° C.) to release the captured analyte and regenerate microbead surfaces. Furthermore, using a hydrophobic microvalve, the released analyte is directly spotted onto an analysis plate for detection by MALDI-TOF mass spectrometry.

In another embodiment, a microfluidic device is used for PC and release of specific analytes. The device surfaces are functionalized with an RNA aptamer that selectively binds a target analyte. The device employs thermally induced denaturing of the aptamer for intelligent release. This occurs at 32.5° C., a safe temperature for thermally sensitive analytes and ligands functionalizing the device surface. Since denaturing the aptamer is reversible, this permits reuse. In addition, operation is simplified as analyte capture and release occur in aqueous medium without altering solvent composition or polarity. Although applicable to many analytes, we use a model analyte, adenosine monophosphate (AMP).

Figures 14A, 14B:
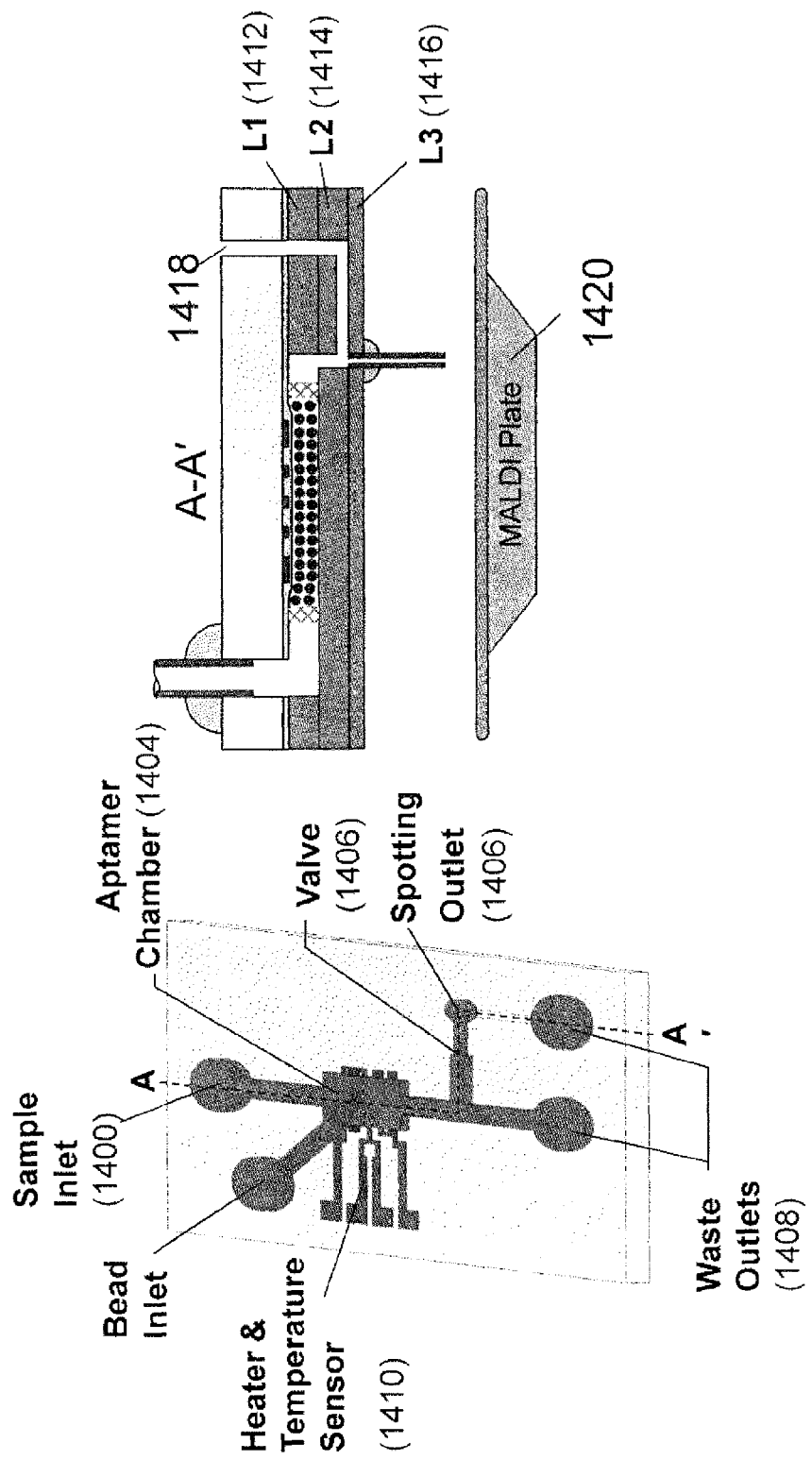
FIGS. 14(a)-(b) depict schematics of an example device according to an embodiment of the described subject matter.

In one embodiment, the device includes a microchamber packed with aptamer-immobilized microbeads for analyte PC, a microheater and temperature sensor for thermally induced analyte release, and microchannels equipped with a passive valve using surface tension for spotting the released analyte onto a MALDI analysis plate (FIGS. 14(a)-(b)). Analyte, matrix, and wash solutions are introduced via a sample inlet 1400. The bead inlet facilitates packing the aptamer chamber 1404 with microbeads. A resistive heater and temperature sensor 1410 are placed below aptamer chamber 1404 to promote efficient heating and accurate sensing. The valve and deposition well 1406 are placed near the aptamer chamber 1404 to reduce analyte dilution after release due to adsorption to the channel walls or diffusion to dead fluid volumes. A waste outlet 1408 is used to remove any excess fluids or impurities. A heater 1410 is used to set the temperature of the chamber to an appropriate thermal release temperature.

The microfluidic chip structure is realized with three sandwiched polymer layers. Layer 1412 incorporates the inlets, passive valve, and waste outlet. To reduce bubble entrapment or dead volumes during sample spotting, layer 1414 provides an air vent connected to the spotting well. It also encapsulates the fluidic network present in layer 1412. Layer 1416 defines the spotting well and houses an air vent channel. A vent 1418 is used to prevent dead air volume during spotting. The sample is deposited on to a MALDI plate 1420 for analysis.

To illustrate some principles of the described subject matter, PC is achieved with adenosine monophosphate (AMP) as a model analyte by use of an adenosine triphosphate aptamer (ATP-aptamer) on an integrated microfluidic device. The device is coupled to a matrix assisted laser desorption/ionization mass spectrometry (MALDI-MS) machine where AMP is analyzed.

AMP is introduced into the microchamber and extracted by the aptamer. A rinse follows to flush out impurities through the waste outlet. For concentration, this procedure can be repeated to saturate AMP on the beads. Next, the microchamber is heated using the microheater to reverse the AMP/ATP-aptamer bond. This releases the analyte from the beads. In order to direct flow of a released AMP sample through a secondary channel leading to the spotting well, a valve based on surface tension is used.

The passive microfluidic valve, which directs the released analyte to the spotting outlet, exploits surface tension. That is, a pressure difference exists at the air-liquid interface in a sudden narrowing of a microchannel with hydrophobic surfaces. This pressure difference is provided by the Young-Laplace relationship and serves as a pressure barrier (e.g., critical pressure), which, only when exceeded, will allow the eluent (e.g., eluted sample) to enter the secondary channel and the spotting outlet:

$$\Delta p = 2\gamma \cos(\theta_c) \left[ \left( \frac{1}{w_1} + \frac{1}{h_1} \right) - \left( \frac{1}{w_2} + \frac{1}{h_2} \right) \right] \quad (1)$$

In Eq. 1, $\gamma$, $\theta_c$, w, and h are the surface energy, contact angle, width, and height of the channel, respectively, at the air-liquid interface. This pressure drop allows the hydrophobic channel to act as a passive valve, and, in the exemplary device, is used to regulate flow between the spotting outlet and the waste outlet. Since the packed chamber is the primary flow resister in the device (FIGS. 14(a)-(b)), a modified Poiseuille equation is used to determine its pressure drop:

$$\Delta p = \frac{150 \eta u (1-\varepsilon)^2 L}{d_0^2 \varepsilon^2} \quad (2)$$

Here, n, u, L, $\varepsilon$, and $d_o$ represent the dynamic viscosity, average fluid velocity, channel length, void fraction, and bead diameter, respectively. After sample spotting, the chip is removed from the MALDI plate for analysis.

EXAMPLE 1

One embodiment of the described subject matter further demonstrates some of the principles described. Biotinylated ATP-aptamer is purified while AMP, cytidine, uridine, and guanosine triphosphate (C/U/G-TP) are synthesized. The matrix solution is prepared from 2,4,6-trihydroxy-acetophenone (2,4,6-THAP), 2,3,4-THAP, and diammonium citrate at 0.1, 0.05, and 0.075 M concentrations, respectively, in a 3:5 (v/v) mixture of acetonitrile/water. Streptavidin coated agarose beads (~50 μm OD) provide support surfaces while a Voyager-DE time of flight mass spectrometer (Applied Biosystems) is used for mass analysis. DNA grade water is used in the example.

The device fabrication process is shown in FIGS. 15(a)-(e). FIGS. 15(a)-(e) depict an example fabrication process flow as seen from cross-section A-A' in FIGS. 14(a)-(b). FIG. 15a depicts PR patterning for Cr/Au deposition. FIG. 15b depicts thermal evaporation of a Cr/Au bi-layer. FIG. 15c depicts lift-off patterning of Cr/Au and PECVD deposition of $SiO_2$. FIG. 15d depicts a substrate drilled for fluidic ports and 3 through-hole polydimethylsiloxane (PDMS) layers aligned and permanently bonded. FIG. 15e depicts a packaged chip with tubing.

SU-8 molds for each microfluidic layer are first created, with which PDMS prepolymer is cast into an in-house built through-hole PDMS sandwiching jig and cured (60° C. for 8 hours). Meanwhile, Cr/Au (5/100 nm) films are deposited, patterned, and passivated with $SiO_2$ on glass substrates, realizing the microheater and temperature sensor. Following plasma ($O_2$) treatment of each bonding interface, all three PDMS layers and the glass substrate are then aligned using optical microscopy and an x-y-z stage before permanently bonding them to each other consecutively. Finally, microbeads are packed into the aptamer chamber and the entire assembly is subsequently attached to a MALDI plate via spontaneous adhesion.

The device is first rinsed with water (10 μl/min, 10 min). All following washing and loading schemes are identical. ATP-aptamer is loaded (10 μM, 10 μl, 20 min) into the chamber to functionalize the bead bed. After a subsequent wash, a pure matrix mass spectrum (MS) is acquired for a negative control.

An arbitrary concentration of fluorescein solution is used to characterize the valving operation and sample spot characteristics. For valving demonstrations, solution is first flowed through zone 1 (10 μl/min) below the critical pressure of the valve. To operate the passive valve, the waste outlet is plugged while maintaining a constant flow rate. This increases the pressure in the flow stream adjacent to the valve to eventually overcome its critical pressure and accentuate it. A 20× microscope objective is focused on the valve area during demonstration. To test sample spot characteristics, the waste stream is plugged while fluorescent solution is deposited from the chip using different flow rates (10-50 μl/min). Each spot is recorded and analyzed using a 20× objective.

For extraction/purification, 0.1 and 1.0 μM AMP samples are loaded into the aptamer chamber separately. A rinse follows to eliminate non-specific compounds. AMP is then released from the aptamer by raising the chamber temperature to 38° C. while introducing a matrix sample plug. The sample/matrix plug is then transferred to the spotting well and deposited onto the MALDI plate to be subsequently analyzed. Similarly, for specific extraction of AMP, a solution of AMP, CTP, UTP, and GTP (1 μM) is loaded into the aptamer chamber. After an incubation (5 min) and wash procedure (to flush out non-target molecules), matrix is loaded into the chamber. The heater is activated to release the molecules currently on the aptamer and deposit them onto the MALDI plate for analysis.

For preconcentration of AMP, a multiple injection scheme is used. The aptamer chamber is consecutively loaded with 10 nM injections of AMP sample. Each injection is incubated (5 min) and followed by a rinse. Upon suspected saturation of the aptamer with AMP, the chamber is heated to release the analyte into a matrix plug. The analyte is then deposited for analysis.

Figure 16B:
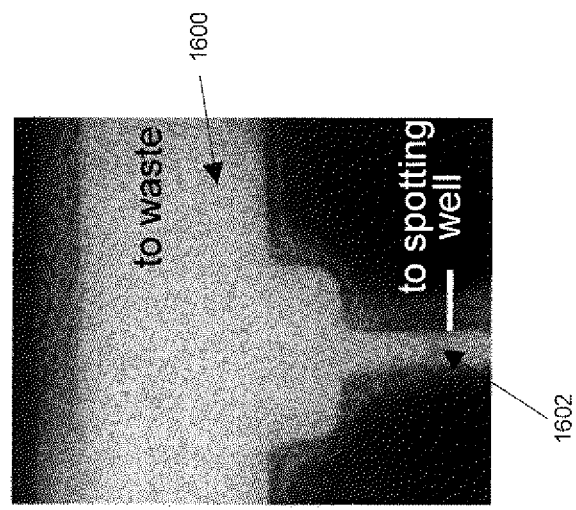
FIGS. 16(a)-(b) depict operation of a passive valve: (a) fluorescein solution flowing through the waste outlet bypassing valve and (b) valving fluorescein solution through the valve according to an exemplary embodiment of the described subject matter.
Figure 16A:
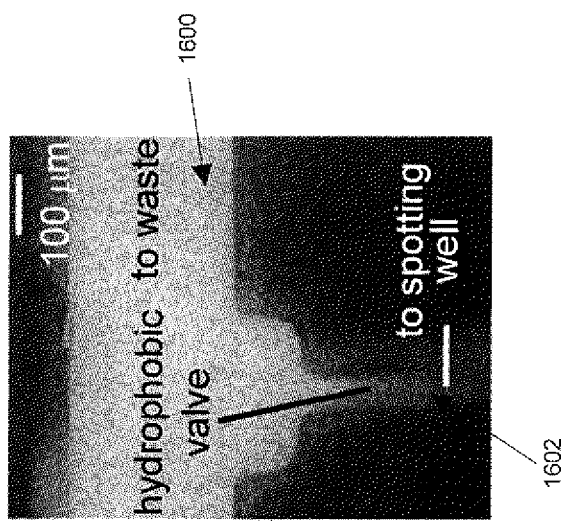

To ensure the validity of the higher-level data, properties of the microfluidic valve (FIGS. 16(a)-(b)) are obtained. At a steady flow rate, the pressure difference imparted by the microfluidic valve 1602 impinges fluid access to the spotting outlet. When the waste outlet 1600 is open and at flow rates below 50 μl/min (e.g., 10 μl/min), fluid flow bypasses the valve since the hydrodynamic pressure driving flow (~686 Pa) was smaller than the critical pressure of the valve (FIG. 16a). To direct flow to the MALDI plate, the pressure drop between the sample inlets to the waste outlet 1600 can be greater than the valve's critical pressure (i.e., above 3.154 kPa). This is accomplished by plugging the waste outlet 1600 using an external valve, and maintaining a constant flow rate, which allows fluorescein solution to enter the channel leading to the spotting outlet (FIG. 16b).

Figure 17:
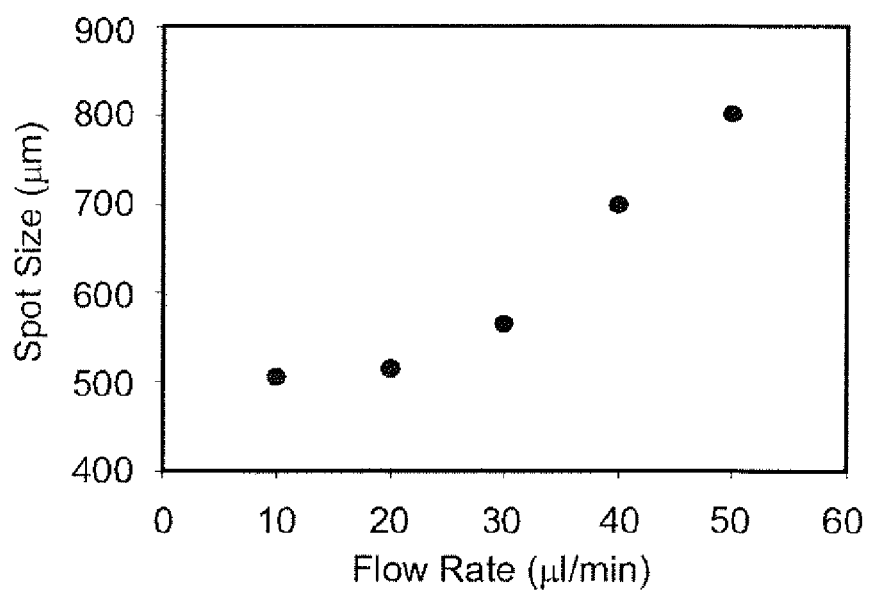
FIG. 17 depicts spot size on a MALDI plate as a function of flow rate used to transfer the sample to the deposition well according to an exemplary embodiment of the described subject matter.

Sample spot size can be a useful characteristic during MALDI analysis. Large volume spots can promote dissociation of matrix from sample upon spot crystallization, resulting in poor ionization. Additionally, non-uniformity in sample concentration throughout the spot can occur, degrading analysis. Spot size produced by the device is measured as a function of driving flow rate (FIG. 17). For low flow rates (10-30 μl/min), spot sizes approximately equal to the well size are obtained (~500 Higher flow rates (>40 μl/min) generate a larger spot diameter (~700-800 μm) since the seal between the PDMS and MALDI plate at the location of the spotting well tends to falter at the resulting higher pressures. Consequently, the sample spot broadens once the chip is removed from the plate to obtain a spot size. However, this is of no detriment to the overall performance of the device compared to conventional spotting (with syringe or pipette), where crystallized spots are larger (>1 mm).

Figure 18A:
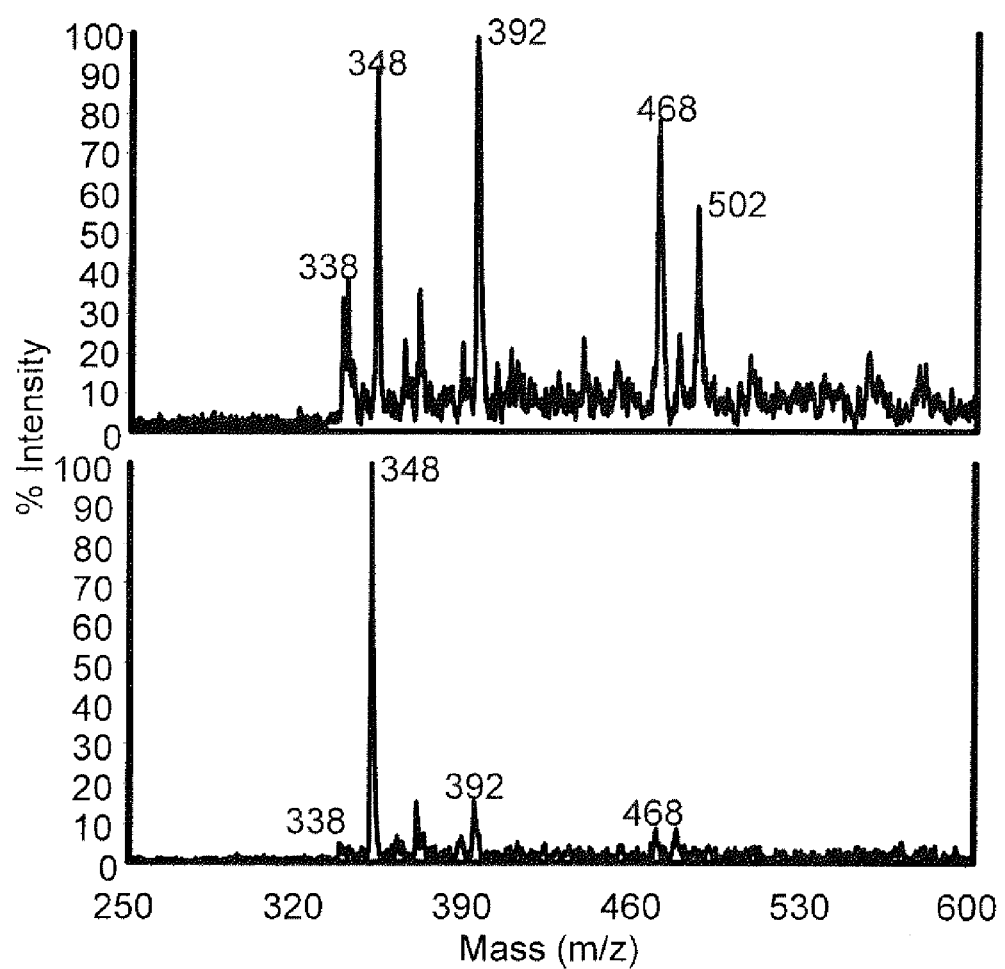

As described, to demonstrate AMP extraction by ATP-aptamer, two sample solutions of AMP (0.1 & 1.0 µM) are first injected into the chamber. AMP is released and deposited onto a MALDI-MS plate and analyzed (FIG. 18a). The MS of a spot obtained from a 0.1 µM AMP solution (FIG. 18b) shows a distinctive mass peak of 348.11 Da, which corresponds to AMP (established value: 347.22 Da). Since AMP concentration is relatively low, the magnitude of this peak is comparable to several peaks from the MALDI matrix (338, 393, & 468 Da). A mass spectrum obtained from a 1.0 µM AMP solution (FIG. 18c) improves the analyte-to-reference peak contrast. In this case, the AMP peak dominates reference peak amplitudes, suggesting that concentrating dilute samples can improve analyte recognition. Although mass spectrometry is a precise detection technique, various fluctuations in instrument settings (e.g., electromagnetic field strength, detector vibrations, and laser intensity) will cause expected m/z values of a substance to vary slightly. Hence, the molecular ion peak in m/z for AMP (and other noteworthy peaks) in this description will not always be exactly their predicted value (e.g., 348.22 for AMP) and would rather deviate slightly. Such slight deviations do not affect molecular identification and are generally accepted for mass spectrometry.

Figure 19:
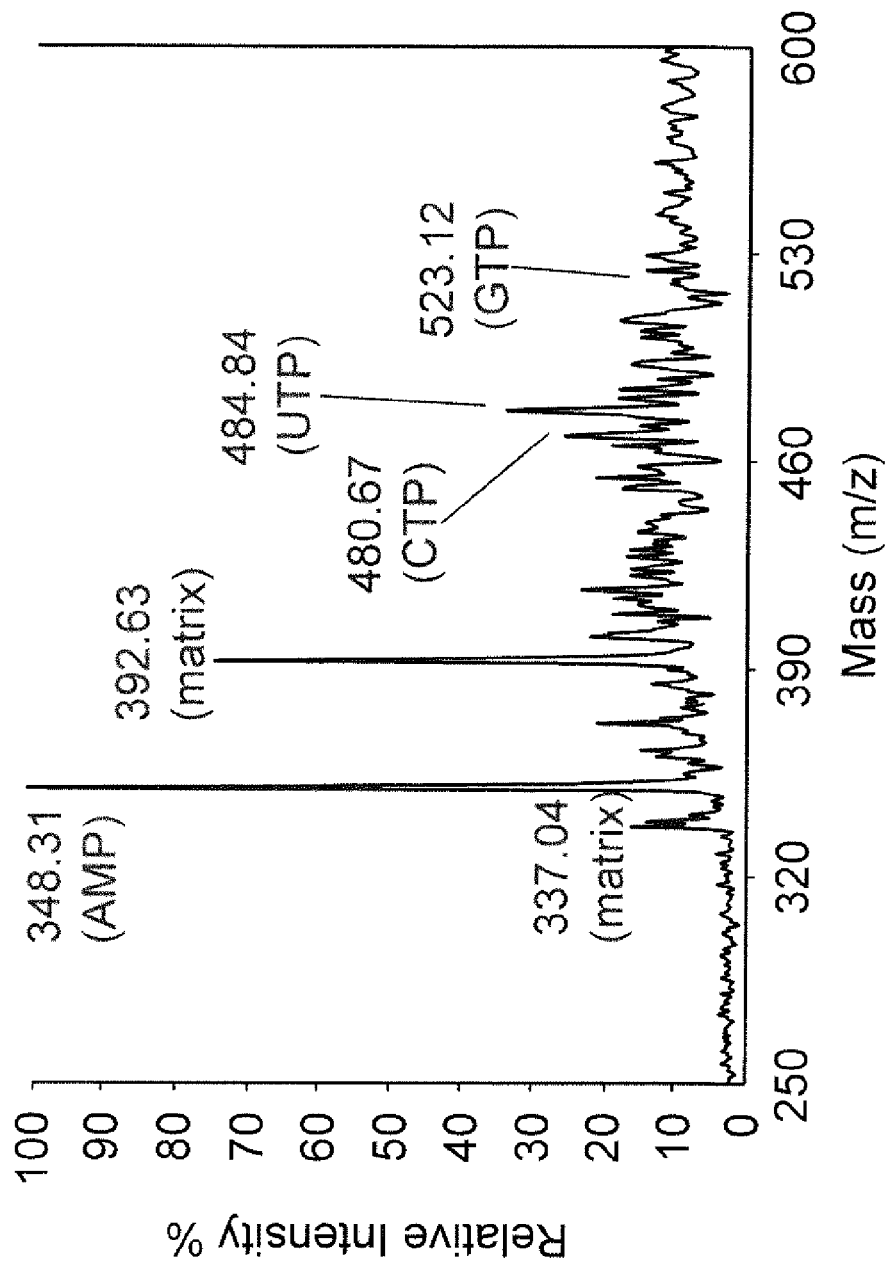
FIG. 19 depicts MS from an injected sample of AMP, CTP, UTP, & GTP (1 µM each) where AMP is isolated according to an exemplary embodiment of the described subject matter.

In some embodiments, purification of analytes can be a valuable tool for selectively controlling analytes in biochemical applications. AMP is selectively extracted from a homogeneous solution of AMP, CTP, UTP, and GTP (1.0 µM each) by loading the sample into the aptamer chamber and subsequently washing the chamber to isolate AMP. A deposited sample spot is obtained similarly to previous protocol. FIG. 19 represents the MS of an analyte sample originating from the homogeneous solution. The ratio of AMP to noise is comparable to that seen in FIG. 18c, where only AMP is present in the solution. Additional non-target peaks are observed (480, 484, & 523 Da). However, their intensities are significantly lower than the AMP peak, suggesting that the amount of non-specific binding is negligible. This confirms the ability of the described subject matter to selectively extract and concentrate biomolecules for analytical applications.

Figure 18B:
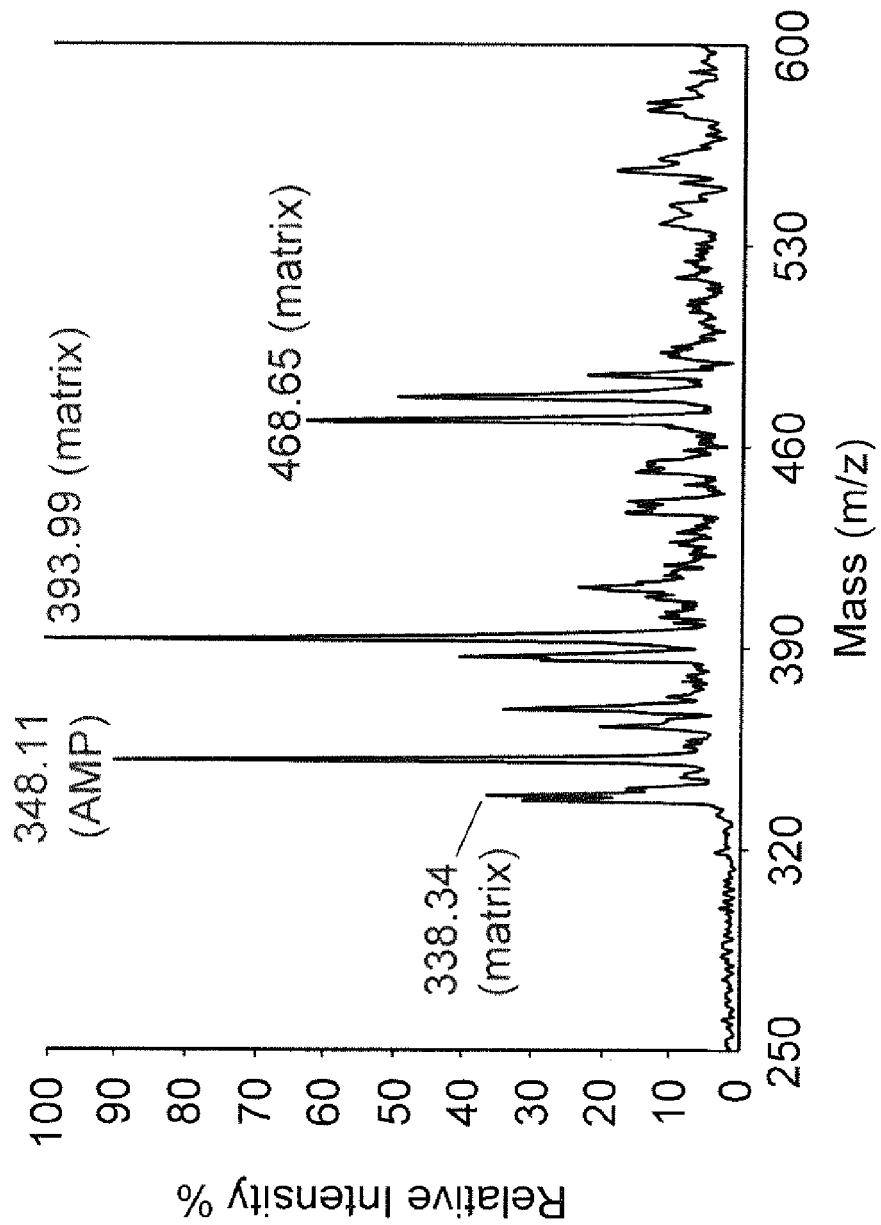
Figure 20A:
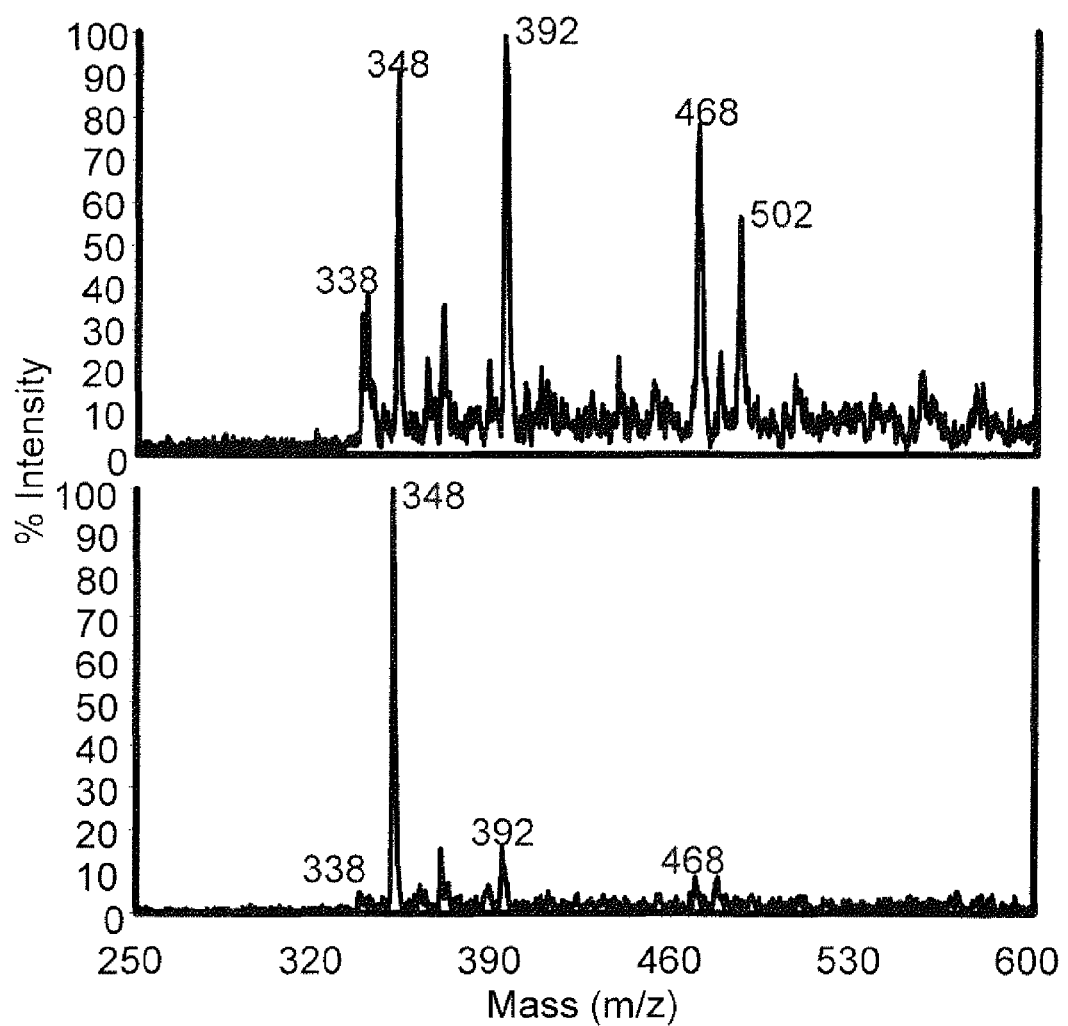
Figure 20B:
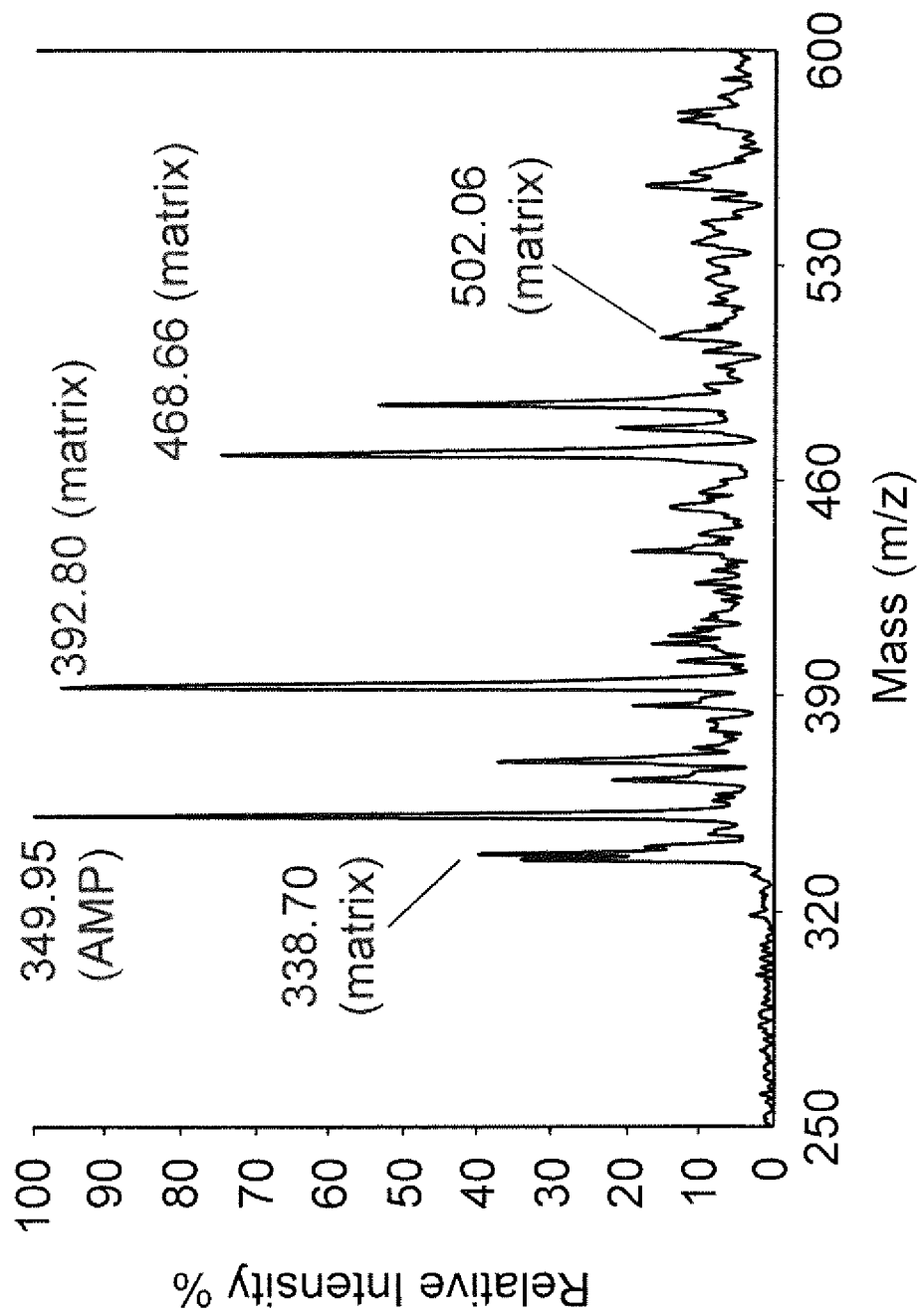

As a sample preparatory technique, PC can be useful for sample conditioning and analyte signal improvement. In another embodiment, PC performance of the device is demonstrated by loading a dilute AMP sample into the aptamer chamber multiple times to saturate the analyte on the aptamer bed before release for MS analysis. FIGS. 20(a)-(d) depict MS from a sample spot according to exemplary embodiments of the described subject matter. Dilute sample concentration is chosen to be lower (~0.01 µM) in order to highlight the detection enhancement due to PC. 25 consecutive dilute AMP samples are injected into the aptamer chamber, release the captured AMP with heat, and transfer the concentrated plug to the spotting well. An MS is obtained from the resulting sample spot (FIG. 20b). An AMP peak to noise ratio slightly higher than that seen in FIG. 18b is observed, demonstrating the successful concentration of AMP by ~10×.

More consecutive injections of dilute AMP solution are attempted to obtain the maximum PC factor of the device. A maximum of 250 injections are performed. Following the final injection, a sample spot is obtained and analyzed with MALDI-MS, similar to the protocol with 25 injections (FIG. 20c). It can be seen that the AMP peak dominates those of reference peaks and the AMP peak to noise peak ratio is comparable to that shown in FIG. 18c. This suggests a PC factor of nearly 100×. This is a useful PC factor, similar to that seen in the reverse-phase devices, but with the advantage of higher specificity. AMP sample injections are stopped after 250 injections due to demonstration practicality, not because of actual saturation of the analyte. This suggests the possibility for larger PC factors using principles of the described subject matter.

EXAMPLE 2

Another embodiment illustrates the principles of the described subject matter. Biotinylated adenosine triphosphate aptamer (bio-ATP-40-1, or ATP-aptamer) is HPLC purified by Integrated DNA Tech. AMP is synthesized and fluorescently labeled with thiazole orange (TO). Buffer solution (pH 7.4) is prepared from Tris-HCl (20 mM), NaCl (140 mM), KCl (5 mM), and $MgCl_2$ (5 mM) in water. Streptavidin coated polystyrene beads (50-80 µm, OD) are acquired from Pierce. A Nikon Eclipse TE300 microscope and CCD is employed for fluorescence detection. Temperature control is accomplished with a thermoelectric device and type-K thermocouple. A New Era NE-1000 syringe pump enables flow in the device.

Figure 1:
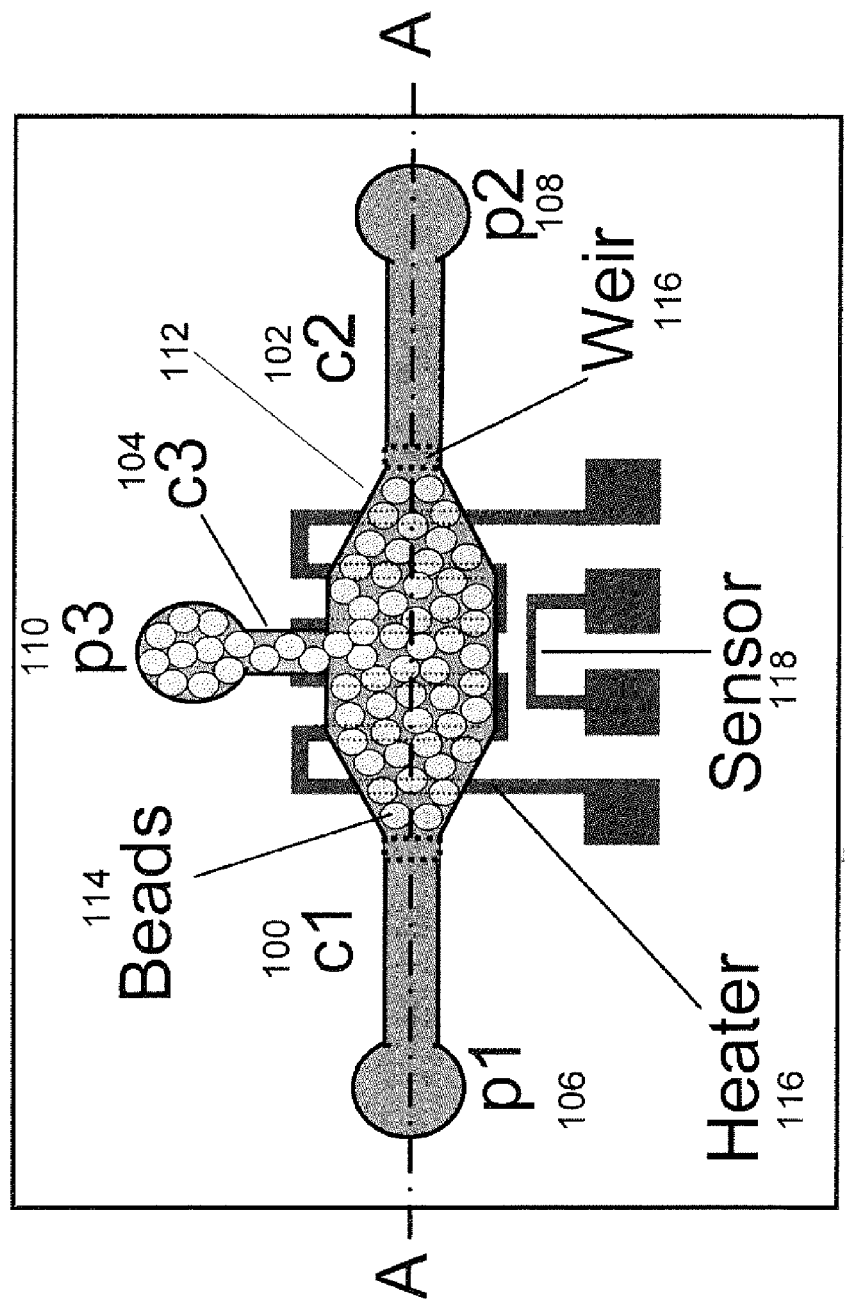
FIG. 1 is a schematic drawing showing an example device according to one embodiment of the described subject matter.

A device schematic is shown in FIG. 1. Channels 100 and 102 (5.1 mm×400 µm×40 µm) transferred sample and discharged waste from the chamber 112 (8.7 mm×3 mm×140 µm). Microbead 114 packing into the chamber is accomplished through 104. Ports 106, 108, and 110 are 1 mm in radius and 140 µm thick. Chamber and microfluidic network volumes, respectively, are 3.09 µl and 3.60 µl.

Figure 2D:
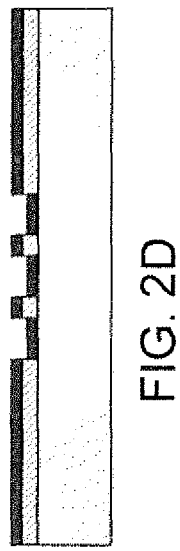
FIGS. 2(a)-(f) depict an example according to an embodiment of the described subject matter. The figure shows a fabrication technique: 2a-c show polydimethysiloxane (PDMS) channel techniques, 2d-e show processing of integrated heater and temperature sensor, and 2f shows a complete package.
Figure 2E:
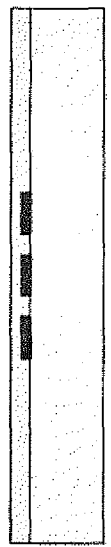
Figure 2F:
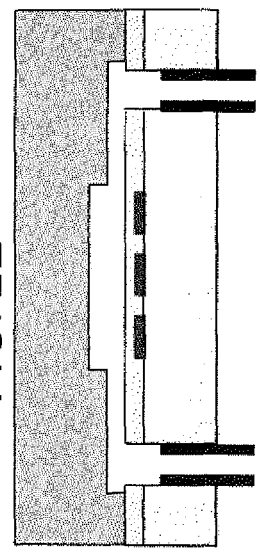
Figure 2A:
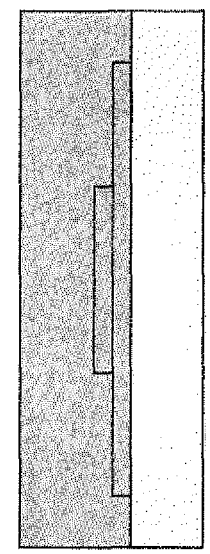
Figure 2B:
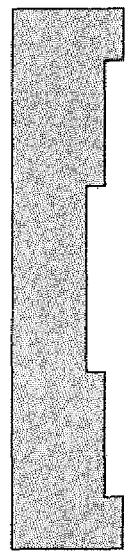
Figure 2C:
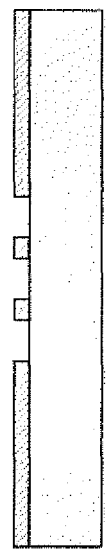

Channels are fabricated using PDMS micro-molding by soft lithography (FIGS. 2(a)-(f)). A mold is created on a 4-in silicon wafer by patterning SU-8. PDMS pre-polymer solution is mixed (10:1; w:w), degassed, and semi-cured (70° C., 50 min) over the mold (FIG. 2a-b). In parallel, glass substrates are cleaved (25 mm×30 mm) and drilled to create ports 106-110 (refer to FIG. 1) (FIGS. 2c-e). The semi-cured PDMS sheet is removed from the mold, aligned, and bonded to the glass following $O_2$ plasma treatment of the bonding interface. Permanent bonding is realized with a final bake (25 min at 85° C.).

Packaging of the device is accomplished by inserting silica capillary and Tygon tubing (FIG. 2f), (0.6 mm ID, 0.7 mm OD) and (0.6 mm ID, 3.18 OD), respectively into ports 106-110. The interfaces are then sealed with epoxy.

The device is mounted on the microscope stage using clips or double-sided tape. A blue excitation filter combined with a green-pass dichroic mirror is used. A 10× objective is kept focused on a single area of the chamber.

The chamber is initially rinsed with buffer (50 µl/min, 10 min). The following rinses are identical. Streptavidin coated beads are introduced via c3 by manual pressure. The chamber and channels are rinsed and bio-ATP-aptamer is injected (20 µM, 20 µl, 10 µl/min) and incubated (20 min) in the chamber. After a final rinse, a fluorescence control is established.

Extracting distinct concentrations of AMP (24.5° C., 10 µl, 10 µl/min) establishes a fluorescence intensity curve. The procedures use the above injection parameters. Solution concentrations range from 0.1-10 µM and fluorescence is detected after rinsing between separate extractions.

For PC of AMP, multiple solution injections are used. Two devices (Device 1 & Device 2) are consecutively loaded with 200 nM and 500 nM injections, respectively. On either device, each injection is incubated (5 min), rinsed, and checked for fluorescence before the next injection occurs.

To estimate the relationship between fluorescence signal intensity and surface concentration, AMP solution is extracted at increasing concentrations onto multiple devices.

Figure 3:
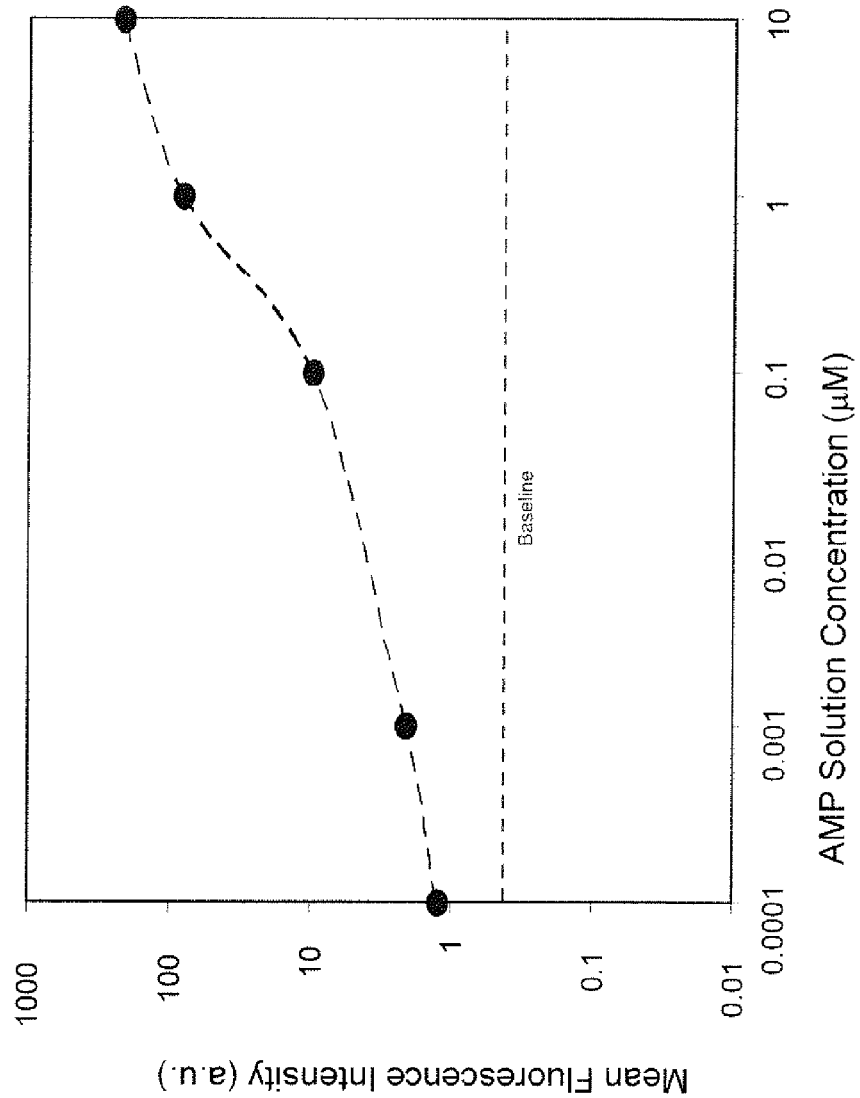
FIG. 3 depicts an example according to an embodiment of the described subject matter. The figure shows the relationship of fluorescence signal to TO-AMP concentration in solution.

An S-shaped relationship can be observed between the mean fluorescence intensity and AMP concentration, which appears to be a dose-responsive characteristic (FIG. 3).

Figure 4A:
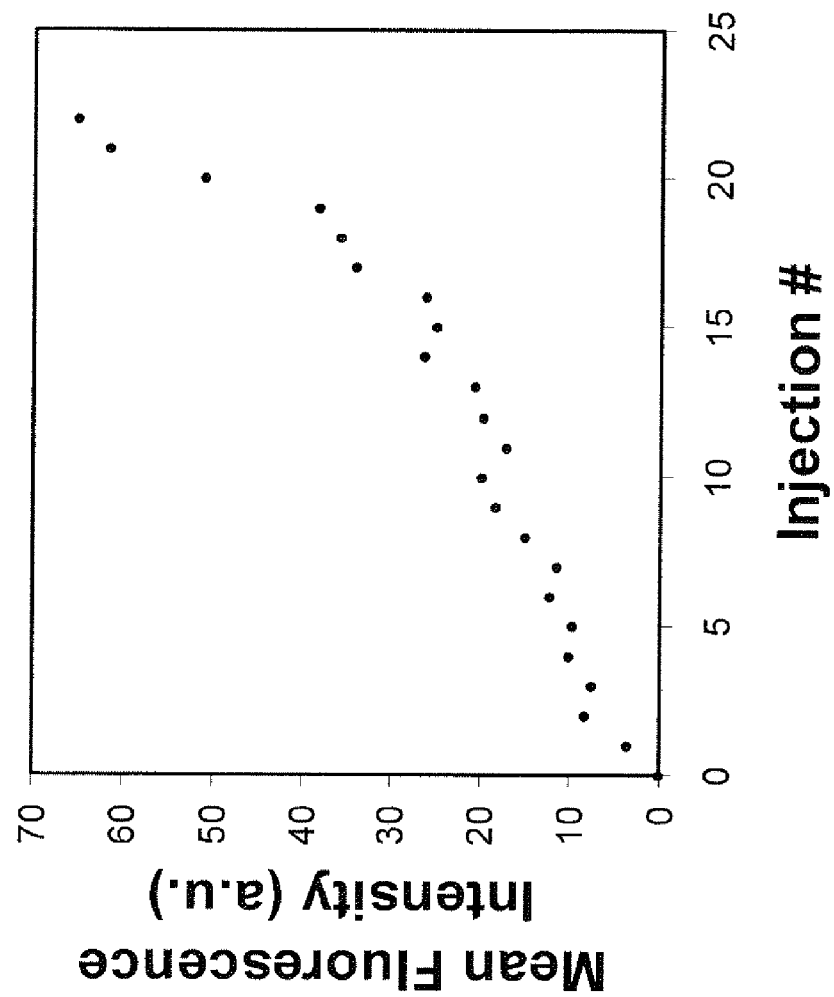
FIGS. 4(a)-(b) depict exemplary aptameric concentration of analytes using an example device according to the described subject matter.
Figure 4B:
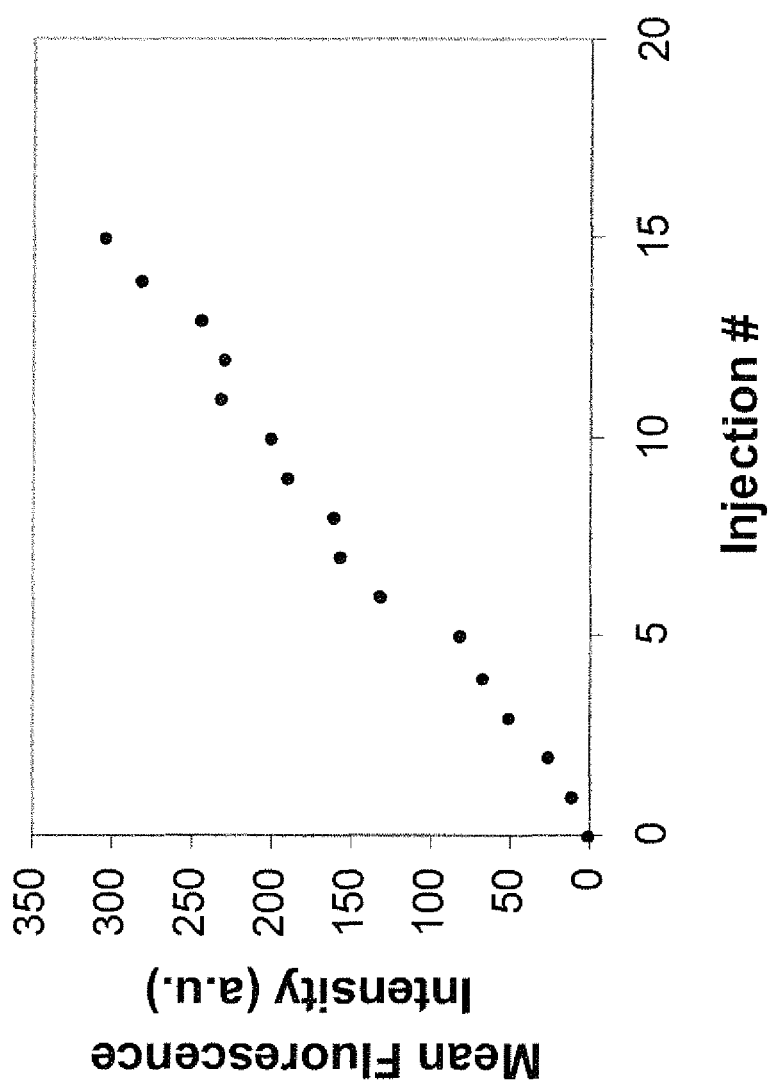

Preconcentration is demonstrated with 2 dilute solutions of TO-AMP on separate devices by extracting multiple injections on each device (FIGS. 4(a)-(b)). In both demonstrations, fluorescence signal increases after each consecutive sample load, indicating increased concentration of bound TO-AMP on the surface. In addition, Devices 1 and 2, after a roughly 10-fold PC, show no sign of signal saturation within the tested injection range, meaning the surface is capable of concentrating yet more analyte.

Figure 5:
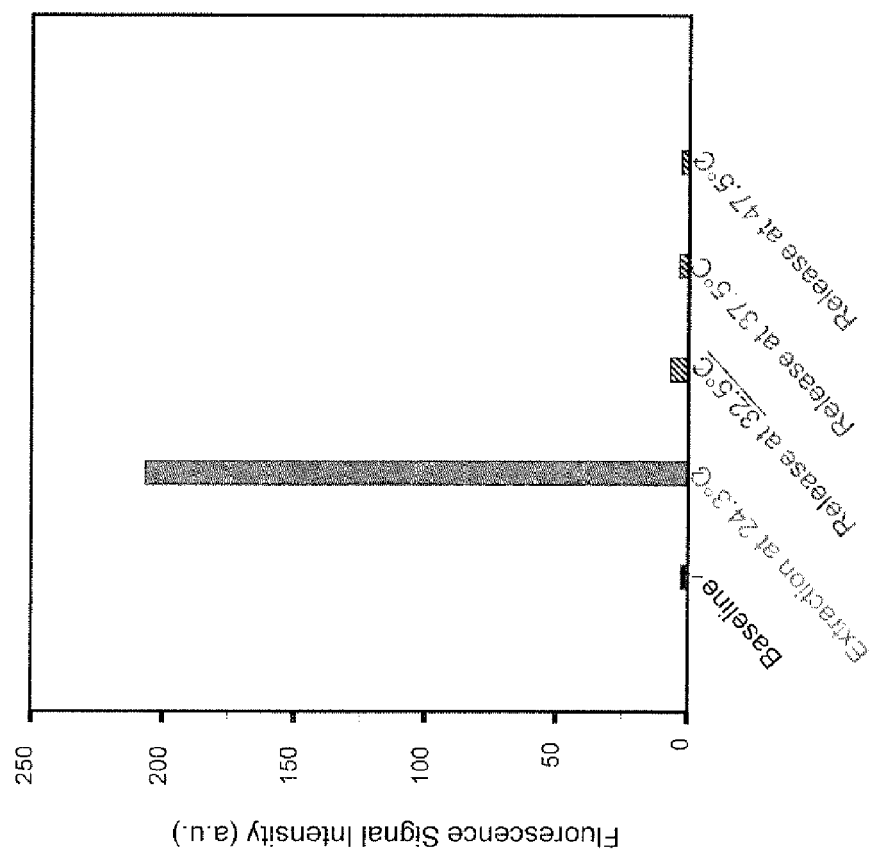
FIG. 5 depicts thermal release of AMP from bead surfaces incubated with 10 µM injection according to an embodiment of the described subject matter.

To demonstrate the aptamer thermal release properties, a 10 μM AMP solution is extracted and eluted for a range of temperatures (30-50° C.) (FIG. 5). After extraction of AMP on the aptamer surface, a high intensity fluorescence signal is obtained. At 32.5° C., there is a sharp decrease in signal intensity (near baseline). As the temperature is further increased to 47.5° C., the signal matches the baseline intensity. No signal implies an absence of coupled AMP on the device affinity surface, meaning release of analyte. Thus, the device exhibits adequate release of a captured target analyte at sufficiently low temperature (32.5° C.). Regeneration at this temperature does not endanger the viability of thermally sensitive biomolecules.

To demonstrate the functionality of the aptamer surface post-release of AMP, extraction of 10 μM AMP ($1^{st}$ Extraction) is followed by three elevated temperature release 75, 85, and 95° C., which is in turn followed by a second extraction ($2^{nd}$ Extraction) (FIG. 6 series A, B, and C, respectively). It can be observed that when TO-AMP was released at 75° C. in series A, the subsequent extraction (the $2^{nd}$ Extraction) yielded fluorescence intensity comparable to that from the pre-release extraction. On the other hand, in series B and C, $2^{nd}$ Extraction fluorescence signals were significantly lower following release at further elevated temperatures (85 and 95° C., respectively). This led us to conclude that most aptamer molecules had separated from the microbeads because of streptavidin-biotin denaturation.

EXAMPLE 3

Figure 7B:
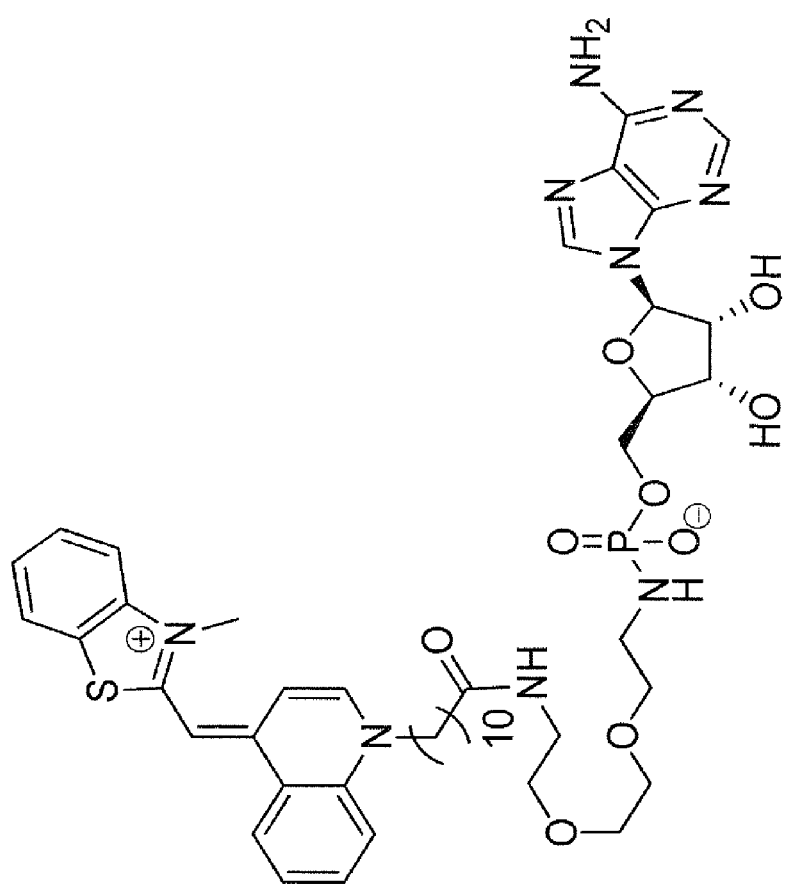

Biotinylated adenosine triphosphate aptamer (bio-ATP 40-1, or ATP-aptamer) (FIG. 7a) is acquired (e.g., from Integrated DNA Technologies (Coralville, Iowa)) and purified by high pressure liquid chromatography. AMP is coupled with thiazole orange ("TO-AMP") (FIG. 7b). To-AMP can be replaced with any appropriate molecule+probe combination. Adenosine triphosphate (ATP) is purchased from Sigma-Aldrich Co. (Milwaukee, Wis.). Diethyl pyrocarbonate treated sterile water (SW), from Fisher (Pittsburgh, Pa.), is used. Buffer solution (pH 7.4) is prepared by mixing Tris-HCl (20 mM), NaCl (140 mM), KCl (5 mM), and $MgCl_2$ (5 mM) in sterile water. Chemicals for the buffer solution are purchased through Fisher Scientific. ATP aptamer, TO-AMP, and ATP working solutions are all prepared using Tris-HCl buffer. UltraLink immobilized streptavidin polystyrene beads (50-80 μm in diameter) are acquired from Pierce (Rockford, Ill.). All solvents, isopropyl alcohol (IPA), methyl alcohol, and acetone are of purified grade (Mallinekrodt Baker, Phillipsburg, N.J.). SU-8 2025 and 2100 is purchased from MicroChem (Newton, Mass.). Poly-dimethylsiloxane (PDMS) is acquired from Robert McKeown Company (Somerville, N.J.). Torr Seal epoxy and silicone glue is obtained from Varian (Palo Alto, Calif.) and Action Electronics (Santa Ana, Calif.), respectively. Glass slides (25 mm×75 mm) are purchased from Fisher. Silica capillary tubing and Tygon polyvinyl chloride (PVC) tubing are purchased from Polymicro Technologies (Phoenix, Ariz.) and McMaster Carr (Dayton, N.J.), respectively. Arctic Silver 5 is obtained from Arctic Silver Inc. (e.g., used for IC component bonding) and Kapton Tape is purchased from Techni-Tool (Worcester, Pa.).

Mercury vapor lamp induced fluorescence using a Nikon Eclipse TE300 inverted epi-fluorescence microscope (Nikon, USA) is employed for detection. Fluorescence micrographs are recorded using a Q-Imaging model Retiga 2000R Mono-12-bit CCD and analyzed with Q-Capture Pro software (Austin, Tex.). Device temperature control is performed using a thermoelectric device from Meteor (model: CP1.4-71-06L, Trenton, N.J.). DC potential is supplied to the thermoelectric device with an Agilent E3631 DC power supply (Santa Clara, Calif.). A type-K surface thermocouple model CO3-K and a model HHM-290 multimeter (Omega, Stamford, Conn.) are used to measure device temperature. Microfluidic flow is provided from a New Era model NE-1000 syringe pump (Farmingdale, N.Y.), 5 $cm^3$ syringes, and 21 gauge (38.1 mm long) needles (Becton Dickinson, Franklin Lakes, N.J.). Diamond-tipped drill bits (0.7 mm diameter) and a Model 7000 standard drill press are obtained from Servo Products (Eastlake, Ohio).

Figure 8:
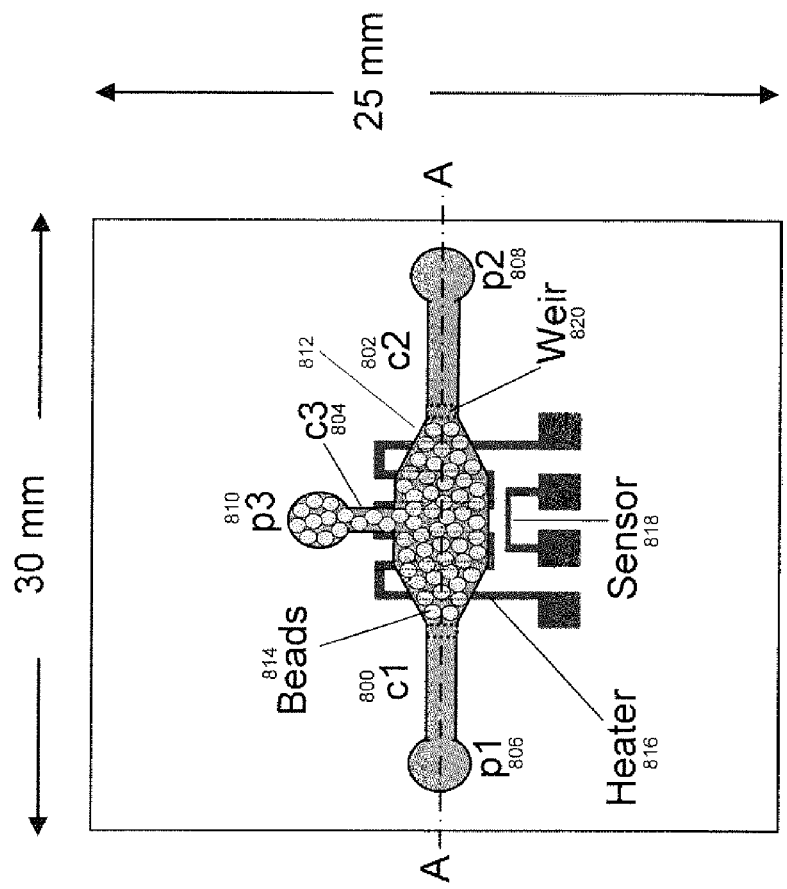
FIG. 8 depicts an example layout of the microfluidic SPE device used for this demonstration according to an exemplary embodiment of the described subject matter

A device is shown in FIG. 8. The channels are numbered for reference. Channels 800 and 802 (5.1 mm×400 μm×40 μm) are used to deliver sample and buffer solution to the chamber (8.7 mm×3 mm×140 μm). Channel 804 is used to pack the beads 814 (e.g., polystyrene beads). The ports have radii of 1 mm each and are 140 μm thick. Hence, chamber 812 has an effective volume of 3.09 micro-liters with the tapers taken into consideration, whereas the microfluidic device volume (on-chip) is 3.60 micro-liters. Using Poiseuille-flow, the maximum pressure drop across this device (port to port), excluding beads, can be calculated from:

$$Q = \frac{\pi (D_h)^4 \Delta p}{128 \, \mu l}. \tag{3}$$

Here, Q is the flow rate, $\Delta p$ is the pressure drop, μ is the dynamic viscosity of the fluid, l is the channel length, and $D_h$, is the hydraulic diameter given by the expression $$D_h = \frac{4A}{P}. \tag{4}$$

In (4), A is the cross-sectional area of the channel and P is the wetted perimeter. For water, the calculated pressure drop for Q=50 μl/min used in the demonstrations is 6.83 kiloPascal. When considering a packed chamber of micro-beads, the pressure increase is estimated to be 10-20 times greater.

Microchip solid-phase extraction (SPE) devices are fabricated on glass slides by PDMS micro-molding using standard soft lithography techniques. A simplified device process flow (FIGS. 9(a)-(f)) shows primary fabrication procedures. An SU-8 mold for PDMS curing and channel fabrication is created on silicon wafers (101 mm) from Silicon Quest International (Santa Clara, Calif.). Fabrication begins with deposition and patterning of 15 nm Cr alignment marks via thermal evaporation on an Edwards/BOC Auto306 thermal evaporator (Wilmington, Mass.), followed by lift-off in acetone overnight. Secondly, patterning of SU-8 2025 realizes channels

800 and 802 (40 μm thick) (FIG. 9*b*), whereas SU-8 2100 resist completes the mold, producing the reaction chamber and channel 804 (140 μm).

Figure 9A:
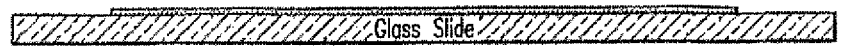
FIGS. 9(a)-(f) depict a simplified device flow: (a-d) a microchannel realized with standard soft lithography techniques and (e & f) a package according to exemplary embodiments of the described subject matter. Line A-A' in the schematic of FIG. 8 is a cross-section reference
Figure 9B:
Figure 9C:
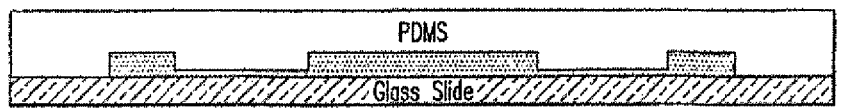
Figure 9D:
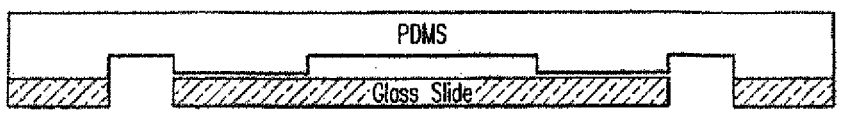

PDMS pre-polymer solution is mixed with a mass ratio of 10:1 and distributed on the mold (FIG. 9*c*). The pre-polymer is degassed by vacuum (30 min) and followed by semi-curing (70° C., 50 min). In parallel, glass substrates are diced (25 mm×30 mm) and drilled to create the access ports (806-810) (FIG. 9*d*). The glass substrates are then cleaned using a solution of $H_2SO_4$ and $H_2O_2$ (7:4 vol/vol at 130° C.). In other embodiments, ports can be fabricated in the PDMS blank layer. The semi-cured PDMS sheet is removed from the SU-8 mold, aligned and bonded to the glass slides following $O_2$ plasma treatment of the bonding interface in a Technics Series 800 Micro R1E device (100 mtorr and 85 W) for 15 seconds. Permanent bonding and curing of PDMS to the substrate is performed by heating the chip (25 min at 85° C.).

Figure 9E:
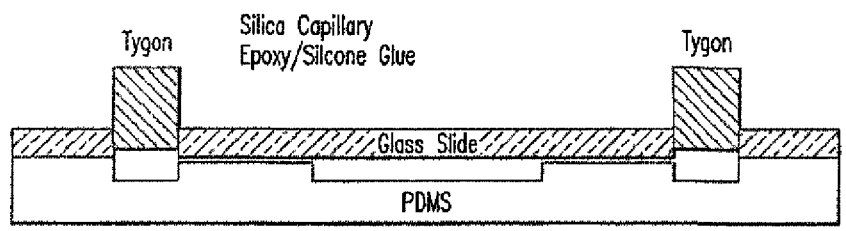
Figure 9F:
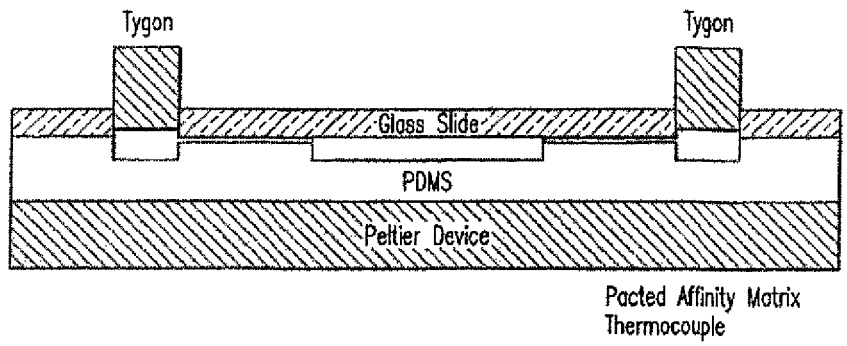

Packaging is accomplished by inserting a combination of silica capillary tubing (0.6 mm ID, 0.7 mm OD) segments along with Tygon PVC tubing (0.6 mm ID, 3.18 OD) through the drilled access ports (FIG. 9*e*). The connection interfaces are sealed using silicone glue and Torr seal epoxy. For thermal related demonstrations, a thermocouple is subsequently sandwiched between a peltier device and the bottom of the microfluidic chip (FIG. 9*f*). The components are held together by thermal interfacing paste or Kapton Tape.

Figure 10:
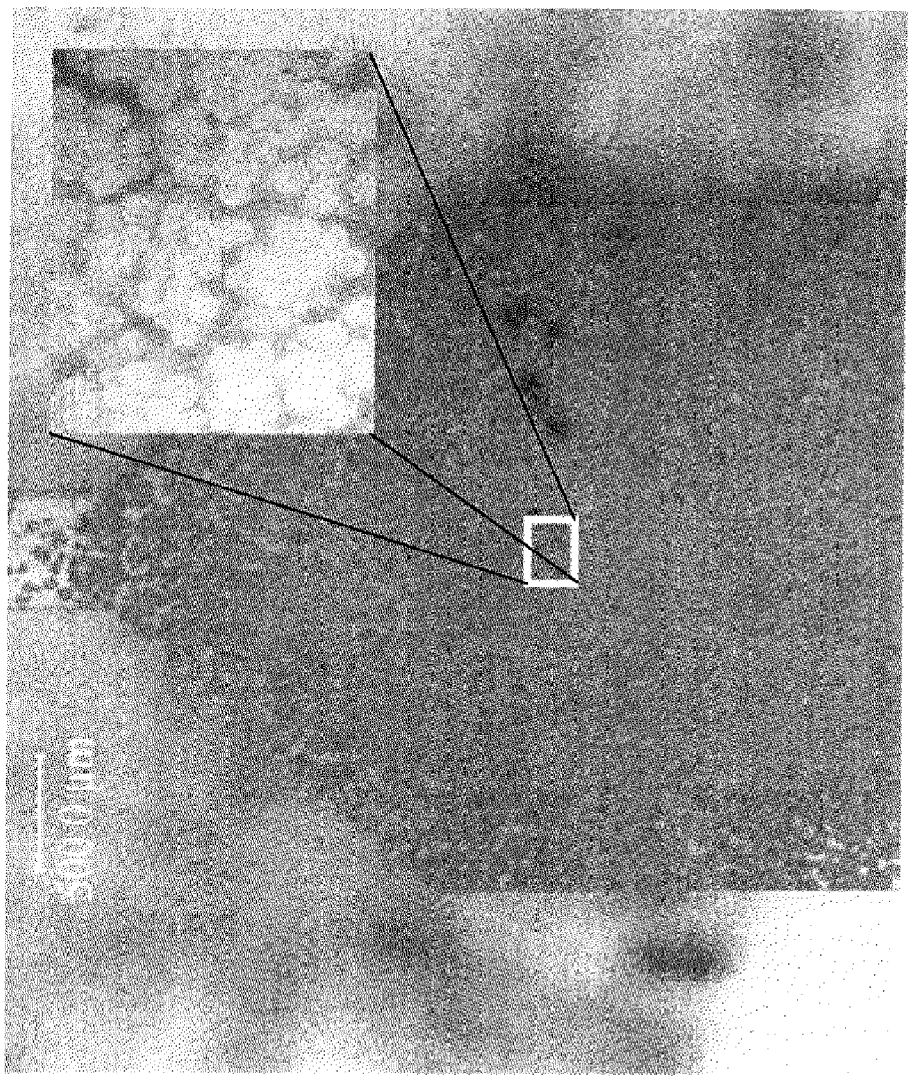
FIG. 10 depicts a bright-field micrograph of the chamber, including a magnified area for fluorescence imaging and processing according to an exemplary embodiment of the described subject matter

Fluorescence detection is done using a Nikon TE300 and a Q-Imaging Retiga 2000R device. During analyte binding, TO emission occurs at 530 nm when excited at 480 nm, so a blue light filter and green-pass dichroic mirror are used accordingly. The device is mounted in the same position using double-sided scotch tape marks on the microscope stage. For each image, a 10× objective is used to collect emitted fluorophores from the same area of the chamber (FIG. 10). These operating conditions are identical for all images taken for fluorescence detection of the analyte.

The entire microfluidic device is flushed (50 μl/min) with the buffer solution for 30 minutes by using any port as an inlet and collecting waste from both remaining ports. Streptavidin coated beads are suspended in buffer (4 ml) and loaded into a 5 ml syringe. Manual pressure is used to pack the beads from channel 804 via port 810 into the chamber. Subsequently, channel 804 is sealed permanently near the port interface using silicone glue. The chamber and channels are washed (50 μl/min) with buffer (30 min) through 800. ATP-aptamer solution (20 μl, 20 μM) is injected (10 μl/min) and allowed to incubate (20 min) in the chamber. The channel is washed again (50 μl/min for 20 min) and a baseline fluorescence signal is taken.

For SP purification/extraction, TO-AMP at different concentrations (400 nM, 500 nM and 10 μM) is loaded (10 μl at 10 μl/min) into the reaction chamber from channel 800. The solution is kept stagnant in the chamber for 10-15 minutes to allow complete interaction between the analyte and aptamer surface of the beads. Following the purification of analytes, the chamber is washed (50 μl/min for 15 min) with buffer to eliminate all non-specific compounds, un-reacted molecules, and impurities. A subsequent fluorescence image is taken. TO-AMP is released and collected in two ways: the first technique uses competitive displacement of TO-AMP by incubating different concentrations of ATP (800 μM and 3200 μM); the second technique uses elevated chip temperature (80° C.) while buffer is flowed (10 μl at 5 μl/min) through to collect analyte.

During purification, time resolved analyte adsorption demonstrations are conducted. For a 400 nano-molar concentration of TO-AMP solution, fluorescence micrographs are recorded at time intervals of 1 minute. Images ceased to be taken after the observed fluorescence level shows no appreciable change.

An integrated SPE bed is prepared using a double weir design forming a cavity. Using PDMS for the channel material can present challenges. Since PDMS is pliable, beads can be pushed under the weir structures under positive pressure resulting in backpressure. During bead introduction, port 810 is prone to clogging. Designs using drilled access ports in the PDMS blank layer can be a source of this problem. The holes in PDMS are plagued with burrs containing loose PDMS particles not cleared while drilling, which became obstacles and instigated clogging. This is mitigated by generating reversed flow and allowing beads to dislodge and flow back toward the source. On occasion, several forward/reverse pumping cycles are used to fully clear obstructions and continue filling the chamber. Drilling holes in the glass slides provides smoother, burr-free edges. Using this technique, fully packed chambers are realized in over 90 percent of devices.

Another source of backpressure comes from the beads themselves, especially when using narrow uniform-width channels. To minimize backpressure of this sort, a widened chamber design is employed to contain the affinity matrix. Although the expansion ratio utilized (400 μm/3 mm) can be improved, the backpressure is minimized, and the device functions in a fashion similar to open micro-channels.

Figure 11A:
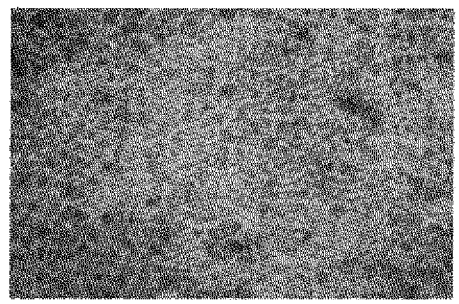
FIGS. 11(a)-(b) depict time resolved extraction of TO-AMP (400 nM) by ATP-aptamer according to an exemplary embodiment of the described subject matter. Measurements are made in the (A-A') direction of the linked micrograph as shown in FIG. 11(a). At each time level, fluorescence intensity is sampled, averaged, and normalized to produce a single value point for each interval.
Figure 11B:
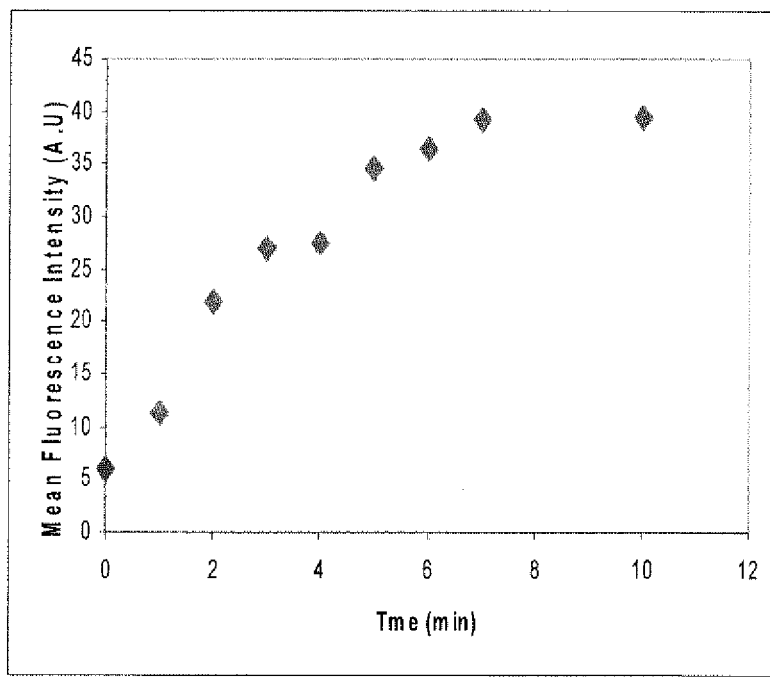
Figure 12A:
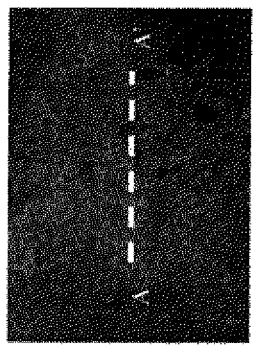
FIGS. 12(a)-(e) depict micrographs displaying SPE extraction of 3 concentrations of TO-AMP according to exemplary embodiments of the described subject matter: (a) baseline fluorescence; (b) 400 nM; (c) 500 nM; and (d) 10 µM.
Figure 12C:
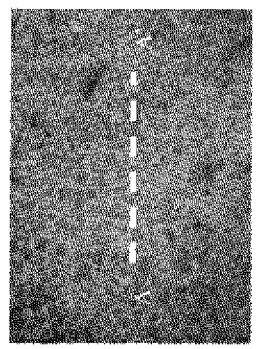
Figure 12B:
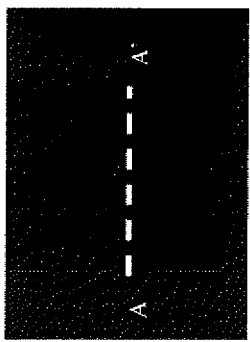
Figure 12D:
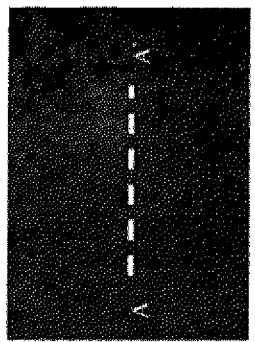
Figure 12E:
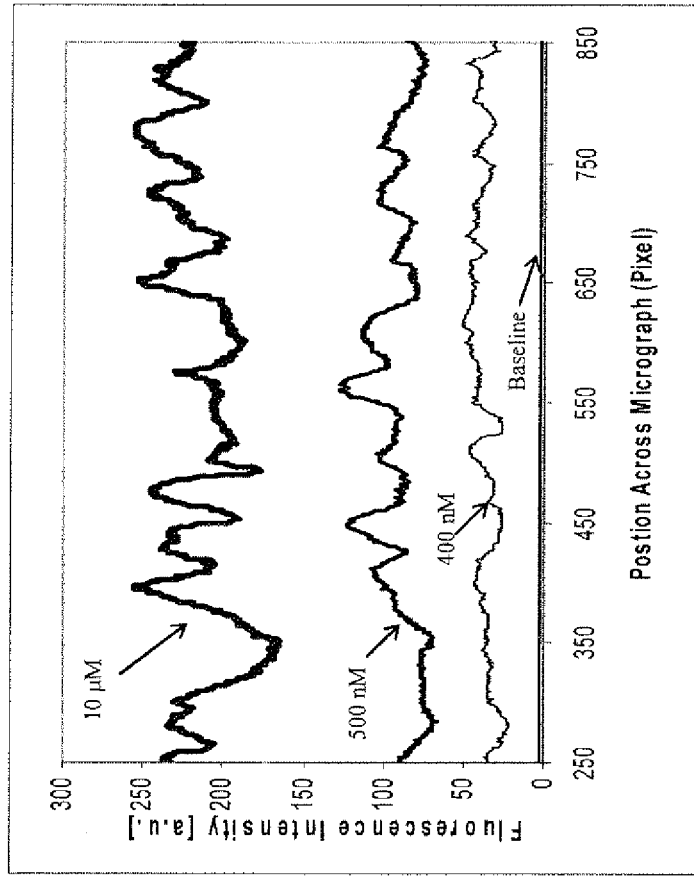

To determine the approximate binding time of TO-AMP molecules to fully saturate the affinity matrix, fluorescence micrographs in discrete time intervals (1 min) immediately following a sample injection of TO-AMP (400 nM) are recorded. Fluorescence intensity measurements are obtained in a straight line direction (A-A') across each micrograph, averaged and then plotted as a function of time (FIGS. 11(*a*)-(*b*)). Similar analysis techniques are used to quantitate all ensuing data. No appreciable increase in fluorescence intensity occurs after 10 minutes of incubation time.

To determine the ability of this SPE matrix to retrieve specific analytes, three sample solutions of TO-AMP (400 nM, 500 nM and 10 μM) are injected as described above. The solutions are allowed to interact with the matrix (10-15 min) and the chamber is then washed (50 μl/min for 15 min) with buffer before detection is performed. Imaging and fluorescence analysis conditions are similar to those used in the time resolved demonstration, only without resolving the temporal dimension. Data is presented in FIGS. 12(*a*)-(*e*). It is useful to note that the signals are distinct and non-overlapping for each concentration. The "noisy" nature of the signal comes from the dark areas in between individual beads, as shown by the micrograph insets (FIG. 12*a-d*), rather than actual noise in the signal. The baseline fluorescence supports this explanation. No other radiation wavelength is detected from the micrographs other than that which is specific to TO emission (530 nm), further emphasizing the selective nature of the TO-AMP/ATP-aptamer interaction.

Three different concentrations of TO-AMP solution are injected into this device producing 3 separate normalized fluorescence profiles, implying that gradual concentration can be achieved over time. This data suggests a potential concentration factor of 20 if identical injection and collection volumes are used. Although a 10 micro-molar solution of TO-AMP is the highest concentration used in the demonstrations, it presents no upper limit. It is feasible that the saturation threshold of TO-AMP to ATP-aptamer has not been breached as of yet for the packed microfluidic matrix presented in this demonstration.

The device is capable of capturing and releasing TO-AMP using two release techniques. The first is competitive displacement using a concentration gradient of ATP analyte (FIG. 13a). The second is thermal energy (FIG. 13b). After each competitive ATP solution (800 µM and 3.2 mM) injection (10 µl), fluorescence intensity is measured. Five extraction and release cycles are performed (2 shown here) using thermal energy. Solution conditions and sampling using TO-AMP (400 nM) closely tracks those employed in SPE demonstrations. Fluorescence measurements are taken after each capture and release wash procedure.

Competitive displacement is used for only one cycle since it proves less efficient at releasing TO-AMP than thermal energy. While thermal cycling, the extraction signal in cycle 2 deviates by 16.7 percent from that recorded during cycle 1. It is also determined that the transition temperature used to release TO-AMP from ATP-aptamer falls between a range (about 80-85° C.). It should be noted that the release temperature can vary according to the analyte, aptamer, and analyte/aptamer combination used and according to the particular purpose of the application. Initial attempts used 60 and 95 degrees centigrade while flowing buffer solution (2 min at 5 µl/min) to collect the released analyte; the latter causes denaturation of streptavidin and damage of the streptavidin-biotin (SB) bond, whereas the former does not unfold the aptamer/target bond. Even so, the use of any particular release technique depends on the particular parameters of the application. In some embodiments, competitive displacement can be used instead of thermal release, and competitive displacement remains within the scope of the described subject matter.

It should be noted that specific release temperatures can depend on the particular analyte, aptamer, or combination of analyte and aptamer used. In some embodiments, minimally invasive capture and release of analytes is performed at a temperature which is not harmful to the analyte and is at a temperature where thermal release occurs.

In other embodiments, the temperature control can be used to either raise or lower the temperature. For example, a resistor in contact with the micro chamber where the analyte/aptamer complex is located can be used to raise the temperature. In another embodiment, a cooling mechanism, such as an air cooler, refrigerant mechanism, or the like can be used to lower the temperature of the analyte/aptamer complex. The specific set point at which the aptamer/analyte bond is released can either be above the temperature of the device (e.g., the temperature raised using a heater) or can be lower than the temperature of the device (e.g., the temperature lowered using a cooling mechanism). The specific parameters and needs of the application can dictate the specific temperature shift needed for thermal release of the analyte.

Another embodiment demonstrates the principles of the described techniques. A microfluidic apparatus achieves specific extraction, concentration, and isocratic elution of biomolecular analytes with coupling to label-free mass spectrometric detection. Analytes in a liquid phase are specifically captured and concentrated via their affinity binding to aptamers, which are immobilized on microbeads packed inside a microchamber. Exploiting thermally induced, reversible disruption of aptamer-analyte binding via on-chip temperature control with an integrated heater and temperature sensor, the captured analytes are released into the liquid phase, and then isocratically eluted and transferred via a microvalve for detection via matrix-assisted laser desorption/ionization mass spectrometry (MALDI-MS). The functionality of the apparatus is demonstrated using adenosine monophosphate (AMP) as a model analyte. Results indicate that the device is capable of purifying and concentrating the analyte from a sample mixed with non-specific analytes and contaminated with salts. In addition, thermally induced analyte release is performed at one or more temperatures (e.g., 45° C.), and mass spectra obtained from MALDI-MS demonstrate detection of AMP at concentrations as low as 10 nM.

Some embodiments illustrate a microfluidic approach intended to improve SPE sample preparation for MALDI-MS. Using a miniaturized microchip, which is coupled to a MALDI-MS analysis plate, selective purification, enrichment, and enhanced label-free detection of trace amounts of a biomolecular analyte via aptamer-functionalized surfaces is described. This is possible due to affinity interaction between an analyte and an aptamer molecule, allowing highly discriminate purification. Moreover, exploiting the strong temperature dependence of the aptamer-analyte binding, recovery of the purified analyte and regeneration of the aptamer receptor are possible by a modest temperature increase (45° C.). This allows the analyte molecules to be eluted in a single aqueous phase; that is, isocratic elution is accomplished. The described device includes a microchamber packed with aptamer-functionalized microbeads for analyte extraction and purification, a microheater and temperature sensor for thermally induced analyte release, and microchannels in conjunction with a surface tension-based valve for the control of sample flow. The microfluidic chip is interfaced to a standard MALDI-MS analysis plate for mass quantification. Using the metabolic hormone adenosine monophosphate (AMP) as a model analyte, detection of AMP at varying concentrations, consecutive infusion of trace AMP to concentrate and purify the sample, and finally purification of AMP samples contaminated by either non-specific analytes or buffer salts is demonstrated.

Aptamers include oligonucleotides (e.g., 25-100 bases long) that recognize a broad class of analytes, such as small molecules, peptides, amino acids, proteins, viruses, and bacteria, via specific affinity interaction. They can be derived from ribonucleic (RNA) or deoxyribonucleic (DNA) acids, aptamers can be isolated through an in vitro procedure called systematic evolution of ligands by exponential enrichment (SELEX), whereby large populations of random sequence oligomers (DNA or RNA libraries) are continuously screened against a target molecule until highly selective candidates are isolated and subsequently amplified. Aptamers have been used in applications such as target validation, drug discovery, diagnostics, therapy, and in particular, analyte purification. Employed in the described microfluidic device, aptamers allow specific extraction and thermally induced recovery of biomolecular analytes.

Figure 21A:
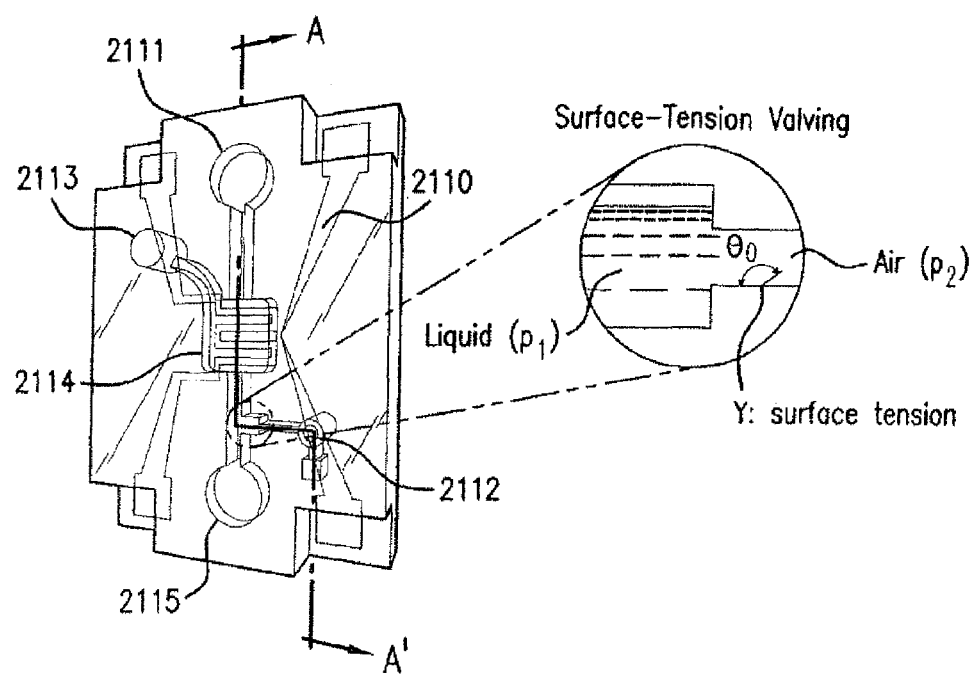
FIGS. 21(a)-(c) depict a schematic of the microchip purification device with an inset illustrating the surface-tension based valving scheme according to an embodiment of the described subject matter; (b) depicts a cross-sectional view along line A-A from (a) showing coupling scheme of the microchip to the MALDI analysis plate for sample spotting before mass spectrometric analysis according to an embodiment of the described subject matter; (c) depicts a close-up photograph of a packaged device according to an embodiment of the described subject matter.
Figure 21B:
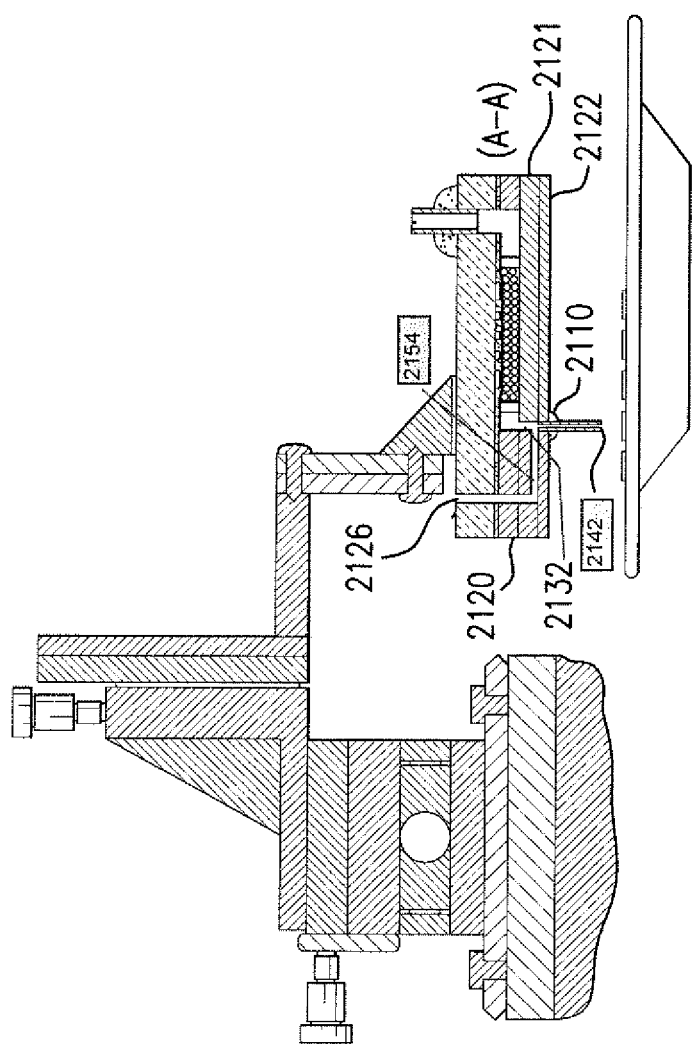
Figure 21C:
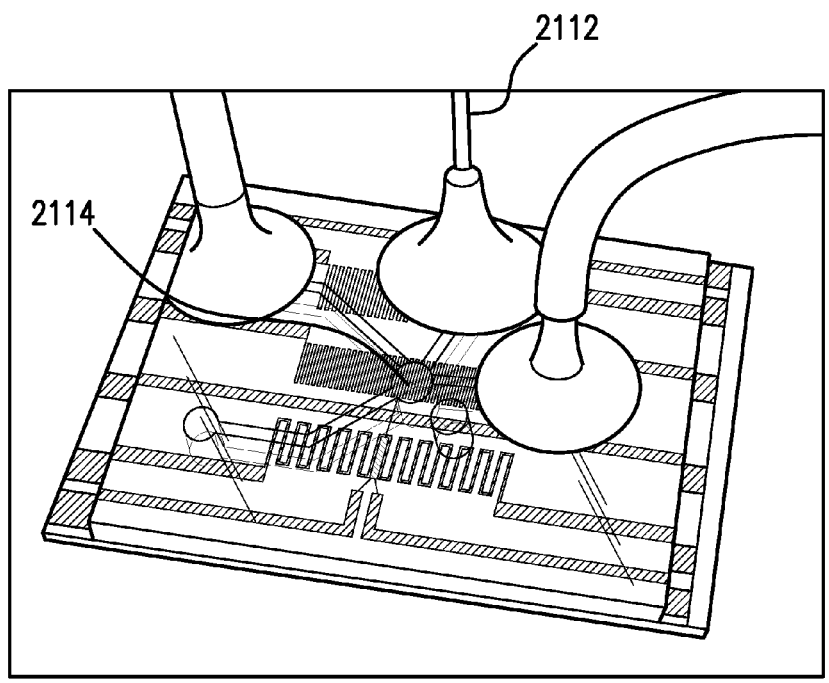

The microfluidic device of the described embodiments includes a microchamber packed with aptamer-immobilized microbeads for biomolecule analyte purification, a microheater and temperature sensor 2110 for thermally induced analyte release, and microchannels equipped with a passive valve using surface tension for transferring released analytes to a spotting outlet 2112 coupled to a MALDI analysis plate (FIGS. 21(a)-(c)). Samples and reagents are introduced via the sample inlet 2111, whereas the bead inlet 2113 is provisionally used for packing the microchamber with microbeads and is sealed afterward. The microchamber (3 mm×3 mm×180 µm) is tapered and includes structural weirs to retain the microbead support matrix on which the aptamer is immobilized. Such a design minimizes dead volume and bubble formation in the device. Hence, the chamber has an effective volume of ~1.62 µl with the tapers taken into consideration. For thermally induced reversible disruption of aptamer-analyte binding, a serpentine resistive heater and temperature sensor are placed below the aptamer chamber 2114 to promote efficient heating of the entire chamber and accurate sensing at the center of the microchamber. Using Cr/Au thin films, a 500 ω heater and 27.5 ω temperature sensor (with a temperature coefficient of resistance of $2.65 \times 10^{-3}$/° C.) can be used in conjunction with off-chip programming to control temperature and thus, vary thermal stimulation. The valve and deposition outlet are placed near the aptamer chamber to reduce analyte dilution after release due to adsorption to the channel walls or diffusion into dead fluid volumes. The device also includes a waste reservoir 2115.

The microfluidic chip structure is realized with three sandwiched polymer layers 2120-2122 (FIG. 21b). The bottom layer 2122 incorporates the inlets, passive valve 2132, and waste outlet 2134. To reduce bubble entrapment or dead volumes during sample spotting, the middle layer 2121 provides an air vent 2126 connected to the spotting outlet 2142. This provides a means for denser fluids to force trapped gas in the spotting outlet out through the air vent. Additionally, the middle layer 2121 encapsulates and seals the microfluidic network formed in the bottom layer 2122. Lastly, the top layer 2120 defines the spotting outlet 2152 and houses the air vent channel 2154. To interface the device to the MALDI, the device incorporates a glass capillary which is fitted to the opening of the microchip spotting outlet. For example, samples are infused from the capillary tip by hydrodynamic force and allowed to crystallize before mass spectrometry analysis.

During operation, an aqueous sample containing a biomolecular analyte intermixed with non-target molecules is introduced to the aptamer-functionalized surfaces within the microchamber, and thus is extracted by the aptamer (FIG. 21a). This occurs at a suitable (e.g., room) temperature so that the aptamer specifically captures the analyte from the liquid-phase while impurities are flushed from the apparatus through the waste outlet. The above sequence is repeated in a discrete (consecutive infusion of dilute sample) fashion in order to adequately purify and enrich the analyte, if necessary. Subsequently, the aptamer interaction mechanisms can be disrupted by altering the temperature of the solid support, such that the concentrated analyte is released into a plug of pure aqueous buffer, or MALDI matrix solution. Thus, the analyte can be isocratically eluted onto a MALDI analysis plate for MS detection. Returning the temperature to the initial state allows the aptamer to revert to its initial functional structure, i.e., the aptamer-functionalized surfaces are regenerated.

A microvalve is used to direct the purified analyte through a secondary channel to the spotting outlet, and deposited onto the MALDI analysis plate for MS detection (FIG. 21b). The microvalve (FIG. 21a) exploits surface tension in that a pressure difference exists at the air-liquid interface in a sudden restriction of a hydrophobic channel. This pressure difference serves as a pressure barrier: if and only if the pressure drop between the sample inlet to the valve exceeds the pressure barrier, the eluent will enter the secondary channel leading to the spotting outlet. This pressure drop is primarily determined by the microchamber, whose flow resistance is mainly due to the packed microbeads.

To demonstrate the functionality of the device, a model binding apparatus is used which includes AMP analyte which is recognized by an RNA aptamer derived for adenosine triphosphate (ATP-aptamer). AMP is captured by ATP-aptamer through an induced 11-base loop flanked by double-stranded RNA, which forms an affinity binding epitope for the small molecule.

Adenosine triphosphate aptamer (ATP-aptamer), with a 5'-end functionalized with biotin, is acquired. As MALDI-MS can be sensitive to salt impurities, DNA grade water (sterile RNase/Protease-free water) is used to prepare ATP-aptamer, AMP, cytidine, uridine, and guanosine triphosphate (CTP, UTP, and GTP, respectively) samples in addition to being used for all washes. An aqueous buffer solution (e.g., pH 7.4) is prepared with a mixture of water, Tris-HCl (20 mM), NaCl (140 mM), KCl (5 mM), and $MgCl_2$ (5 mM). The MALDI matrix solution (THAP) is prepared from 2,4,6-trihydroxy-acetophenone (2,4,6-THAP), 2,3,4-THAP, and diammonium citrate at 0.1, 0.05, and 0.075 M concentrations, respectively in a 3:5 (v:v) mixture of acetonitrile/water. UltraLink streptavidin coated bis-acrylamide/azlactone beads (e.g., 50-80 μm in diameter) are used to immobilize ATP-aptamer via a biotin-streptavidin link. Microfabrication materials, including SU-8 2025 and 2100, Remover PG, Sylgard 184 polydimethylsiloxane (PDMS), Torr Seal epoxy, polyethylene (PE) film, and microscope grade glass slides (25 mm×75 mm), are used, respectively. A DC power supply and a proportional-integral-derivative (PID) controlled LabVIEW program are used in parallel to control temperature during thermally-initiated analyte release from aptamer molecules. Lastly, a syringe pump is used for sample and introduction while a time of flight mass spectrometer is used for mass analysis.

Figure 22G:
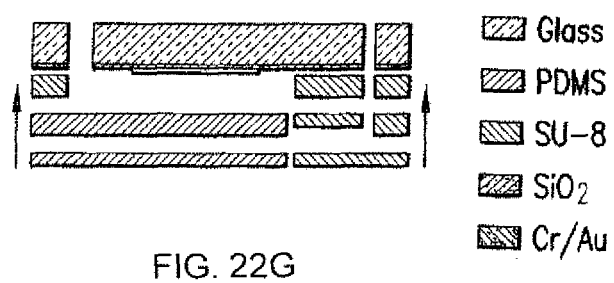
Figure 22H:
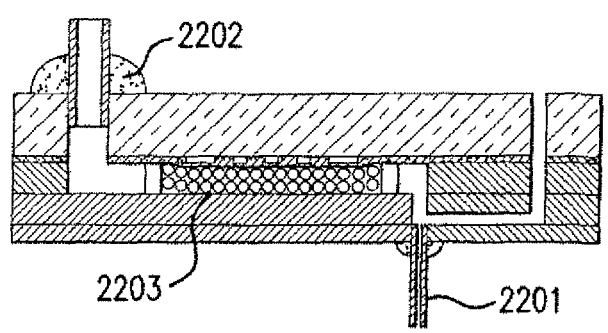

The device of the described embodiment is fabricated from PDMS and bonded on a glass substrate using standard soft lithography techniques (FIGS. 22 (a)-(h)). SU-8 masters for each microfluidic layer are first generated on silicon wafers. PDMS pre-polymer solution is mixed (e.g., 10:1/v:v) and then poured onto individual masters. A PE film (e.g., coated with an adhesive on one side) is subsequently layered over the prepolymer mixture, allowing surface tension forces to make intimate contact between the prepolymer and PE film. The master/prepolymer/transparency stack is then clamped within a through-hole PDMS sandwich assembly and cured for 45-60 min at 60° C. This produces thin PDMS microfluidic layers which can be peeled off from the masters via the PE films for bonding to the glass substrate. Meanwhile, glass substrates are diced (25 mm×30 mm) and drilled to create the inlets and outlets. Subsequently, Cr/Au (5/100 nm) thin films are deposited and patterned on the substrates via thermal evaporation and then passivated with $SiO_2$ using plasma-enhanced chemical vapor deposition (PECVD), realizing the microheater and temperature sensor. Following plasma ($O_2$) treatment of each bonding interface, all three PDMS layers and the glass substrate are aligned and permanently bonded. A glass capillary tube 2201 (5 mm×0.5 mm I.D.) is then inserted into the spotting outlet and fastened with Torr Seal 2202. Finally, microbeads 2203 are packed into the microchamber and the fluidic ports are sealed.

The device is first primed with a water wash (10 μl/min, 10 min). The following washing and loading schemes are identical. These parameters are specified based on the microchamber size (1.62 μl), which is created such that with the microbeads packed at an expected 63.5% efficiency, a fluid volume slightly over 1 μl (1.02 μl) can be attained. This is within the common volume range for sample spotting used in MALDI-MS analysis (0.5-2 μl). Initially, a 10 μM ATP-aptamer sample (10 μl) is loaded into the microchamber and allowed to incubate with the streptavidin functionalized bead bed (40 min). After subsequent washing, the device is primed. In parallel, a device not functionalized with ATP-aptamer (control device) is used to process control samples of AMP, CTP, UTP, GTP (1 μl; similar for all sample/matrix volumes in the following demonstrations) which are prepared at 1 μM each. The operational principle described above is used. Manually pipetted AMP, CTP, UTP, and GTP samples at 1 μM concentrations are deposited and analyzed to obtain reference spectrums. The separate data sets are compared to reveal sample loss incurred within the device during device operation.

For extraction and purification demonstrations using the microdevice, 10 nM, 100 nM and 1 µM AMP samples are loaded into the aptamer microchamber separately. A rinse follows to rid non-specific compounds. AMP is then released from the aptamer by raising the chamber temperature to 45° C. while introducing a matrix sample plug. The sample/matrix plug is then transferred to the spotting outlet and deposited onto the MALDI plate to be subsequently analyzed. Similarly, for applications concerning specific purification of AMP from model impurities, a solution of AMP (100 nM), CTP (1 µM), UTP (1 µM) and GTP (1 µM) is loaded into the microchamber. After incubation (e.g., 3 min), the impurity molecules are washed from the microchamber and matrix is introduced. Heat is applied, while the passive valve activated, to release the molecules currently on the aptamer and deposit them onto the MALDI plate for analysis.

For enrichment and enhanced detection of AMP, a multiple infusion scheme is used. The aptamer chamber is consecutively loaded with 10 nM infusions of AMP sample. Each infusion is incubated (3 min) and followed by a rinse. Upon suspected saturation of the aptamer with AMP, the microchamber is heated to release the analytes into a matrix plug, which is deposited for analysis.

To ensure the validity of higher-level data, properties of the valve in addition to absorption/adsorption characteristics of the microfluidic structure are obtained. At a steady flow rate, the pressure difference imparted by the passive valve impinges flow to access the spotting outlet. When the waste outlet is open and the flowrates are below 50 µl/min (e.g., 10 µl/min), fluid flow bypasses the passive valve since the hydrodynamic pressure driving flow (~686 Pa) is smaller than the actuation pressure of the valve. To direct flow to the MALDI plate, the pressure drop between the sample inlets to the waste outlet can be greater than the valve's actuation pressure (i.e., above 3.154 kPa). This can be accomplished by plugging the waste outlet using an external valve and maintaining a constant flow rate during analyte sample deposition following thermally induced release of biomolecules from the aptamer. Additionally, analyte loss during fluidic transfer from the microchamber to the spotting outlet is likely negligible, since data obtained from samples spotted using the control device match consistently to reference samples which are manually pipette and deposited onto the analysis plate.

To demonstrate the ability to extract and detect AMP by MALDI-MS using the device of the described embodiment, discrete samples of varying concentration of AMP (10 nM, 100 nM and 1.0 µM) are infused into the chamber. After interaction with the aptamer functionalized beads, the AMP molecules are released and transferred to the spotting outlet and finally deposited onto a MALDI-MS plate. Mass analysis follows (FIGS. 23 (a)-(c)). For attempted extraction and detection of samples with concentration at 10 nM (FIG. 23a), little or no signal can be obtained above the noise level. In fact, the present mass peaks corresponding to THAP matrix are limited to 339.44, 392.45, 468.23 and 502.05 Da/z. However, the mass spectrum of a spot obtained from a 100 nM AMP solution (FIG. 23b) shows a distinctive mass peak of 348.11 Da/z, which corresponds to AMP (established value: 347.22 Da/z) and indicates that the potential detection range of the device of the described embodiment lies between 10-100 nM. Since AMP concentration is still relatively low for this case, the magnitude of its peak is comparable to several peaks from the MALDI matrix (393.99 and 468.65 Da/z). Nonetheless, this detection sensitivity is c.a. one order lower than physiologically relevant AMP levels in plasma. In addition, a mass spectrum obtained from a 1.0 µM AMP solution (FIG. 23c) improves the analyte-to-matrix peak contrast. In this case, the AMP peak dominates matrix peak amplitudes and indicates a nonlinear dependence of detection signal to infused sample concentration. Furthermore, this suggests that concentrating undetectable dilute samples can improve the analyte detection limit.

In another embodiment, for high sensitivity MALDI-MS, analyte sample conditioning and enrichment can be useful to improve the detection signal. The device of the described embodiment can be used to enhance a sample of AMP (10 nM), previously established undetectable, by loading the dilute AMP sample into the aptamer chamber multiple times to saturate the analyte on the aptamer before release and mass spectrometric analysis. A dilute sample concentration is chosen to be much lower than 100 nM in order to highlight the detection enhancement due to this technique of enrichment. 25 consecutive dilute AMP samples are infused into the aptamer chamber, the captured AMP are released with heat into a pure matrix solution, and the concentrated plug is transferred to the spotting outlet. A spectrum is obtained from the resulting sample spot (FIG. 24a). An AMP peak to reference matrix ratio is observed which is slightly higher than that seen in FIG. 23b, demonstrating the successful concentration of AMP by ~10×. This result demonstrates the effectiveness of the microchip for enhancing the detection of low concentration analytes so as to facilitate label-free detection by MALDI-MS.

In yet another embodiment, to emphasize the capacity of this approach, more consecutive infusions of dilute (10 nM) AMP solution are performed in order to achieve a maximum enrichment factor for the device of the described embodiment. A maximum of 250 infusions are performed (FIG. 24b). Following the final infusion, a sample spot is obtained and analyzed with MALDI-MS similar to the protocol above with 25 infusions. Note that the AMP peak dominates those of reference peaks and the AMP peak to noise peak ratio is comparable to that of FIG. 23c. This suggests an AMP analyte enrichment factor of nearly 100×. This is a substantial concentration factor, comparable to that seen in reverse-phase SPE devices, but with the benefit of higher specificity and affinity imparted by aptamers. Moreover, by using the described enrichment protocol, the detection limit of the device to AMP is improved by an order of magnitude and now allows AMP detection at concentrations two orders below physiologically relevant levels. In some embodiments, AMP sample infusions are stopped after 250 since satisfactory signal enhancement is achieved at this time, not because of actual saturation of the analyte on the aptamer microbeads. The signal gain achieved in FIG. 24b is merely the apparent signal enhancement, since the potential for even larger enrichment factors and higher signal gain is possible with the microchip. The microchip can be regenerated (e.g., using thermal stimulation of the aptamer functionalized beads) to allow reuse and repeated functionality.

Purification of analytes can be a useful tool for selectively controlling analytes in biochemical applications. In other embodiments, the signal of AMP (100 nM) can be selectively isolated and enhanced from a homogeneous solution amongst CTP, UTP, and GTP (model nonspecific analytes at 1.0 µM each) by loading the sample into the microchamber and subsequently washing the chamber to isolate AMP on the aptamer functionalized beads. To emphasize the power of aptamer purification, the ratio of AMP to non-specific impurity analytes is reduced (1:10) in order to mimic more closely a common practical situation in which a target analyte can be in unfavorable disproportion to non-target analytes. A deposited sample spot is obtained similarly to previous protocols. The control device is used to establish a reference spectrum for an unclean sample. Both samples are compared to delineate the effectiveness of aptamer based sample cleanup prior to MALDI-MS (FIGS. 25(a)-(b)). For the control sample (FIG. 25a), the ratio of AMP to matrix is comparable to that seen in FIG. 23b, where only AMP is present in the solution. However, the non-target peaks corresponding to the model impurities are observed: CTP (480.01), UTP (484.51), and GTP (523.74) Da/z which can have an adverse effect on the signal quality. This is unlike the signal obtained utilizing the aptamer functionalized microchip, where cleaning of the AMP sample through extraction and purification is possible (FIG. 25b). A reduction of impurity peaks (e.g., that of CTP) exists, at the same time that the AMP signal is improved. Although the CTP, UTP and GTP are still present, their intensities are lower than the AMP peak for this case, suggesting that the amount of non-specific binding is negligible to the AMP-specific aptamer. Non-specific binding can degrade MALDI-MS detection for practical applications.

Along with potential interference from non-specific analytes, MALDI analysis can also be hindered by contamination of salts present in both conditioned solutions and physiological solutions. Since a particular analyte can be solvated within a solution stemming from one of these sources, addressing this type of contamination in analytical samples is useful before performing MALDI-MS. the microdevice is capable of selectively isolating AMP and enhancing its detection from a buffer solution contaminated with common pH altering salts (e.g., Tris-HCl, NaCl, KCl, and $MgCl_2$). These compounds can degrade the baseline generated for a given MALDI spectrum (e.g., the baseline is translated considerably above 0 Da/z), which can alter the relative intensities of significant analyte peaks as well as produce unwanted noise. A 100 nM AMP sample in buffer solution is initially desalinated by infusing the sample into the aptamer microchamber to allow specific interaction of the AMP to ATP-aptamer. Flushing the buffer solution through the waste outlet followed by a short wash procedure allows the analyte to be purified. This is followed with an infusion of a pure matrix plug and simultaneously initiating thermal release, sample transfer to the spotting outlet, and deposition of the analyte similar to previous protocols. The control microchip is used similarly to that described above to establish a reference spectrum for the salt laden sample. The spectrums are compared to reveal the effective desalting capability of the device (FIGS. 26 (a)-(b)). The control sample spectrum (FIG. 26a) reveals characteristic properties of a salt contaminated sample. For example, the baseline of the spectrum is raised significantly above 0 Da/z, altering the relative ratios of significant mass peaks. The AMP mass peak is barely registered above the baseline and noise peaks (265.90 Da/z), due to buffer salts, dominate instead. After using the aptamer functionalized chip for the same AMP sample, a reduction of the baseline to near 0 Da/z in can be observed addition to an enhanced AMP mass peak signal (FIG. 26b). There is a reduction of all impurity and salt peaks (e.g. 265 Da/z), which highlights the benefits of this microchip for desalination sample conditioning before MALDI-MS.

Other embodiments illustrate a microfluidic approach to characterizing biomolecular binding properties. The techniques include a microfabricated chip with biomolecule functionalized surfaces coupled to a matrix-assisted laser desorption/ionization mass spectrometer (MALDI-MS). The thermally-dependent binding properties of adenosine monophosphate, vasopressin, and platelet-derived growth factor can be observed with their respective aptamer receptors. A binding profile for each biomolecular pair revealed zones of either strong or weak interaction depending on the localized temperature. This platform can be useful for screening therapeutic and receptor ligands.

Some embodiments illustrate a label-free, microfluidic approach to characterizing the temperature-dependant nature of receptor-analyte interactions. The techniques are demonstrated with three devices based on synthetic affinity oligonucleotide receptors, aptamers and their specific analytes: (1) adenosine monophosphate (AMP) with an anti-AMP RNA aptamer; (2) platelet derived growth factor (PDGF) and its specific DNA aptamer; and (3) vasopressin with a specific RNA aptamer (called a spiegelmer). This is accomplished using an integrated microfluidic device coupled to label-free detection with matrix-assisted laser desorption/ionization mass spectrometry (MALDI-MS).

To characterize temperature dependent receptor-ligand binding, the receptor is immobilized on solid surfaces (FIGS. 27 (a)-(e)). At each of a selected series of temperatures, a sample containing the ligand, with a non-binding species for use as a reference standard in the subsequent quantification stage, is introduced in a defined volume to the receptor-functionalized solid surfaces (FIG. 27a). Alternatively, the ligand can be surface-immobilized while the receptor is solution-borne in the sample. The sample is then incubated for a sufficient time period, so that some of the ligand molecules bind with the receptor, while the reference standard remains in solution (FIG. 27b). The sample, now containing the ligand molecules not bound to the receptor along with the reference standard molecules, is transferred to a MALDI-MS analysis plate, and subsequently quantified by mass spectrometry (FIG. 27e). The normalized mass spectral peak of the ligand, defined as the ratio of the mass spectral peaks of the ligand and reference standard, will vary at the different temperatures. This relationship represents the temperature dependence of the equilibrium binding between the ligand and receptor. Also, initially bound molecules can be released by modifying the surface temperature above or below a binding temperature (FIG. 27c, d), while introducing a non-binding reference sample, to illustrate the efficiency of temperature dependent dissociation.

Using this approach, the temperature-dependent interaction properties between AMP and its specific aptamer is illustrated. However, in this apparatus, an anti-AMP aptamer is immobilized on microbeads while AMP in solution is introduced for binding, release, and subsequent MALDI-MS detection. Guanosine monophosphate (GMP) is utilized as a standard non-binding analyte. Using a single concentration of 10 µM AMP, binding is characterized from room temperature to 60° C. (FIG. 29). The AMP apparatus demonstrates optimal binding within the temperature range of 25-35° C., indicated by the low AMP to GMP mass peak ratio. Binding dissociation initiates in a temperature zone immediately higher than 35° C. and increases above 45° C.

Following the same protocol as AMP and its specific aptamer, the temperature dependent binding characteristics of PDGF and its correlating specific aptamer are illustrated. However, in this device, a PDGF specific aptamer is immobilized on microbeads while PDGF in solution is introduced for binding, release, and subsequent MALDI-MS detection. Furthermore, vascular endothelial growth factor (VEGF) is used as a non-binding standard. Using a single concentration of 10 µM PDGF, binding is characterized from room temperature to 60° C. (FIG. 30). In this case, good binding is illustrated in one temperature zone, 24-45° C. as indicated by a low normalized PDGF/standard peak. Release of PDGF from its specific DNA aptamer occurred in a single observable temperature zone: 45-60° C.

The polypeptide, vasopressin, from room temperature to 75° C. is then characterized (FIG. 31). A wide spiegelmer concentration range (0.01, 0.1, 1 and 10 µM) with equal concentrations of P18 standard was used. For example, with a 10 µM spiegelmer/standard sample, good binding is illustrated in two temperature zones, 34-45° C. and 70-75° C. This is indicated by a low normalized spiegelmer/standard peak. Release of spiegelmer from the vasopressin (indicated by a high normalized peak) occurs in three temperature zones: 15-30° C.; 50-65° C.; and above 75° C. This is similar for all demonstrated concentrations, indicating consistency over three orders of magnitude.

Thus, the described apparatus can be used as a powerful tool for label-free characterization of temperature dependent binding of biomolecular targets with aptamers. Such complex binding profiles can be difficult to elucidate with conventional approaches. Additionally, these concepts provide techniques for surface-based biosensor characterization.

Further embodiments illustrate a microfluidic aptameric biosensor, or aptasensor, for selective detection of clinically relevant analytes with integrated analyte enrichment, isocratic elution and label-free detection by mass spectrometry. Using a microfluidic platform that is coupled to matrix assisted laser desorption/ionization mass spectrometry (MALDI-MS), specific purification, enrichment, and label-free detection of trace amounts of arginine vasopressin (AVP), a peptide hormone that is responsible for arterial vasoconstriction is demonstrated. During extreme physical trauma, in particular immunological shock or congestive heart failure, AVP is excreted abnormally and is hence a biomarker for such conditions. The device uses an aptamer, e.g., an oligonucleotide that binds specifically to an analyte via affinity interactions, to achieve highly selective analyte capture and enrichment. In addition, via thermally induced reversible disruption of the aptamer-analyte binding, the device can be easily regenerated for reuse and allows isocratic analyte elution, i.e., release and collection of analytes using a single aqueous solution.

Furthermore, the device of the current embodiment is coupled to MALDI-MS using a microfluidic flow gate, which directs the eluted analyte onto a MALDI sample plate for mass spectrometry. First, systematic characterization of kinetic and thermal release properties, as well as the overall timescale of the assay, is performed using fluorescently labeled AVP. Then, MALDI-MS detection of unlabeled AVP at clinically relevant concentrations approaching 1 pM is illustrated.

In the current embodiment, the specific aptameric isolation and enrichment, as well as label-free MALDI-MS detection, of AVP is illustrated. Using a microfluidic device of the present embodiments, AVP is first selectively captured and enriched on an aptamer-functionalized solid phase, and then collected using microflow gating and thermally induced isocratic elution (i.e., elution within the same aqueous phase for analyte capture) on a MALDI sample plate for mass spectrometric analysis. Systematic characterization of the aptasensor is first illustrated using fluorescently labeled AVP, including time-resolved measurements of aptamer-AVP interaction, concentration-dependent fluorescence response of AVP, temperature-dependent aptamer-AVP dissociation, and detection of trace AVP after enrichment of a dilute sample. Label-free detection of AVP, in the presence of significant levels of model impurities, at both physiologically critical concentrations (i.e., during symptoms of immunological shock and renal congestive heart failure) and normal conditions is then illustrated. In this way, the required time to detect AVP is reduced to within a working day (compared to 3-11 days for conventional approaches), while eliminating unnecessary chemical modification protocols such as those required for fluorescent or radiometric probes. Moreover, by integrating MEMS technology with microfluidics, these techniques provide a foundation for point-of-care and automated diagnosis of AVP maladies.

OF THE DESCRIBED EMBODIMENT includes a microchamber 3201 packed with aptamer-functionalized microbeads for sample purification, a microheater and temperature sensor 3202 for thermally induced analyte release, and microchannels equipped with a surface tension-based passive microflow gate and air vent for transferring released sample to a spotting outlet 3203 coupled to a MALDI sample plate (FIG. 32a). FIG. 32a also shows a sample inlet 3204, a bead inlet 3205, a valve 3206 and a waste outlet 3207. Structurally, the device includes a glass coverslip bonded to three stacked polymer layers (FIG. 32b): the bottom layer 3210 incorporates the inlets 3220, passive flow gate 3222, and waste outlet 3224; the middle layer 3211 contains the air vent 3226 and seals the bottom-layer microfluidic features; and the top layer 3212 defines the spotting outlet 3232, to which a glass capillary 3228 is fitted to allow sample ejection to a MALDI sample plate. The top layer 3212 also houses the air vent channel 3230, whose hydrophobic surface allows trapped gas bubbles to be eliminated from the spotting outlet 3232. Microbeads on which aptamer molecules are immobilized are packed inside the microchamber (volume: 1.6 µm) and retained by dam-like micro weirs. A thin-film resistive metal heater and temperature sensor are integrated on the glass surface to allow on-chip, closed-loop temperature control. FIG. 32c shows another view of the spotting outlet and the aptamer chamber 3208.

During operation, an aqueous sample containing AVP potentially intermixed with non-target molecules is introduced into the aptamer microchamber, and thus is extracted by the aptamer. This occurs at a suitable temperature (e.g., ~37° C.) so that the aptamer specifically captures the target from the liquid-phase while impurities are flushed from the apparatus through the waste outlet. The above sequence is repeated in a continuous fashion in order to adequately purify and enrich the analyte, if necessary. For MALDI-MS analysis, the aptamer interaction mechanisms can be disrupted by altering the temperature of the solid support, such that the concentrated analyte is released into a plug of pure MALDI matrix solution. Subsequently, the microflow gate is utilized to transfer the plug to the spotting outlet by exploiting the pressure difference induced across an air-liquid interface in a hydrophobic channel restriction. If the pressure drop between the sample inlet to the flow gate exceeds this pressure difference, fluid can enter the secondary channel leading to the spotting outlet. Hence, the fluid can be switched between the channels that access the spotting outlet or bypass it to the waste outlet. The air vent connected to the spotting outlet provides a means to reduce bubble entrapment or dead volumes during sample spotting. Thus, purified and enriched samples are ejected from the capillary tip by hydrodynamic force and allowed to crystallize before mass spectrometry analysis. This preceding protocol allows isocratic elution of analytes onto a MALDI sample plate for MS detection. Returning the temperature to the initial state allows the aptamer to revert to its initial functional structure, i.e., the aptamer-functionalized surfaces are regenerated.

The device of the present embodiment can be fabricated by standard soft lithography techniques. Briefly, sheets of polydimethylsiloxane (PDMS) bearing the microfluidic features are obtained by micromolding using a master fabricated from SU-8 on silicon, while the microheater and temperature sensor are fabricated from a 100 nm gold thin film (using a 5 nm chromium adhesion layer) on glass. Each PDMS sheet is then bonded to the glass chip, as shown in FIG. 32b, after treating the bonding interfaces by oxygen plasma. Microfabrication materials, for example, SU-8 2025 and 2100 (MicroChem), Sylgard 184 PDMS, Torr Seal epoxy, and microscope grade glass slides (25 mm×75 mm), are obtained.

Illustration of the described techniques involves systematic device characterization using fluorescently labeled AVP with respect to adenosine monophosphate (AMP) as a model impurity, and demonstration of capture, enrichment and MALDI-MS detection of unlabeled AVP from AMP. The AVP-specific aptamer, termed a spiegelmer, is derived from an L-type enantiomeric RNA sequence (5'-Biotin-(HEG18) GGGGUAGGGCUUGGAUGGGUAGUACAC (HEG18) GUGUGCGUGGU-3' (SEQ ID NO: 1), HEG18 is a hexaethylene glycol linker) and this sequence resists degradation by free ribonucleases. It is synthesized using nuclease-resistant L-type enantiomeric nucleotides. Meanwhile, unlabeled AVP is synthesized on peptide synthesizer, and AVP labeled with the fluorescent dye Tamra (TMR-AVP) is synthesized by coupling AVP peptide with dye Tamra. Unlabeled AMP is obtained while AMP labeled with the fluorescent dye thiazole orange (TO-AMP) is synthesized by coupling TO-hydroxysuccinimidyl ester with AMP-NH-linker-NH$_2$. Analytical samples used during fluorescently based characterization experiments involving TMR-AVP are prepared in buffer solution (AVP-buffer, pH 7.4) including purified water (sterile RNase/Protease-free), Tris-HCl (20 mM), NaCl (150 mM), KCl (5 mM), CaCl$_2$ (1 mM), and MgCl$_2$ (1 mM); while samples utilized in MALDI-MS protocols required solvation in purified water. A MALDI matrix, cyano-4-hydroxycinnamic acid is solvated in a volume ratio mixture of 50:50:0.3 purified water/acetonitrile/trifluoroacetic acid. Porous bis-acrylamide beads copolymerized with azlactone (50-80 µm in diameter) and coated with UltraLink streptavidin are used to immobilize receptor or ligand moieties via a biotin-streptavidin link.

The described devices are initially rinsed thoroughly (flow rate: 10 µl/min) with purified water for 30 minutes (similar for subsequent rinses in all experiments). Sample solutions in varying concentrations of TMR-AVP and unlabeled AVP are prepared using the appropriate mass weights of the respective compound and either AVP-buffer (for TMR-AVP), or water (for AVP) solution. Manual pressure was utilized to pack microbeads from the bead introduction channel of the aptasensor into the microchamber. After another rinse procedure, an AVP-aptamer solution (50 µM) was injected (3 µl, 50 µl/min) and allowed to incubate (40 min) in the chamber. (This procedure was used for all sample injections.) A inverted epi-fluorescence microscope (e.g., Nikon Eclipse TE300) is used for fluorescence characterization. Initially, a baseline fluorescence signal was acquired by focusing a 10× objective at a central location in the extraction chamber and averaging an 8-bit RGB signal over the entire recorded fluorescence image. Alternatively, MALDI-MS experiments are performed using a time of flight mass spectrometer (e.g., from Applied Biosystems, Voyager-DE).

Systematic characterization of the AVP-aptamer binding using TMR-AVP (peak absorption: 540 nm; peak emission: 580 mm) is performed. Then, MALDI-MS analysis is performed. The fluorescently based characterization allows for the visualization the binding characteristics of the apparatus.

Several initial procedures are performed using a microchamber with and without AVP-aptamer functionalized beads. The beads are introduced to samples of TMR-AVP and a model impurity, TO-AMP (peak absorption: 480 nm; peak emission: 530 nm). After a baseline fluorescence signal is acquired, the chamber is initially packed with non-functionalized beads (streptavidin-coated microbeads: ("bare beads")). Subsequently, samples of TMR-AVP and TO-AMP (1 µM) are injected into the microchamber. The resulting fluorescence gain is measured. Similarly, TMR-AVP and TO-AMP samples (1 are exposed to a chamber packed with AVP-aptamer functionalized microbeads. As shown in FIG. 33, there is little or no appreciable signal above the baseline in the bare beads case for both TMR-AVP and TO-AMP samples, while merely an increase of 1.45% in fluorescence over the baseline occurs when TO-AMP is introduced to AVP-aptamer. In contrast, the fluorescent intensity from introducing TMR-AVP to AVP-aptamer is dominant. TMR-AVP indeed interacts with AVP-aptamer. Moreover, this result highlights the specificity between the binding of AVP-aptamer and AVP.

The time course of affinity capture of TMR-AVP by the aptamer is obtained to illustrate the kinetic behavior of the apparatus. This is accomplished by recording the time-resolved fluorescence response after introducing a TMR-AVP sample into the aptamer microchamber. Fluorescence micrographs are taken at discrete time intervals (5 s) following an injection of TMR-AVP in varying concentrations (0.01, 0.1, and 1 µM). To reduce the effect of fluorescent photobleaching, the shutter to the mercury lamp is closed for the time period between all signal measurements. Fluorescence signal measurements are obtained, averaged and then plotted as a function of time (FIG. 34). The fluorescence intensity increases steadily with time until sufficient signal saturation occurs. The apparent AVP capture time (i.e., time constant for the observed time course of AVP capture) is approximately 8.4, 13.5, and 22.1 s for 1, 0.1, and 0.01 µM TMR-samples, respectively. The binding time can be affected by three time scales: thermal, diffusion and kinetic. For the porous microbead-packed microchamber, the diffusion time scale is approximately $d^2/D$~5.85 s, where d is the average bead diameter (50 µm), and D the analyte diffusivity (approximately ~4×10$^{-6}$ cm$^2$/s for AVP). This result is significant compared with the apparent analyte capture times seen in FIG. 36. Thus, the interaction between AVP and its aptamer in this situation can depend on both kinetics and diffusion. Further, the longer apparent capture times observed for lower AVP concentrations agrees with monovalent binding theory. Illustrated below, these apparent capture times provide a basis for choosing the sample incubation time (for concentration dependent fluorescence response) or infusion flow rate (for analyte enrichment). To confirm aptamer-based capture of AVP within the aptasensor microchamber, solutions of TMR-AVP at five different concentrations (0.001, 0.01, 0.1, 1, and 10 µM) were injected into the microchamber. After each sample introduction, fluorescence yield was quantified after an initial 30 s incubation time to assure equilibrium sample binding. Following the extraction of AVP, the microchamber was washed with buffer to rid all non-specific compounds, un-reacted molecules, and impurities. Results are presented in FIG. 35. It can be seen that below 1 nM, no measurable signal above the baseline is detected. Concentrations at and above 1 nM, however, are readily detectable for the aptasensor with c.a. a signal-to-noise ratio of 3. Additionally, the concentration dependent fluorescence signal produced through TMR-AVP capture appeared to be dose-responsive.

This was signified by the S-shape fit of the data using Graph-Pad Prism 5 (GraphPad Software) software. These results suggested the need for enhanced detection techniques, such as analyte enrichment, in order to render the aptasensor clinically viable; in other words, enable detection of AVP below 1 nM at physiologically and clinically relevant levels (e.g., 1-500 pM).

To investigate detection enhancement of TMR-AVP, a continuous-flow analyte enrichment scheme is used. A dilute solution of TMR-AVP (100 pM) is continuously infused into the microchamber until fluorescence saturation is observed. Taking into consideration the required residence time determined above, the sample flow rate is chosen to be 15 µl/min (corresponding to a sample residence time of 20 s in the microchamber) to insure complete AVP interaction with the aptamer. Fluorescence signals are obtained periodically (e.g., every 60 min) until approximately 480 min, when no significant increase in fluorescence was observed, which suggested saturation (FIG. 36). This agrees with the expected equilibrium condition that concentration of a molecular analyte onto a receptor modified surface increases consistently with time at a decreasing rate. Moreover, the observed fluorescence response of the original 100 pM sample corresponds to the apparent fluorescence response of a 0.1 µM TMR-AVP sample, indicating significant detection enhancement. Hence, using the analyte enrichment feature of the aptasensor demonstrates clinical potential for vasopressin diagnostics since shock and congestive heart failure AVP signaling levels in plasma are c.a. 100-500 pM. Moreover, the required processing time to perform enhanced detection of TMR-AVP with the aptasensor, although seemingly long (8 hrs), is drastically improved over conventional techniques, which require nearly 11 days.

Characterization of the temperature-dependant reversibility of AVP and AVP-aptamer binding enables label-free MALDI-MS detection. This is accomplished in the device of the described embodiments by thermally activated release and isocratic elution of analytes from aptamer-functionalized microbeads. To demonstrate this, a 1 µM TMR-AVP solution is first introduced into the microchamber and allowed to associate with AVP-aptamer. After binding of TMR-AVP on the aptamer surface, a high intensity fluorescence signal is observed (FIG. 37). The temperature on-chip is then increased to a predetermined setpoint and held for 2 min while AVP-buffer is flowed into the microchamber. The procedure is repeated for several elevated setpoint temperatures ranging from 34-60° C. A sharp decrease (93%) in fluorescence intensity occurs at 50° C. that continues until fully suppressed at 58° C., indicating nearly complete reversal of TMR-AVP binding on the microbeads. The effect of photobleaching is determined negligible. This demonstrates the capability of the aptasensor of the described embodiment for thermally activated release and isocratic elution of a captured target. This technique is also used to perform repeated demonstrations with TMR-AVP samples within the same aptasensor chip. The fluorescence signals resulting from TMR-AVP extraction and release in all demonstrations produces consistent and repeatable values, as reflected by the error bars on the data. This indicates that the thermal stimulation does not affect the functionality of the aptamer molecules and successfully allows for aptasensor regeneration and repeated use.

To demonstrate the ability to extract and detect AVP by MALDI-MS, discrete samples of physiologically relevant concentrations of AVP (1 pM, 10 pM, 100 pM, and 1 nM) are first introduced into the chamber. After interaction with the aptamer functionalized beads, the AMP molecules are thermally released and transferred to the spotting outlet via the passive microflow gate and finally deposited onto a MALDI-MS plate. Mass analysis follows (FIGS. 38(a)-(d)). No molecular ion peak registers for the 1 pM sample (FIG. 38a). In fact, only mass peaks corresponding to the HCCA matrix and its fragments/adducts are present (377.6, 648.2 and 860.5 Da/z). However, the mass spectra of a spots obtained for all other AVP solutions (FIG. 38b-d) shows a distinctive molecular ion peak of 1084.4 Da/z that corresponds to AVP. For example, sample AVP concentrations between 10 pM and 1 nM (FIG. 38b-d) demonstrates improved detection and signal-to-noise ratio with increasing concentration. However, since AVP concentration is still rather low for sample concentrations between 10 pM and 1 nM, the magnitude of its peak is smaller than the MALDI matrix peaks (e.g., 377.6 Da/z). Moreover, this detection sensitivity is c.a. on the order of average physiological AVP levels in plasma. To improve detection at low levels (e.g., 1-100 pM) analytes can also be enriched in the aptasensor prior to MALDI-MS.

Naturally occurring hormonal vasopressin is present in plasma predominantly above 1 pM. To demonstrate detection at this level and therefore pervade all clinical settings, poorly, or undetectable, samples of AVP are enriched using continuous infusion of an original dilute AVP solution. Particular protocol parameters, such as saturation time (~8 hrs) and flow rate (15 µl/min) are drawn from the above demonstrations. Following a similar process, dilute samples of AVP (1, 10, and 100 pM) are continuously infused into the aptamer chamber for the designed time period. This is followed by thermally induced release of the captured AVP into a pure matrix solution (1 µl), and subsequent transfer of the enriched analyte plug to the spotting outlet. A mass spectrum is obtained from the resulting sample spot (FIGS. 39 (a)-(c)). For each original dilute sample, there is an enhanced detection of the molecular ion peak for AVP. Specifically, the original 1, 10 and 100 pM samples produce mass spectra where the AVP peak compares to (or is better than, in the case of the 100 pM sample) 100 pM, 1 nM, and 100 nM samples measured in the previous demonstration, respectively. Notably, the 1 pM sample, which was undetectable before analyte enrichment, became quantifiable afterwards. Although the repeated use of the aptasensor is not explicitly gleaned from the presented data (due to the limits of presenting spectroscopic data), the aptasensor is easily regenerated (using thermal stimulation of the aptamer functionalized beads) to allow reuse and repeated functionality.

The foregoing merely illustrates the principles of the described subject matter. Various modifications and alterations to the described embodiments will be apparent to those skilled in the art in view of the teachings herein. It will thus be appreciated that those skilled in the art will be able to devise numerous techniques which, although not explicitly described herein, embody the principles of the described subject matter and are thus within its spirit and scope.

The invention claimed is:

1. A method for selectively increasing the concentration of an analyte, comprising:
   (a) functionalizing a solid phase with an aptamer;
   (h) introducing the analyte to the aptamer in an impure form;
   (c) binding the analyte to the aptamer;
   (d) washing the bound aptamer analyte complex to remove impurities;
   (e) repeating (a)-(d) until a desired analyte concentration is reached;
   (f) decreasing the temperature of the aptamer such that the analyte is released from the aptamer; and
   (g) re-using the aptamer for capture and release of analytes.

2. The method of claim 1, wherein analyte capture and release occurs in an aqueous medium without altering solvent composition.

3. A method for using aptamers for the capture and selective release of an analyte, comprising:
   (a) binding an analyte to an aptamer, the aptamer functionalized on a solid phase;
   (b) adjusting a temperature to release the analyte from the aptamer; and
   (c) re-using the aptamer for capture and release of analytes,
   wherein the binding the analyte to the aptamer comprises binding the analyte to the aptamer at a first temperature, and wherein adjusting the temperature comprises reducing the temperature of the aptamer to a second temperature which is lower than the first temperature.

4. The method of claim 3, further comprising introducing the analyte to the aptamer in impure form and washing the bound analyte to remove impurities.

5. The method of claim 3, further comprising collecting and detecting the analyte.

6. The method of claim 5, wherein the detecting comprises performing mass spectrometry on the released analyte.

7. The method of claim 5, wherein detecting comprises detecting fluorescence intensity.

8. The method of claim 3, wherein the analyte comprises an oligonucleotide.

9. The method of claim 3, wherein the analyte comprises a cell.

10. The method of claim 3, wherein the second temperature is between 15° C. and 30° C.

11. The method of claim 3, wherein the second temperature is between 50° C. and 65° C.

12. The method of claim 3, wherein analyte capture and release occurs in an aqueous medium without altering solvent composition.

13. A method for using aptamers for the capture and selective release of an analyte, comprising:
   (a) binding an analyte to the aptamer, the aptamer being functionalized on a solid phase; and
   (b) adjusting a temperature to release the analyte from the aptamer,
   wherein binding the analyte to the aptamer comprises binding the analyte to the aptamer at a first temperature, and wherein adjusting the temperature comprises reducing the temperature of the aptamer to a second temperature which is lower than the first temperature.

14. The method of claim 13, further comprising:
   (c) introducing the analyte to the aptamer in an impure form;
   (d) washing the bound analyte to remove impurities; and
   (e) repeating (c), (a), and (d) such that the amount of bound analyte is increased.

15. The method of claim 13, further comprising collecting and detecting the analyte.

16. The method of claim 15, wherein the detecting comprises performing mass spectrometry on the released analyte.

17. The method of claim 15, wherein the detecting comprises detecting fluorescence intensity.

18. The method of claim 13, wherein the solid phase comprises a microbead.

19. The method of claim 13, wherein the analyte includes an oligonucleotide.

20. The method of claim 13, wherein the analyte comprises a cell.

21. The method of claim 13, wherein analyte capture and release occurs in an aqueous medium without altering solvent composition.

* * * * *